(12) United States Patent
Liverton et al.

(10) Patent No.: US 8,309,540 B2
(45) Date of Patent: Nov. 13, 2012

(54) HCV NS3 PROTEASE INHIBITORS

(75) Inventors: Nigel J. Liverton, Harleysville, PA (US); Joseph P. Vacca, Telford, PA (US); John A. McCauley, Maple Glen, PA (US); Joseph J. Romano, Berwyn, PA (US); Michael T. Rudd, Collegeville, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 529 days.

(21) Appl. No.: 12/446,763

(22) PCT Filed: Oct. 22, 2007

(86) PCT No.: PCT/US2007/022419
§ 371 (c)(1),
(2), (4) Date: Apr. 23, 2009

(87) PCT Pub. No.: WO2008/051514
PCT Pub. Date: May 2, 2008

(65) Prior Publication Data
US 2010/0093779 A1    Apr. 15, 2010

Related U.S. Application Data

(60) Provisional application No. 60/853,964, filed on Oct. 24, 2006.

(51) Int. Cl.
*A61K 31/33* (2006.01)
*A61K 31/47* (2006.01)
*C07D 201/16* (2006.01)
*C07D 223/00* (2006.01)
*C07D 267/02* (2006.01)
*C07D 273/00* (2006.01)

(52) U.S. Cl. ........ 514/183; 514/311; 514/312; 540/544; 540/545; 540/540; 540/541

(58) Field of Classification Search .................. 540/544, 540/545, 540, 541; 514/183, 311, 312
See application file for complete search history.

(56) References Cited

U.S. PATENT DOCUMENTS

| | | | |
|---|---|---|---|
| 3,480,613 A | 11/1969 | Walton | |
| 6,323,180 B1 | 11/2001 | Llinas-Brunet et al. | |
| 6,329,417 B1* | 12/2001 | Llinas-Brunet et al. | 514/422 |
| 6,608,027 B1 | 8/2003 | Tsantrizos et al. | |
| 6,777,395 B2 | 8/2004 | Bhat et al. | |
| 6,955,174 B2 | 10/2005 | Joye et al. | |
| 7,470,664 B2 | 12/2008 | Holloway et al. | |
| 7,705,146 B2* | 4/2010 | Bailey et al. | 544/141 |
| 2002/0019363 A1 | 2/2002 | Ismaili et al. | |
| 2002/0107138 A1 | 8/2002 | Hoveyda et al. | |
| 2002/0107181 A1* | 8/2002 | Chen et al. | 514/9 |
| 2003/0181363 A1* | 9/2003 | Llinas-Brunet et al. | 514/9 |
| 2003/0236216 A1 | 12/2003 | Devos et al. | |
| 2004/0006007 A1 | 1/2004 | Gosselin et al. | |
| 2004/0063658 A1 | 4/2004 | Roberts et al. | |
| 2004/0067901 A1 | 4/2004 | Bhat et al. | |
| 2004/0229776 A1 | 11/2004 | Chen et al. | |
| 2004/0229818 A1 | 11/2004 | Llinas-Brunet et al. | |
| 2004/0254159 A1 | 12/2004 | Hasvold et al. | |
| 2004/0266668 A1 | 12/2004 | Nakajima et al. | |
| 2005/0020503 A1 | 1/2005 | Llinas-Brunet et al. | |
| 2005/0038240 A1 | 2/2005 | Connolly et al. | |
| 2006/0257980 A1 | 11/2006 | Li | |
| 2007/0027071 A1 | 2/2007 | Holloway et al. | |

FOREIGN PATENT DOCUMENTS

| | | |
|---|---|---|
| EP | 1719773 A1 | 11/2006 |
| GB | 2337262 A | 11/1999 |
| GB | 2430621 A | 4/2007 |
| WO | 97/041211 A1 | 11/1997 |
| WO | 98/022496 A2 | 5/1998 |
| WO | 98/046630 A1 | 10/1998 |
| WO | 99/07733 A2 | 2/1999 |

(Continued)

OTHER PUBLICATIONS

West, Solid state chemistry and its application, Wilsy, New York, 1988. pp. 358, 365.*
Vippagunta et al. "Crystalline solid," Advanced, drug, Delivery, 2001, vol. 48, pp. 3-26.*
Ulrich "Crystallization," Chapter 4, Kirk-Othmer Encyclopedia of Chemical techology, John, Wiley and Sons, 2002.*
Testa "Prodrug research: Futele or fertile?" Biochemical Pharmacology, 2004, vol. 68, 2097-2106.*
Youwei Yan et al., Complex of NS3 protease and NS4A peptide of BK strain hepatitis C virus: A 2.2 Angstrom resolution structure in a hexagonal crystal form, 7 Protein Science 837 (1998).

(Continued)

*Primary Examiner* — ShengJun Wang
(74) *Attorney, Agent, or Firm* — Melissa B. Wenk; Sheldon O. Heber

(57) ABSTRACT

The present invention relates to macrocyclic compounds of formula (I) that are useful as inhibitors of the hepatitis C virus (HCV) NS3 protease, their synthesis, and their use for treating or preventing HCV infections. (I)

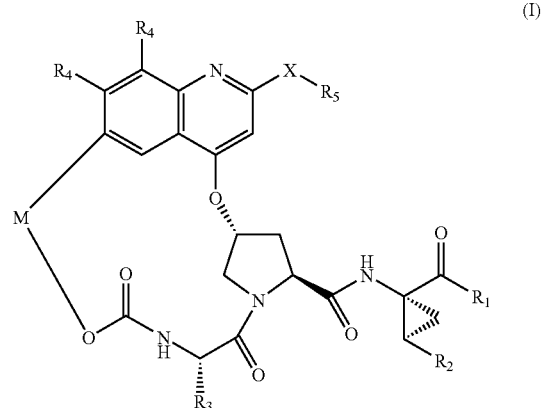

24 Claims, No Drawings

FOREIGN PATENT DOCUMENTS

| | | |
|---|---|---|
| WO | 99/07734 A2 | 2/1999 |
| WO | 99/38888 A1 | 8/1999 |
| WO | 99/43691 A1 | 9/1999 |
| WO | 99/50230 A1 | 10/1999 |
| WO | 99/64442 A1 | 12/1999 |
| WO | 00/09543 A2 | 2/2000 |
| WO | 00/09546 A2 | 2/2000 |
| WO | 00/25780 A1 | 5/2000 |
| WO | 00/59929 A1 | 10/2000 |
| WO | 01/00622 A1 | 1/2001 |
| WO | 01/47883 A1 | 7/2001 |
| WO | 01/60379 A1 | 8/2001 |
| WO | 01/68663 A1 | 9/2001 |
| WO | 01/77091 A2 | 10/2001 |
| WO | 01/77113 A2 | 10/2001 |
| WO | 01/79246 A2 | 10/2001 |
| WO | 01/90121 A2 | 11/2001 |
| WO | 01/92282 A2 | 12/2001 |
| WO | 02/04425 A1 | 1/2002 |
| WO | 02/06246 A1 | 1/2002 |
| WO | 02/18404 A2 | 3/2002 |
| WO | 02/20497 A1 | 3/2002 |
| WO | 02/32920 A2 | 4/2002 |
| WO | 02/48116 A2 | 6/2002 |
| WO | 02/48165 A2 | 6/2002 |
| WO | 02/48172 A2 | 6/2002 |
| WO | 02/051425 A1 | 7/2002 |
| WO | 02/057287 A2 | 7/2002 |
| WO | 02/057425 A2 | 7/2002 |
| WO | 02/100415 A2 | 12/2002 |
| WO | 03/015755 A1 | 2/2003 |
| WO | 03/026589 A2 | 4/2003 |
| WO | 03/026675 A1 | 4/2003 |
| WO | 03/062192 A1 | 7/2003 |
| WO | 03/062211 A1 | 7/2003 |
| WO | 03/064455 A2 | 8/2003 |
| WO | 03/068244 A1 | 8/2003 |
| WO | 03/093290 A2 | 11/2003 |
| WO | 03/099274 A1 | 12/2003 |
| WO | 2004/000858 A2 | 12/2003 |
| WO | 2004/002422 A2 | 1/2004 |
| WO | 2004/002999 A2 | 1/2004 |
| WO | 2004/003000 A2 | 1/2004 |
| WO | 2004/003138 A2 | 1/2004 |
| WO | 2004/007512 A2 | 1/2004 |
| WO | 2004/011478 A2 | 2/2004 |
| WO | 2004/013300 A2 | 2/2004 |
| WO | 2004/028481 A2 | 4/2004 |
| WO | 2004/041201 A2 | 5/2004 |
| WO | 2004/087714 A1 | 10/2004 |
| WO | 2004/093915 A1 | 11/2004 |
| WO | 2004/103996 A1 | 12/2004 |
| WO | 2004/110442 A1 | 12/2004 |
| WO | 2005/003147 A2 | 1/2005 |
| WO | 2005/016927 A1 | 2/2005 |
| WO | 2005/023819 A1 | 3/2005 |
| WO | 2005/034941 A1 | 4/2005 |
| WO | 2005/046712 A1 | 5/2005 |
| WO | 2005/070955 A1 | 8/2005 |
| WO | 2005/080399 A1 | 9/2005 |
| WO | 2006/008556 A1 | 1/2006 |
| WO | 2006/020082 A1 | 2/2006 |
| WO | 2006/021341 A1 | 3/2006 |
| WO | 2006/027628 A2 | 3/2006 |
| WO | 2006/029912 A1 | 3/2006 |
| WO | 2006/046030 A1 | 5/2006 |
| WO | 2006/046039 A2 | 5/2006 |
| WO | 2006/102087 A2 | 9/2006 |
| WO | 2006/119061 A2 | 11/2006 |
| WO | 2006/119975 A1 | 11/2006 |
| WO | 2007/015787 A1 | 2/2007 |
| WO | 2007/015855 A1 | 2/2007 |
| WO | 2007/016441 A1 | 2/2007 |
| WO | 2007/028789 A1 | 3/2007 |
| WO | 2007/029029 A2 | 3/2007 |
| WO | 2007/131966 A1 | 11/2007 |
| WO | 2007/145894 A2 | 12/2007 |
| WO | 2007/148135 A1 | 12/2007 |
| WO | 2008/051475 A2 | 5/2008 |
| WO | 2008/051477 A2 | 5/2008 |
| WO | 2008/051514 A2 | 5/2008 |
| WO | 2008/057028 A1 | 5/2008 |
| WO | 2008/057208 A2 | 5/2008 |
| WO | 2008/057209 A1 | 5/2008 |
| WO | 2008/112108 A1 | 9/2008 |
| WO | 2009/005687 A1 | 1/2009 |
| WO | 2009/010804 A1 | 1/2009 |
| WO | 2009/064955 A1 | 5/2009 |
| WO | 2009/064975 A1 | 5/2009 |

OTHER PUBLICATIONS

Supplemental European Search Report and Opinion in European Application No. 07852883.3, May 17, 2011.
PCT Search Report in International Application No. PCT/US2007/022419, issued on Apr. 28, 2009.
Brian W. Dymock et al., "Novel Approaches to the Treatment of Hepatitis C Virus Infection," 11 Antiviral Chemistry & Chemotherapy 79-96 (2000).
Hugo R. Rosen & David R. Gretch, "Hepatitis C virus: current understanding and prospects for future therapies," 5 Molec. Med. Today 393-99 (1999).
Darius Moradpour & Hubert E. Blum, "Current and evolving therapies for hepatitis C," 11 Euro. J. Gastroenterol. Hepatol. 1189-1202 (1999).
Ralf Bartenschlager, "Candidate Targets for Hepatitis C Virus-Specific Antiviral Therapy," 40(5-6) Intervirology 378-93 (1997).
Georg M. Lauer & Bruce D. Walker, "Hepatitis C Virus Infection," 345(1) N. Engl. J. Med. 41-52 (2001); correction: 345 (19) N. Engl. J. Med. 1425-26 (2001).
Brain W. Dymock, "Emerging therapies for hepatitis C virus infection," 6 Emerging Drugs 13-42 (2001).
Charlene Crabb, Infectious Diseases. "Hard-Won Advances Spark Excitement about Hepatitis C," Science 506-507 (2001).
Rogers E. Harry-O'Kuru et al., "A Short, Flexible Route toward 2'-C-Branched Ribonucleosides," 62 J. Org. Chem. 1754-59 (1997).
Michael S. Wolfe & Rogers E. Harry-O'Kuru, "A Concise Synthesis of 2'-C-Methylribonucleosides," 36(42) Tetrahedron Letters 7611-14 (1995).
Scott J. Miller et al., "Application of Ring-Closing Metathesis to the Synthesis of Rigidified Amino Acids and Peptides," 118 J. Am. Chem. Soc. 9606-14 (1996).
Jason S. Kingsbury et al., "A Recyclable Ru-Based Metathesis Catalyst," 121 J. Am. Chem. Soc. 791-99 (1999).
Matthias Scholl et al., "Synthesis and Activity of a New Generation of Ruthenium-Based Olefin Metathesis Catalysts Coordinated with 1,3-Dimesityl-4,5-dihydroimidazol-2-ylidene Ligands," 1(6) Organic Letters 953-56 (1999).
Alois Furstner et al., "Total Synthesis and Structural Refinement of the Cyclic Tripyrrole Pigment Nonylprodigiosin," 64 J. Org. Chem. 8275-80 (1999).
Tina M. Trnka & Robert H. Grubbs, "The Development of L2X2R-CHR Olefin Metathesis Catalysts: An Organometallic Success Story," 34 Acc. Chem. Res. 18-29 (2001).
A. Srikrishna et al., "Enantiospecific Construction of the BC-ring System of Taxanes," 45 Tetrahedron Letters 2939-42 (2004).
Yung-Son Hon et al., "Dibromomethane as one-carbon source in organic synthesis: a versatile methodology to prepare the cyclic and acyclic alpha-methylene or alpha-keto acid derivatives from the corresponding terminal alkenes," 60 Tetrahedron 4837-60 (2004).
Eusebio Juaristi & Hugo A. Jimenez-Vazquez, "Single Electron Transfer Mechanism in the Reaction of 1,3-Dithianyllithium and Alkyl Iodides," 56 J. Org. Chem. 1623-30 (1991).
Paola Conti et al., "Chemoenzymatic Synthesis of the Enantiomers of Desoxymuscarine," 9 Tetrahedron: Asymmetry 657-65 (1998).
Robert M. Coates & Mark W. Johnson, "Stereoselective Synthesis of Moenocinol and Assignment of Its Carbon-13 Nuclear Magnetic Resonance Spectrum," 45 J. Org. Chem. 2685-97 (1980).
D. Becker & N. Haddad, "Steric Effects in Intramolecular [2+2] Photocycloaddition of C=C Double Bonds to Cyclohexenones," 49(4) Tetrahedron 947-64 (1993).

Richard A. Bunce et al., "Tandem SN2-Michael Reactions for the Preparation of Simple Five- and Six-Membered-Ring Nitrogen and Sulfur Heterocycles," 57 J. Org. Chem. 1727-33 (1992).

Masao Tokuda et al., "Aminyl Radical Cyclization by Means of Anodic Oxidation. Stereoselective Synthesis of cis-1-Methyl-2,5-Disubstituted Pyrrolidines," 26(49) Tetrahedron Letters 6085-88 (1985).

Robert Haner et al., "174. Generation and Reactions of Lithiated tert-Butyl and 2,6-Di(tert-butyl)-4-methylphenyl Cyclopropanecarboxylates," 69 Helvetica Chimica Acta 1655-65 (1986).

Herbert O. House et al., "Cyclization of Unsaturated Hydroxylamine Derivatives," 41(5) J. Org. Chem. 855-63 (1976).

Theophil Eicher et al., "Bryophyte Constituents; 7: New Synthesis of (+)-Rosmarinic Acid and Related Compounds," Synthesis 755-62 (Jun. 1996).

Michael C. Venuti et al., "Inhibitors of Cyclic AMP Phosphodiesterase. 3. Synthesis and Biological Evaluation of Pyrido and Imidazolyl Analogues of 1,2,3,5-Tetrahydro-2-oxoimidazo[2,1-b]quinazoline," 31 J. Med. Chem. 2136-45 (1988).

Marc-Andre Poupart et al., "Solid-Phase Synthesis of Peptidomimetic Inhibitors for the Hepatitis C Virus NS3 Protease," 66(14) J. Org. Chem. 4743-51 (2001).

Nigel J. Liverton et al., Molecular Modeling Based Approach to Potent P2-P4 Macrocyclic Inhibitors of Hepatitis C NS3/NS4A Protease, 130 J. Am. Chem. Soc. 4607-09 (2008).

Anthony C. Allison & Elsie M. Eugui, "Immunosuppressive and other anti-rheumatic activities of mycophenolate mofetil," 44 Agents and Actions Supplements 165-88 (1993).

Joel Kirschbaum, "Amantadine," 12 Profiles of Drug Substances, Excipients and Related Methodology 1-36 (1983).

T. K. K Chakaborty et al., "Alpha-Phenylglycinol as chiral auxilliary in diastereoselective Strecker synthesis of alpha-amino acids," 51(33) Tetrahedron 9179-90 (1995).

W. Clark Still et al., "Rapid Chromatographic Technique for Preparative Separations with Moderate Resolution," 43(14) J. Org. Chem. 2923-25 (1978).

Michael D. Cooke et al., :The occurrence of a hydride shift in the aromatization of 1,4-epoxy-1,2-dihydronaphthalenes, 11 J. Chem. Soc. Perkin Trans. I: Phys. Org. Chem. 1377 (1984).

Paul Aeberli et al., "Neuropharmacological investigation of N-benzylsulfamides," 10(4) J. Med. Chem. 636-42 (1967).

Nathalie Goudreau & Montse Llinas-Brunet, "The Therapeutic Potential of NS3 Protease Inhibitors in HCV Infection," 14(9) Expert Opinion 1129-44 (2005).

Volker Lohmann et al., "Selective Stimulation of Hepatitis C Virus and Pestivirus NS5B RNA Polymerase Activity by GTP," 274(16) J. Bio. Chem. 10807-15 (1999).

V. Lohmann et al., "Replication of Subgenomic Hepatitis C Virus RNAs in a Hepatoma Cell Line," 285 Science 110-13 (1999).

Kevin X. Chen et al. "Novel Potent Hepatitis C Virus NS3 Serine Protease Inhibitors Derived from Proline-Based Macrocycles," 49 J. Med. Chem. 995-1005 (2006).

Yuri Goldberg et al., "Highly regioselective bromination of 2,3-dimethylanisole with N-bromosuccinimide," 57 J. Org. Chem. 6374-76 (1992).

Manfred Schlosser et al., "8-Methoxyisoquinoline derivatives through ortho-selective metallation of 2-(3-methoxyphenyl)ethylamines," 32(17) Tetrahedron Letters 1965-66 (1991).

Angela Casini et al., "Carbonic Anhydrase inhibitors inhibition of cytosolic isozymes I and II with sulfamide derivatives," 13(5) Bioorg. Med. Chem. Lett. 837-40 (2003).

Kiyotaka Onisuka et al., "A novel route to 2,3-disubstituted indoles via palladium-catalyzed three-component coupling of aryl iodide, o-alkenylphenyl isocyanide and amine," 43 Tetrahedron Letters 6197-99 (2002).

Duane E. Rudisill & J. K. Stille, "Palladium-catalyzed synthesis of 2-substituted indoles," 54(25) J. Org. Chem. 5856-66 (2002).

Makoto Satoh et al., "Palladium-Catalyzed Cross-Coupling Reaction of (1-Ethoxy-1-alken-2-yl)boranes With orthoFunctionalized Iodoarenes. A Novel and Convenient Synthesis of Benzo-Fused Heteroaromatic Compounds," Synthesis Communications 373-377 (Apr. 1987).

Yuusaku Yokoyama et al., "Palladium-Catalyzed Reaction of 3-Bromoindole Derivative with Allyl Esters in the Presence of Hexa-n-butyldistannane," 31(8) Heterocycles 1505-11 (1990).

Steven W. Ludmerer et al., "A transient cell-based phenotype assay for hepatitis C NS3/4A protease: Application to potency determinations of a novel macrocyclic inhibitor against diverse protease sequences isolated from plasma infected with HCV," 151 Journal of Virological Methods 301-07 (2008).

John A. McCauley et al., "Bismacrocyclic Inhibitors of Hepatitis C NS3/4a Protease," 47 Angew. Chem. Int. Ed. 9104-07 (2008).

Ashok Arasappan et al., "P2-P4 Macrocyclic inhibitors of hepatitis C virus NS3-4A serine protease," 16 Bioorganic & Medicinal Chemistry Letters 3960-65 (2006).

* cited by examiner

HCV NS3 PROTEASE INHIBITORS

CROSS-REFERENCE TO RELATED APPLICATIONS

This application is a National Stage application of International Patent Application No. PCT/US2007/022419, filed Oct. 22, 2007. This application also claims priority to U.S. Provisional Patent Application No. 60/853,964, filed Oct. 24, 2006.

FIELD OF THE INVENTION

The present invention relates to macrocyclic compounds that are useful as inhibitors of the hepatitis C virus (HCV) NS3 protease, their synthesis, and their use for treating or preventing HCV infection.

BACKGROUND OF THE INVENTION

Hepatitis C virus (HCV) infection is a major health problem that leads to chronic liver disease, such as cirrhosis and hepatocellular carcinoma, in a substantial number of infected individuals, estimated to be 2-15% of the world's population. There are an estimated 3.9 million infected people in the United States alone, according to the U.S. Center for Disease Control, roughly five times the number of people infected with the human immunodeficiency virus (HIV). According to the World Health Organization, there are more than 170 million infected individuals worldwide, with at least 3 to 4 million people being infected each year. Once infected, about 20% of people clear the virus, but the rest harbor HCV the rest of their lives. Ten to twenty percent of chronically infected individuals eventually develop liver-destroying cirrhosis or cancer. The viral disease is transmitted sexually, parenterally by contaminated blood and blood products, contaminated needles, and vertically from infected mothers or carrier mothers to their off-spring.

Current treatments for HCV infection, which are restricted to immunotherapy with recombinant interferon-α alone or in combination with the nucleoside analog ribavirin, are of limited clinical benefit. Moreover, there is no established vaccine for HCV. Consequently, there is an urgent need for improved therapeutic agents that effectively combat chronic HCV infection. The current state of the art in the treatment of HCV infection has been discussed in the following references: B. Dymock, et al., "Novel approaches to the treatment of hepatitis C virus infection," *Antiviral Chemistry & Chemotherapy*, 11: 79-96 (2000); H. Rosen, et al., "Hepatitis C virus: current understanding and prospects for future therapies," *Molecular Medicine Today*, 5: 393-399 (1999); D. Moradpour, et al., "Current and evolving therapies for hepatitis C," *European J. Gastroenterol. Hepatol.*, 11: 1189-1202 (1999); R. Bartenschlager, "Candidate Targets for Hepatitis C Virus-Specific Antiviral Therapy," *Intervirology*, 40: 378-393 (1997); G. M. Lauer and B. D. Walker, "Hepatitis C Virus Infection," *N. Engl. J. Med.*, 345: 41-52 (2001); B. W. Dymock, "Emerging therapies for hepatitis C virus infection," *Emerging Drugs*, 6: 13-42 (2001); and C. Crabb, "Hard-Won Advances Spark Excitement about Hepatitis C," *Science:* 506-507 (2001).

Several virally-encoded enzymes are putative targets for therapeutic intervention, including a metalloprotease (NS2-3), a serine protease (NS3), a helicase (NS3), and an RNA-dependent RNA polymerase (NS5B). The NS3 protease is located in the N-terminal domain of the NS3 protein, and is considered a prime drug target since it is responsible for an intramolecular cleavage at the NS3/4A site and for downstream intermolecular processing at the NS4A/4B, NS4B/5A and NS5A/5B junctions. NS4A is a cofactor for NS3 protease activity. Previous research has identified classes of peptides, such as hexapeptides as well as tripeptides discussed in U.S. patent applications US 2005/0020503, US 2004/0229818, and US 2004/00229776, showing degrees of activity in inhibiting the NS3 protease. The aim of the present invention is to provide further compounds which exhibit activity against the HCV NS3 protease.

SUMMARY OF THE INVENTION

The present invention relates to novel macrocyclic compounds of formula (I) or pharmaceutically acceptable salts or hydrates or prodrugs thereof. These compounds are useful in the inhibition of HCV (hepatitis C virus) NS3 (non-structural 3) protease, the prevention or treatment of one or more of the symptoms of HCV infection, either as compounds or their pharmaceutically acceptable salts or hydrates (when appropriate), or as pharmaceutical composition ingredients, whether or not in combination with other HCV antivirals, anti-infectives, immunomodulators, antibiotics or vaccines. More particularly, the present invention relates to a compound of formula (I)

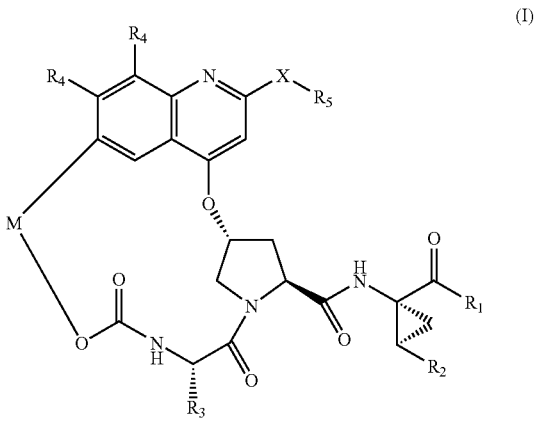

or a pharmaceutically acceptable salt, hydrate or prodrug thereof, wherein:

$R_1$ is OH, $NHSO_2R_6$, $NHSO_2NR_8R_9$, or $NHP(O)R_{11}R_{12}$;

$R_2$ is $C_1$-$C_4$ alkyl or $C_2$-$C_4$ alkenyl, wherein the alkyl or alkenyl is substituted with 0 to 3 halo;

$R_3$ is $C_1$-$C_8$ alkyl, $C_3$-$C_8$ cycloalkyl($C_1$-$C_8$)alkyl, aryl($C_1$-$C_8$)alkyl, Het, or $C_3$-$C_8$ cycloalkyl, wherein aryl is phenyl or naphthyl, and each alkyl, cycloalkyl, or aryl is substituted with 0 to 3 substituents selected from the group consisting of halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

Het is a 5- to 6-membered saturated cyclic ring having 1 or 2 heteroatoms selected from N, O and S, wherein the ring is substituted with 0 to 3 substituents selected from halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

each $R_4$ is independently H, $C_1$-$C_6$ alkyl, halogen or $OR_{10}$;

$R_5$ is $C_1$-$C_8$ alkyl, aryl, heteroaryl, heterocyclyl, $C_3$-$C_8$ cycloalkyl, $C_1$-$C_6$ haloalkyl or $C_1$-$C_6$ thioalkyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein the aryl, heteroaryl, heterocyclyl, cycloalkyl or alkyl is substituted with 0 to 4 substituents selected from the group consisting of halo, $OR_{10}$, $SR_{10}$, $N(R_7)_2$, $C_1$-$C_6$ alkyl, aryl, heteroaryl, heterocyclyl, $C_1$-$C_6$ haloalkyl, $C_3$-$C_6$ cycloalkyl, cycloalkoxy, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$, and wherein the heteroaryl or heterocyclyl substituent is unsubstituted or substituted with $C_1$-$C_6$ alkyl or aryl;

each $R_6$ is independently $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is substituted with 0 to 2 W substituents or $P(O)R_{11}R_{12}$, and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

W is H, halo, $OR_{10}$, $C_1$-$C_6$ alkyl, CN, $CF_3$, $SR_{10}$, $SO_2(C_1$-$C_6$ alkyl), $C_3$-$C_8$ cycloalkyl, $C_3$-$C_8$ cycloalkoxy, $C_1$-$C_6$ haloalkyl, or $N(R_7)_2$;

each $R_7$ is independently H, $C_1$-$C_6$ alkyl or $C_3$-$C_6$ cycloalkyl;

X is O, NH, $N(CH_3)$, $N(C(O)CH_3)$, $N(C(O)OCH_2CH_3)$, $CH_2$ or S;

or X—$R_5$ is a heterocyclyl ring wherein the point of attachment is the heteroatom;

M is $C_1$-$C_8$ alkylene, $C_2$-$C_8$ alkenylene or ($C_1$-$C_8$ alkylene)-O—($C_1$-$C_8$ alkylene), wherein the $C_1$-$C_8$ alkylene, $C_2$-$C_8$ alkenylene or ($C_1$-$C_8$ alkylene)-O—($C_1$-$C_8$ alkylene) is substituted with 0 to 4 substituents selected from the group consisting of $C_1$-$C_8$ alkyl, $C_3$-$C_8$ cycloalkyl($C_1$-$C_8$ alkyl), aryl ($C_1$-$C_8$ alkyl), and $N(R_4)_2$; where 2 adjacent substituents of M are optionally taken together to form a 3- to 6-membered cyclic ring;

$R_8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein the alkyl, cycloalkyl, aryl, heteroaryl or heterocyclyl is substituted with 0 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR_{10}$, $SR_{10}$, $N(R_{10})_2$, $N(C_1$-$C_6$ alkyl)O($C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of the cycloalkyl, cycloalkoxy, aryl, heteroaryl or heterocyclyl are optionally taken together to form a 3- to 6-membered cyclic ring containing 0 to 3 heteroatoms selected from N, O and S;

$R_9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein the alkyl, cycloalkyl, alkoxy, cycloalkoxy, aryl, heteroaryl or heterocyclyl is substituted with 0 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR_{10}$, $SR_{10}$, $N(R_{10})_2$, $N(C_1$-$C_6$ alkyl)O($C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R_8$ and $R_9$ are optionally taken together, with the nitrogen atom to which they are attached, to form a 4- to 8-membered monocyclic ring containing 0 to 2 additional heteroatoms selected from N, O and S;

each $R_{10}$ is independently H or $C_1$-$C_6$ alkyl;

each $R_{11}$ is independently $OR_{13}$, $N(R_{10})$—V—$CO_2R_{10}$, O—V—$CO_2R_{10}$, S—V—$CO_2R_{10}$, $N(R_{10})(R_{13})$, $R_{14}$, or $N(R_{10})SO_2R_6$;

each $R_{12}$ is independently $OR_{13}$, $N(R_{10})$—V—$CO_2R_{10}$, O—V—$CO_2R_{10}$, S—V—$CO_2R_{10}$, or $N(R_{10})(R_{13})$;

or $R_{11}$ and $R_{12}$ are optionally taken together, with the phosphorus atom to which they are attached, to form a 5- to 7-membered monocyclic ring;

each V is independently $CH(R_{15})$ or $C_1$-$C_4$ alkylene-CH ($R_{15}$);

each $R_{13}$ is independently H, $C_1$-$C_6$ alkyl, $C_2$-$C_6$ alkenyl, $C_3$-$C_8$ cycloalkyl, aryl, heteroaryl, or heterocyclyl, wherein the alkyl, alkenyl, cycloalkyl, aryl, heteroaryl or heterocyclyl is substituted with 0 to 2 substituents selected from the group consisting of aryl, aryl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of the cycloalkyl, cycloalkoxy, aryl, heteroaryl or heterocyclyl are optionally taken together to form a 3- to 6-membered cyclic ring containing 0 to 3 heteroatoms selected from N, O and S;

$R_{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is substituted with 0 to 2 substituents selected from the group consisting of $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; and each $R_{15}$ is independently $C_1$-$C_6$ alkyl, $C_2$-$C_6$ alkenyl, $C_3$-$C_8$ cycloalkyl, aryl, heteroaryl, or heterocyclyl, wherein the alkyl, alkenyl, cycloalkyl, aryl, heteroaryl or heterocyclyl is substituted with 0 to 2 substituents selected from the group consisting of $C_1$-$C_6$ alkyl, halo, OC(O)O$R_6$, OC(O)$R_6$, O$R_{10}$, S$R_{10}$, N($R_{10}$)$_2$, C(O)$R_{10}$, NO$_2$, CN, CF$_3$, SO$_2$($C_1$-$C_6$ alkyl), S(O)($C_1$-$C_6$ alkyl), N$R_{10}$SO$_2$$R_6$, SO$_2$N($R_6$)$_2$, NHCOO$R_6$, NHCO$R_6$, NHCONH$R_6$, CO$_2$$R_{10}$, and C(O)N($R_{10}$)$_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of the cycloalkyl, cycloalkoxy, aryl, heteroaryl or heterocyclyl are optionally taken together to form a 3- to 6-membered cyclic ring containing 0 to 3 heteroatoms selected from N, O and S.

The present invention also includes pharmaceutical compositions containing a compound of the present invention and methods of preparing such pharmaceutical compositions. The present invention further includes methods of treating or preventing one or more symptoms of HCV infection.

Other embodiments, aspects and features of the present invention are either further described in or will be apparent from the ensuing description, examples and appended claims.

DETAILED DESCRIPTION OF THE INVENTION

The present invention includes compounds of formula (I) above, and pharmaceutically acceptable salts or hydrates thereof. These compounds and their pharmaceutically acceptable salts or hydrates are HCV protease inhibitors (e.g., HCV NS3 protease inhibitors).

In a first embodiment of the compounds of formula (I), $R_1$ is NHSO$_2$$R_6$. In a preferred group of this embodiment, $R_6$ is $C_3$-$C_6$ cycloalkyl. In a more preferred group of this embodiment, $R_6$ is cyclopropyl.

In a second embodiment of the compounds of formula (I), $R_2$ is $C_2$-$C_4$ alkenyl. In a preferred group of this embodiment, $R_2$ is —CH=CH$_2$.

In a third embodiment of the compounds of formula (I), $R_3$ is $C_3$-$C_8$ cycloalkyl. In a preferred group of this embodiment, $R_3$ is cyclohexyl or cyclopentyl.

In a fourth embodiment of the compounds of formula (I), $R_4$ is independently H, chloro, iodo or —O—($C_1$-$C_6$ alkyl). In a preferred group of this embodiment, $R_4$ is independently H, chloro, iodo or —OCH$_3$.

In a fifth embodiment of the compounds of formula (I), X is O, NH or N(CH$_3$).

In a sixth embodiment of the compounds of formula (I), M is $C_1$-$C_8$ alkylene, $C_2$-$C_8$ alkenylene or ($C_1$-$C_8$ alkylene)-O—($C_1$-$C_8$ alkylene), having 0 to 4 substituents selected from the group consisting of $C_1$-$C_8$ alkyl, $C_3$-$C_8$ cycloalkyl($C_1$-$C_8$ alkyl), aryl($C_1$-$C_8$ alkyl), and N($R_4$)$_2$, where 2 adjacent substituents of M are optionally taken together to form a 3- to 6-membered cyclic ring. In a preferred group of this embodiment, M is $C_5$-$C_8$ alkylene, having 0 to 4 substituents selected from the group consisting of $C_1$-$C_8$ alkyl, $C_3$-$C_8$ cycloalkyl ($C_1$-$C_8$ alkyl), aryl($C_1$-$C_8$ alkyl), and N($R_4$)$_2$, where 2 adjacent substituents of M are optionally taken together to form a 3- to 6-membered cyclic ring. In a more preferred group of this embodiment, M is selected from the group consisting of —(CH$_2$)$_3$C(CH$_3$)$_2$CH$_2$—, —CH=CH(CH$_2$)$_5$, —(CH$_2$)$_7$—, —CH$_2$CH=CH(CH$_2$)$_4$—, —(CH$_2$)$_6$—, —CH=CH(CH$_2$)$_4$—, —CH=CH(CH$_2$)$_3$C(CH$_3$)$_2$CH$_2$—, —CH=CH(CH$_2$)$_3$—, —(CH$_2$)$_5$—, —CH=CH(CH$_2$)$_3$—, —(CH$_2$)$_4$—, —(CH$_2$)$_3$—, —CH=CH(CH$_2$)$_2$C(CH$_3$)$_2$CH$_2$—, —(CH$_2$)$_4$C(CH$_3$)$_2$CH$_2$—, —C(=CH$_2$)(CH$_2$)$_5$—, —C(CH$_2$)(CH$_2$)$_3$—, —CH$_2$CH=CH(CH$_2$)$_3$—. In some embodiments, M is selected from the group consisting of

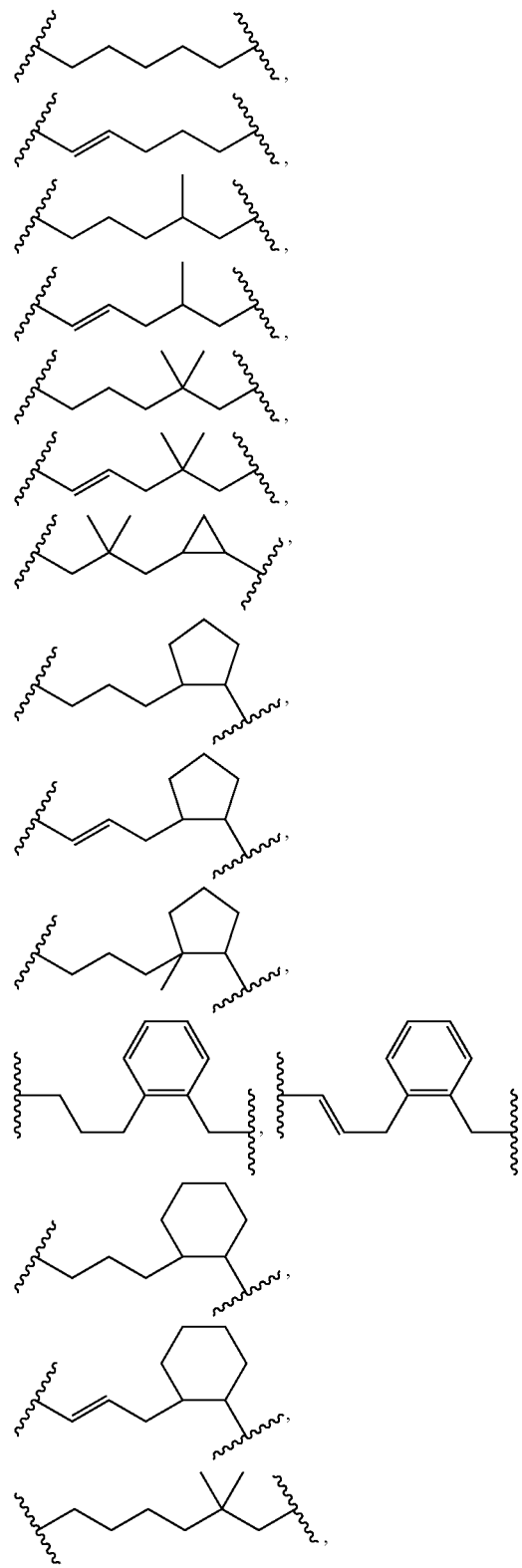

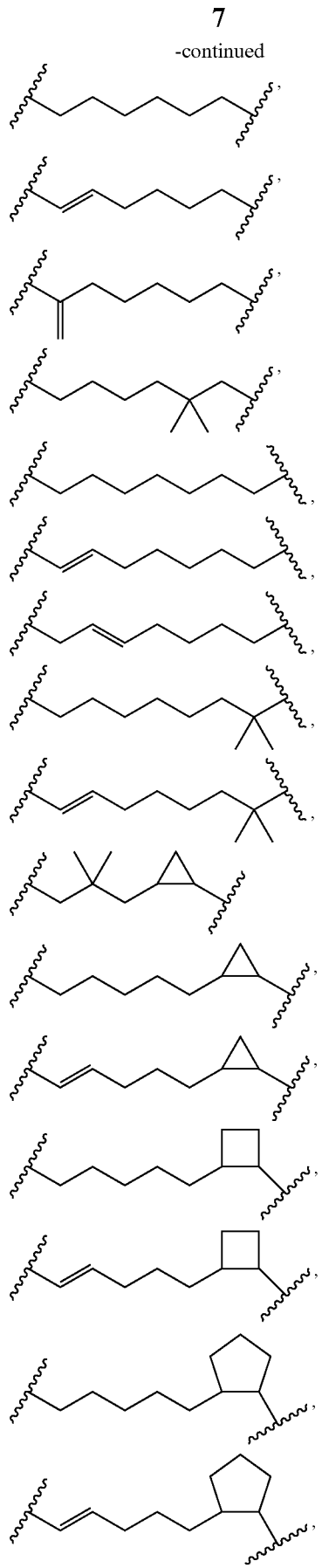

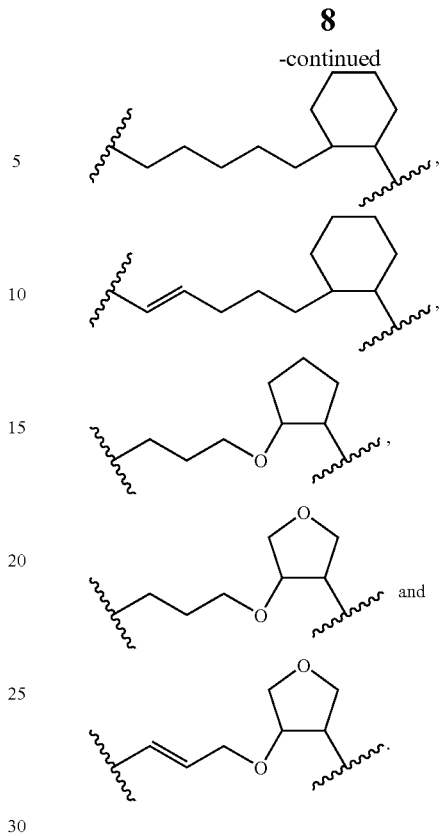

In a seventh embodiment of the compounds of formula (I), $R_5$ is $C_1$-$C_8$ alkyl or $C_3$-$C_8$ cycloalkyl, wherein said alkyl or cycloalkyl is optionally substituted with 1 to 4 substituents selected from the group consisting of aryl, heterocyclyl, or $CF_3$, and wherein said heterocyclyl substituent is unsubstituted or substituted with $CH_3$. In a more preferred group of this embodiment, $R_5$ is $C_1$-$C_5$ alkyl or $C_5$-$C_6$ cycloalkyl, wherein said alkyl or cycloalkyl is optionally substituted with 1 substituent selected from the group consisting of phenyl, thiazolyl, or $CF_3$, and wherein said thiazolyl substituent is unsubstituted or substituted with $CH_3$.

In eighth embodiment of the compounds of formula (I), —X—$R_5$ is a piperidine ring, wherein the point of attachment is a nitrogen atom.

Further embodiments of the compounds of formula (I) provide a combination of some or all of the above-described first through eighth embodiments, including the combination of any subset of embodiments.

Another embodiment of the present invention is a compound, or a pharmaceutically acceptable salt, hydrate or prodrug thereof, selected from the group consisting of the compounds set forth in Examples 1-16.

Other embodiments of the present invention include the following:

(a) A pharmaceutical composition comprising an effective amount of a compound of formula (I) and a pharmaceutically acceptable carrier.

(b) The pharmaceutical composition of (a), further comprising a second therapeutic agent selected from the group consisting of a HCV antiviral agent, an immunomodulator, and an anti-infective agent.

(c) The pharmaceutical composition of (b), wherein the HCV antiviral agent is an antiviral selected from the group consisting of a HCV protease inhibitor and a HCV NS5B polymerase inhibitor.

(d) A pharmaceutical combination which is (i) a compound of formula (I) and (ii) a second therapeutic agent selected from the group consisting of a HCV antiviral agent, an immunomodulator, and an anti-infective agent; wherein the compound of formula (I) and the second therapeutic agent are each employed in an amount that renders the combination effective for inhibiting HCV NS3 protease, or for treating or preventing infection by HCV.

(e) The combination of (d), wherein the HCV antiviral agent is an antiviral selected from the group consisting of a HCV protease inhibitor and a HCV NS5B polymerase inhibitor.

(f) A method of inhibiting HCV NS3 protease in a subject in need thereof which comprises administering to the subject an effective amount of a compound of formula (I).

(g) A method of preventing or treating infection by HCV in a subject in need thereof which comprises administering to the subject an effective amount of a compound of formula (I).

(h) The method of (g), wherein the compound of formula (I) is administered in combination with an effective amount of at least one second therapeutic agent selected from the group consisting of a HCV antiviral agent, an immunomodulator, and an anti-infective agent.

(i) The method of (h), wherein the HCV antiviral agent is an antiviral selected from the group consisting of a HCV protease inhibitor and a HCV NS5B polymerase inhibitor.

(j) A method of inhibiting HCV NS3 protease in a subject in need thereof which comprises administering to the subject the pharmaceutical composition of (a), (b), or (c) or the combination of (d) or (e).

(k) A method of preventing or treating infection by HCV in a subject in need thereof which comprises administering to the subject the pharmaceutical composition of (a), (b), or (c) or the combination of (d) or (e).

The present invention also includes a compound of the present invention (i) for use in, (ii) for use as a medicament for, or (iii) for use in the preparation of a medicament for: (a) inhibiting HCV NS3 protease, or (b) treating HCV infection and/or reducing the likelihood or severity of symptoms of HCV infection. In these uses, the compounds of the present invention can optionally be employed in combination with one or more second therapeutic agents selected from HCV antiviral agents, anti-infective agents, and immunomodulators.

Additional embodiments of the invention include the pharmaceutical compositions, combinations and methods set forth in (a)-(k) above and the uses set forth in the preceding paragraph, wherein the compound of the present invention employed therein is a compound of one of the embodiments, aspects, classes, sub-classes, or features of the compounds described above. In all of these embodiments, the compound may optionally be used in the form of a pharmaceutically acceptable salt or hydrate as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (k) above are understood to include all embodiments of the compounds, including such embodiments as result from combinations of embodiments.

As used herein, all ranges are inclusive, and all sub-ranges are included within such ranges, although not necessarily explicitly set forth. For example, a heteroaryl ring described as containing from "1 to 3 heteroatoms" means the ring can contain 1, 2, or 3 heteroatoms. In addition, the term "or," as used herein, denotes alternatives that may, where appropriate, be combined; that is, the term "or" includes each listed alternative separately as well as their combination.

As used herein, the term "alkyl" refers to any linear or branched chain alkyl group having a number of carbon atoms in the specified range. Thus, for example, "$C_{1-6}$ alkyl" (or "$C_1$-$C_6$ alkyl") refers to all of the hexyl alkyl and pentyl alkyl isomers as well as n-, iso-, sec- and t-butyl, n- and isopropyl, ethyl and methyl. As another example, "$C_{1-4}$ alkyl" refers to n-, iso-, sec- and t-butyl, n- and isopropyl, ethyl and methyl. Alkyl groups may be substituted as indicated.

The term "halogenated" refers to a group or molecule in which a hydrogen atom has been replaced by a halogen. Similarly, the term "haloalkyl" refers to a halogenated alkyl group. The term "halogen" (or "halo") refers to atoms of fluorine, chlorine, bromine and iodine (alternatively referred to as fluoro, chloro, bromo, and iodo).

The term "alkoxy" refers to an "alkyl-O—" group. Alkoxy groups may be substituted as indicated.

The term "alkylene" refers to any linear or branched chain alkylene group (or alternatively "alkanediyl") having a number of carbon atoms in the specified range. Thus, for example, "—$C_{1-6}$ alkylene-" refers to any of the $C_1$ to $C_6$ linear or branched alkylenes. A class of alkylenes of particular interest with respect to the invention is —$(CH_2)_{1-6}$—, and sub-classes of particular interest include —$(CH_2)_{1-4}$—, —$(CH_2)_{1-3}$—, —$(CH_2)_{1-2}$—, and —$CH_2$—. Also of interest is the alkylene —$CH(CH_3)$—. Alkylene groups may be substituted as indicated.

The term "cycloalkyl" refers to any cyclic ring of an alkane or alkene having a number of carbon atoms in the specified range. Thus, for example, "$C_{3-8}$ cycloalkyl" (or "$C_3$-$C_8$ cycloalkyl") refers to cyclopropyl, cyclobutyl, cyclopentyl, cyclohexyl, cycloheptyl, and cyclooctyl. The term "cycloalkoxy" refers to a "—O-cycloalkyl" group. Cycloalkyl groups may be substituted as indicated.

The term "aryl" refers to aromatic mono- and poly-carbocyclic ring systems, also referred to as "arenes," wherein the individual carbocyclic rings in the polyring systems are fused or attached to each other via a single bond. Suitable aryl groups include phenyl, naphthyl, and biphenylenyl. Aryl groups may be substituted as indicated.

Unless indicated otherwise, the term "heterocycle" (and variations thereof such as "heterocyclic" or "heterocyclyl") broadly refers to (i) a stable 4- to 8-membered, saturated or unsaturated monocyclic ring, (ii) a stable 7- to 12-membered bicyclic ring system, or (iii) a stable 11- to 15-membered tricyclic ring system, wherein each ring in (ii) and (iii) is independent of, or fused to, the other ring or rings and each ring is saturated or unsaturated, and the monocyclic ring, bicyclic ring system or tricyclic ring system contains one or more heteroatoms (e.g., from 1 to 6 heteroatoms, or from 1 to 4 heteroatoms) independently selected from N, O and S and a balance of carbon atoms (the monocyclic ring typically contains at least one carbon atom and the bicyclic and tricyclic ring systems typically contain at least two carbon atoms); and wherein any one or more of the nitrogen and sulfur heteroatoms is optionally oxidized, and any one or more of the nitrogen heteroatoms is optionally quaternized. Unless otherwise specified, the heterocyclic ring may be attached at any heteroatom or carbon atom, provided that attachment results in the creation of a stable structure. Heterocycle groups may be substituted as indicated, and unless otherwise specified, the substituents may be attached to any atom in the ring, whether a heteroatom or a carbon atom, provided that a stable chemical structure results.

Saturated heterocyclics form a subset of the heterocycles. Unless expressly stated to the contrary, the term "saturated heterocyclic" generally refers to a heterocycle as defined above in which the entire ring system (whether mono- or poly-cyclic) is saturated. The term "saturated heterocyclic ring" refers to a 4- to 8-membered saturated monocyclic ring, a stable 7- to 12-membered bicyclic ring system, or a stable 11- to 15-membered tricyclic ring system, which consists of carbon atoms and one or more heteroatoms independently selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Unsaturated heterocyclics form another subset of the heterocycles. Unless expressly stated to the contrary, the term "unsaturated heterocyclic" generally refers to a heterocycle as defined above in which the entire ring system (whether mono- or poly-cyclic) is not saturated, i.e., such rings are either unsaturated or partially unsaturated. Unless expressly stated to the contrary, the terms "heteroaromatic ring" or "heteroaryl" refer a stable 5- or 6-membered monocyclic aromatic ring, a stable 7- to 12-membered bicyclic ring system, or a stable 11- to 15-membered tricyclic ring system, which consists of carbon atoms and one or more heteroatoms selected from N, O and S. In the case of substituted heteroaromatic rings containing at least one nitrogen atom (e.g., pyridine), such substitutions can be those resulting in N-oxide formation. Representative examples of heteroaromatic rings include pyridyl, pyrrolyl, pyrazinyl, pyrimidinyl, pyridazinyl, thienyl (or thiophenyl), thiazolyl, furanyl, imidazolyl, pyrazolyl, triazolyl, tetrazolyl, oxazolyl, isooxazolyl, oxadiazolyl, thiazolyl, isothiazolyl, and thiadiazolyl.

Representative examples of bicyclic heterocycles include benzotriazolyl, indolyl, isoindolyl, indazolyl, indolinyl, isoindolinyl, quinoxalinyl, quinazolinyl, cinnolinyl, chromanyl, isochromanyl, tetrahydroquinolinyl, quinolinyl, tetrahydroisoquinolinyl, isoquinolinyl, 2,3-dihydrobenzofuranyl, 2,3-dihydrobenzo-1,4-dioxinyl (i.e.,

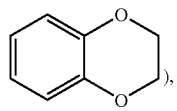

imidazo(2,1-b)(1,3)thiazole, (i.e.,

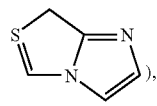

and benzo-1,3-dioxolyl (i.e.,

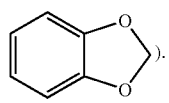

In certain contexts herein,

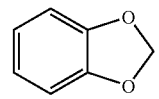

is alternatively referred to as phenyl having as a substituent methylenedioxy attached to two adjacent carbon atoms.

Unless otherwise specifically noted as only "unsubstituted" or only "substituted", alkyl, cycloalkyl, aryl and heterocycle groups are unsubstituted or substituted. As used herein, the terms "substituted alkyl", "substituted $C_3$-$C_{10}$ cycloalkyl", "substituted aryl" and "substituted heterocycle" are intended to include the cyclic group containing from 1 to 3 substituents in addition to the point of attachment to the rest of the compound. Preferably, the substituents are selected from the group which includes, but is not limited to, halo, $C_1$-$C_{20}$ alkyl, —$CF_3$, —$NH_2$, —$N(C_1$-$C_6$ alkyl$)_2$, —$NO_2$, oxo, —CN, —$N_3$, —OH, —O($C_1$-$C_6$ alkyl), $C_3$-$C_{10}$ cycloalkyl, $C_2$-$C_6$ alkenyl, $C_2$-$C_6$ alkynyl, ($C_0$-$C_6$ alkyl) S(O)$_{0-2}$—, aryl-S(O)$_{0-2}$—, ($C_0$-$C_6$ alkyl)S(O)$_{0-2}$($C_0$-$C_6$ alkyl)-, ($C_0$-$C_6$ alkyl)C(O)NH—, $H_2$N—C(NH)—, —O($C_1$-$C_6$ alkyl)$CF_3$, ($C_0$-$C_6$ alkyl)C(O)—, ($C_0$-$C_6$ alkyl)OC(O)—, ($C_0$-$C_6$alkyl)O($C_1$-$C_6$ alkyl)-, ($C_0$-$C_6$ alkyl)C(O)$_{1-2}$($C_0$-$C_6$ alkyl)-, ($C_0$-$C_6$ alkyl)OC(O)NH—, aryl, aralkyl, heteroaryl, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl.

When any variable (e.g., $R^7$ and $R^{10}$) occurs more than one time in any constituent or in formula (I) or in any other formula depicting and describing compounds of the invention, its definition on each occurrence is independent of its definition at every other occurrence. Also, combinations of substituents and/or variables are permissible only if such combinations result in stable compounds.

Unless expressly stated to the contrary, substitution by a named substituent is permitted on any atom in a ring (e.g., aryl, a heteroaromatic ring, or a saturated heterocyclic ring) provided such ring substitution is chemically allowed and results in a stable compound. A "stable" compound is a compound which can be prepared and isolated and whose structure and properties remain or can be caused to remain essentially unchanged for a period of time sufficient to allow use of the compound for the purposes described herein (e.g., therapeutic or prophylactic administration to a subject).

As a result of the selection of substituents and substituent patterns, certain of the compounds of the present invention can have asymmetric centers and can occur as mixtures of stereoisomers, or as individual diastereomers, or enantiomers. All isomeric forms of these compounds, whether isolated or in mixtures, are within the scope of the present invention.

As would be recognized by one of ordinary skill in the art, certain of the compounds of the present invention can exist as tautomers. For the purposes of the present invention a reference to a compound of formula (I) is a reference to the compound per se, or to any one of its tautomers per se, or to mixtures of two or more tautomers.

The compounds of the present inventions are useful in the inhibition of HCV protease (e.g., HCV NS3 protease) and the treatment of HCV infection and/or reduction of the likelihood or severity of symptoms of HCV infection. For example, the compounds of this invention are useful in treating infection by HCV after suspected past exposure to HCV by such means as blood transfusion, exchange of body fluids, bites, accidental needle stick, or exposure to patient blood during surgery.

The compounds of this invention are useful in the preparation and execution of screening assays for antiviral compounds. For example, the compounds of this invention are useful for isolating enzyme mutants, which are excellent screening tools for more powerful antiviral compounds. Furthermore, the compounds of this invention are useful in establishing or determining the binding site of other antivirals to HCV protease, e.g., by competitive inhibition. Thus, the compounds of this invention may be commercial products to be sold for these purposes.

The compounds of the present invention may be administered in the form of pharmaceutically acceptable salts. The term "pharmaceutically acceptable salt" refers to a salt which possesses the effectiveness of the parent compound and which is not biologically or otherwise undesirable (e.g., is neither toxic nor otherwise deleterious to the recipient thereof). Suitable salts include acid addition salts which may, for example, be formed by mixing a solution of the compound of the present invention with a solution of a pharmaceutically acceptable acid such as hydrochloric acid, sulfuric acid, acetic acid, trifluoroacetic acid, or benzoic acid. Many of the compounds of the invention carry an acidic moiety, in which case suitable pharmaceutically acceptable salts thereof can include alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

The term "administration" and variants thereof (e.g., "administering" a compound) in reference to a compound of the invention mean providing the compound or a prodrug of the compound to the individual in need of treatment. When a compound of the invention or a prodrug thereof is provided in combination with one or more other active agents (e.g., antiviral agents useful for treating HCV infection), "administration" and its variants are each understood to include concurrent and sequential provision of the compound or salt (or hydrate) and other agents.

As used herein, the term "prodrug" is intended to encompass an inactive drug form or compound that is converted into an active drug form or compound by the action of enzymes, chemicals or metabolic processes in the body of an individual to whom it is administered.

As used herein, the term "composition" is intended to encompass a product comprising the specified ingredients, as well as any product which results, directly or indirectly, from combining the specified ingredients.

By "pharmaceutically acceptable" is meant that the ingredients of the pharmaceutical composition must be compatible with each other and not deleterious to the recipient thereof.

The term "subject" (alternatively referred to herein as "patient") as used herein refers to an animal, preferably a mammal, most preferably a human, who has been the object of treatment, observation or experiment.

The term "effective amount" as used herein means that amount of active compound or pharmaceutical agent that elicits the biological or medicinal response in a tissue, system, animal or human that is being sought by a researcher, veterinarian, medical doctor or other clinician. In one embodiment, the effective amount is a "therapeutically effective amount" for the alleviation of one or more symptoms of the disease or condition being treated. In another embodiment, the effective amount is a "prophylactically effective amount" for reduction of the severity, likelihood or occurrence of one or more symptoms of the disease or condition. The term also includes herein the amount of active compound sufficient to inhibit HCV NS3 protease and thereby elicit the response being sought (i.e., an "inhibition effective amount"). When the active compound (i.e., active ingredient) is administered as the salt, references to the amount of active ingredient are to the free acid or free base form of the compound.

For the purpose of inhibiting HCV NS3 protease and treating HCV infection and/or reducing the likelihood or severity of symptoms of HCV infection, the compounds of the present invention, optionally in the form of a salt or a hydrate, can be administered by any means that produces contact of the active agent with the agent's site of action. They can be administered by any conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice. The compounds of the invention can, for example, be administered orally, parenterally (including subcutaneous injections, intravenous, intramuscular, intrasternal injection or infusion techniques), by inhalation (such as in a spray form), or rectally, in the form of a unit dosage of a pharmaceutical composition containing an effective amount of the compound and conventional non-toxic pharmaceutically-acceptable carriers, adjuvants and vehicles. Liquid preparations suitable for oral administration (e.g., suspensions, syrups, elixirs and the like) can be prepared according to techniques known in the art and can employ any of the usual media such as water, glycols, oils, alcohols and the like. Solid preparations suitable for oral administration (e.g., powders, pills, capsules and tablets) can be prepared according to techniques known in the art and can employ such solid excipients as starches, sugars, kaolin, lubricants, binders, disintegrating agents and the like. Parenteral compositions can be prepared according to techniques known in the art and typically employ sterile water as a carrier and optionally other ingredients, such as solubility aids. Injectable solutions can be prepared according to methods known in the art wherein the carrier comprises a saline solution, a glucose solution or a solution containing a mixture of saline and glucose. Further description of methods suitable for use in preparing pharmaceutical compositions of the present invention and of ingredients suitable for use in said compositions is provided in *Remington's Pharmaceutical Sciences*, 18$^{th}$ edition (ed. A. R. Gennaro, Mack Publishing Co., 1990).

The compounds of this invention can be administered orally in a dosage range of 0.001 to 1000 mg/kg of mammal (e.g., human) body weight per day in a single dose or in divided doses. One dosage range is 0.01 to 500 mg/kg body weight per day orally in a single dose or in divided doses. Another dosage range is 0.1 to 100 mg/kg body weight per day orally in single or divided doses. For oral administration, the compositions can be provided in the form of tablets or capsules containing 1.0 to 500 mg of the active ingredient, particularly 1, 5, 10, 15, 20, 25, 50, 75, 100, 150, 200, 250, 300, 400, and 500 mg of the active ingredient for the symptomatic adjustment of the dosage to the patient to be treated. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

As noted above, the present invention also relates to a method of inhibiting HCV NS3 protease, inhibiting HCV replication, treating HCV infection and/or reducing the likelihood or severity of symptoms of HCV infection with a compound of the present invention in combination with one or more therapeutic agents and a pharmaceutical composition comprising a compound of the present invention and one or more therapeutic agents selected from the group consisting of a HCV antiviral agent, an immunomodulator, and an anti-infective agent. Such therapeutic agents active against HCV include, but are not limited to, ribavirin, levovirin, viramidine, thymosin alpha-1, R7025 (an enhanced interferon (Roche)), interferon-β, interferon-α, pegylated interferon-α (peginterferon-α), a combination of interferon-α and ribavirin, a combination of peginterferon-α and ribavirin, a combination of interferon-α and levovirin, and a combination of peginterferon-α and levovirin. Interferon-α includes, but is not limited to, recombinant interferon-α2a (such as ROFERON interferon available from Hoffmann-LaRoche, Nutley, N.J.), pegylated interferon-α2a (PEGASYS, interferon-α2b (such as INTRON-A interferon available from Schering Corp., Kenilworth, N.J.), pegylated interferon-α2b (PEGINTRON, a recombinant consensus interferon (such as interferon alphacon-1), albuferon (interferon-α bound to human serum albumin (Human Genome Sciences)), and a purified interferon-α product. Amgen's recombinant consensus interferon has the brand name INFERGEN®. Levovirin is the L-enantiomer of ribavirin which has shown immunomodulatory activity similar to ribavirin. Viramidine represents an analog of ribavirin disclosed in International Patent Application Publication WO 01/60379. In accordance with the method of the present invention, the individual components of the combination can be administered separately at different times during the course of therapy or concurrently in divided or single combination forms.

For the treatment of HCV infection, the compounds of the present invention may also be administered in combination with an agent that is an inhibitor of HCV NS3 serine protease. HCV NS3 serine protease is an essential viral enzyme and has been described to be an excellent target for inhibition of HCV replication. Both substrate and non-substrate based inhibitors of HCV NS3 protease inhibitors are disclosed in International Patent Application Publications WO 98/22496, WO 98/46630, WO 99/07733, WO 99/07734, WO 99/38888, WO 99/50230, WO 99/64442, WO 00/09543, WO 00/59929, WO 02/48116 and WO 02/48172, British Patent No. GB 2 337 262, and U.S. Pat. No. 6,323,180.

Ribavirin, levovirin, and viramidine may exert their anti-HCV effects by modulating intracellular pools of guanine nucleotides via inhibition of the intracellular enzyme inosine monophosphate dehydrogenase (IMPDH). IMPDH is the rate-limiting enzyme on the biosynthetic route in de novo guanine nucleotide biosynthesis. Ribavirin is readily phosphorylated intracellularly and the monophosphate derivative is an inhibitor of IMPDH. Thus, inhibition of IMPDH represents another useful target for the discovery of inhibitors of HCV replication. Therefore, the compounds of the present invention may also be administered in combination with an inhibitor of IMPDH, such as VX-497, which is disclosed in International Patent Application Publications WO 97/41211 and WO 01/00622; another IMPDH inhibitor, such as that disclosed in WO 00/25780; or mycophenolate mofetil. See A. C. Allison and E. M. Eugui, 44 (Suppl.) *Agents Action* 165 (1993).

For the treatment of HCV infection, the compounds of the present invention may also be administered in combination with the antiviral agent amantadine (1-aminoadamantane) [for a comprehensive description of this agent, see J. Kirschbaum, *Anal. Profiles Drug Subs.* 12: 1-36 (1983)].

For the treatment of HCV infection, the compounds of the present invention may also be administered in combination with the antiviral agent polymerase inhibitor R7128 (Roche).

The compounds of the present invention may also be combined for the treatment of HCV infection with antiviral 2'-C-branched ribonucleosides disclosed in R. E. Harry-O'Kuru et al., 62 *J. Org. Chem.* 1754-59 (1997); M. S. Wolfe et al., 36 *Tet. Lett.* 7611-14 (1995); U.S. Pat. No. 3,480,613; and International Patent Application Publications WO 01/90121, WO 01/92282, WO 02/32920, WO 04/002999, WO 04/003000 and WO 04/002422; the contents of each of which are incorporated by reference in their entirety. Such 2'-C-branched ribonucleosides include, but are not limited to, 2'-C-methyl-cytidine, 2'-C-methyl-uridine, 2'-C-methyl-adenosine, 2'-C-methyl-guanosine, and 9-(2-C-methyl-13-D-ribofuranosyl)-2,6-diaminopurine, and the corresponding amino acid ester of the ribose C-2', C-3', and C-5' hydroxyls and the corresponding optionally substituted cyclic 1,3-propanediol esters of the 5'-phosphate derivatives.

The compounds of the present invention may also be combined for the treatment of HCV infection with other nucleosides having anti-HCV properties, such as those disclosed in International Patent Application Publications WO 02/51425, assigned to Mitsubishi Pharma Corp.; WO 01/79246, WO 02/32920, WO 02/48165 and WO2005/003147 (including R1656, (2'R)-2'-deoxy-2'-fluoro-2'-C-methylcytidine, shown as compounds 3-6 on page 77); WO 01/68663; WO 99/43691; WO 02/18404 and WO 2006/021341, and U.S. Patent Application Publication US 2005/0038240, including 4'-azido nucleosides such as R1626, 4'-azidocytidine; U.S. Patent Application Publications US 2002/0019363, US 2003/0236216, US 2004/0006007 and US 2004/0063658; and International Patent Application Publications WO 02/100415, WO 03/026589, WO 03/026675, WO 03/093290, WO 04/011478, WO 04/013300 and WO 04/028481; the content of each is incorporated herein by reference in its entirety.

For the treatment of HCV infection, the compounds of the present invention may also be administered in combination with an agent that is an inhibitor of HCV NS5B polymerase. Such HCV NS5B polymerase inhibitors that may be used as combination therapy include, but are not limited to, those disclosed in International Patent Application Publications WO 02/057287, WO 02/057425, WO 03/068244, WO 2004/000858, WO 04/003138 and WO 2004/007512; U.S. Pat. No. 6,777,392 and U.S. Patent Application Publication US 2004/0067901; the content of each is incorporated herein by reference in its entirety. Other such HCV polymerase inhibitors include, but are not limited to, valopicitabine (NM-283; Idenix) and 2'-F-2'-beta-methylcytidine (see also WO 2005/003147).

In one embodiment, nucleoside HCV NS5B polymerase inhibitors that are used in combination with the present HCV NS3 protease inhibitors are selected from the following compounds: 4-amino-7-(2-C-methyl-β-D-arabinofuranosyl)-7H-pyrrolo[2,3-d]pyrimidine; 4-amino-7-(2-C-methyl-β-D-ribofuranosyl)-7H-pyrrolo[2,3-d]pyrimidine; 4-methylamino-7-(2-C-methyl-β-D-ribofuranosyl)-7H-pyrrolo[2,3-d]pyrimidine; 4-dimethylamino-7-(2-C-methyl-β-D-ribofuranosyl)-7H-pyrrolo[2,3-d]pyrimidine; 4-cyclopropylamino-7-(2-C-methyl-β-D-ribofuranosyl)-7H-pyrrolo[2,3-d]pyrimidine; 4-amino-7-(2-C-vinyl-β-D-ribofuranosyl)-

7H-pyrrolo[2,3-d]pyrimidine; 4-amino-7-(2-C-hydroxymethyl-β-D-ribofuranosyl)-7H-pyrrolo[2,3-d]pyrimidine; 4-amino-7-(2-C-fluoromethyl-β-D-ribofuranosyl)-7H-pyrrolo[2,3-d]pyrimidine; 4-amino-5-methyl-7-(2-C-methyl-β-D-ribofuranosyl)-7H-pyrrolo[2,3-d]pyrimidine; 4-amino-7-(2-C-methyl-β-D-ribofuranosyl)-7H-pyrrolo[2,3-d]pyrimidine-5-carboxylic acid; 4-amino-5-bromo-7-(2-C-methyl-β-D-ribofuranosyl)-7H-pyrrolo[2,3-d]pyrimidine; 4-amino-5-chloro-7-(2-C-methyl-β-D-ribofuranosyl)-7H-pyrrolo[2,3-d]pyrimidine; 4-amino-5-fluoro-7-(2-C-methyl-β-D-ribofuranosyl)-7H-pyrrolo[2,3-d]pyrimidine; 2,4-diamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidine; 2-amino-4-cyclopropylamino-7-(2-C-methyl-β-D-ribofuranosyl)-7H-pyrrolo[2,3-d]pyrimidine; 2-amino-7-(2-C-methyl-β-D-ribofuranosyl)-7H-pyrrolo[2,3-d]pyrimidin-4(3H)-one; 4-amino-7-(2-C-ethyl-β-D-ribofuranosyl)-7H-pyrrolo[2,3-d]pyrimidine; 4-amino-7-(2-C,2-O-dimethyl-β-D-ribofuranosyl)-7H-pyrrolo[2,3-d]pyrimidine; 7-(2-C-methyl-β-D-ribofuranosyl)-7H-pyrrolo[2,3-d]pyrimidin-4(3H)-one; 2-amino-5-methyl-7-(2-C, 2-O-dimethyl-β-D-ribofuranosyl)-7H-pyrrolo[2,3-d]pyrimidin-4(3H)-one; 4-amino-7-(3-deoxy-2-C-methyl-β-D-ribofuranosyl)-7H-pyrrolo[2,3-d]pyrimidine; 4-amino-7-(3-deoxy-2-C-methyl-β-D-arabinofuranosyl)-7H-pyrrolo[2,3-d]pyrimidine; 4-amino-2-fluoro-7-(2-C-methyl-β-D-ribofuranosyl)-7H-pyrrolo[2,3-d]pyrimidine; 4-amino-7-(3-C-methyl-β-D-ribofuranosyl)-7H-pyrrolo[2,3-d]pyrimidine; 4-amino-7-(3-C-methyl-β-D-xylofuranosyl)-7H-pyrrolo[2,3-d]pyrimidine; 4-amino-7-(2,4-di-C-methyl-β-D-ribofuranosyl)-7H-pyrrolo[2,3-d]pyrimidine; 4-amino-7-(3-deoxy-3-fluoro-2-C-methyl-β-D-ribofuranosyl)-7H-pyrrolo[2,3-d]pyrimidine; and the corresponding 5'-triphosphates; or a pharmaceutically acceptable salt thereof.

The compounds of the present invention may also be combined for the treatment of HCV infection with non-nucleoside inhibitors of HCV polymerase such as those disclosed in International Patent Application Publications WO 01/77091; WO 01/47883; WO 02/04425; WO 02/06246; WO 02/20497; WO 2005/016927 (in particular JTK003); the content of each is incorporated herein by reference in its entirety; and HCV-796 (Viropharma Inc.).

In one embodiment, non-nucleoside HCV NS5B polymerase inhibitors that are used in combination with the present HCV NS3 protease inhibitors are selected from the following compounds: 14-cyclohexyl-6-[2-(dimethylamino)ethyl]-7-oxo-5,6,7,8-tetrahydroindolo[2,1-a][2,5]benzodiazocine-11-carboxylic acid; 14-cyclohexyl-6-(2-morpholin-4-ylethyl)-5,6,7,8-tetrahydroindolo[2,1-a][2,5]benzodiazocine-11-carboxylic acid; 14-cyclohexyl-6-[2-(dimethylamino)ethyl]-3-methoxy-5,6,7,8-tetrahydroindolo[2,1-a][2,5]benzodiazocine-11-carboxylic acid; 14-cyclohexyl-3-methoxy-6-methyl-5,6,7,8-tetrahydroindolo[2,1-a][2,5]benzodiazocine-11-carboxylic acid; methyl ({[(14-cyclohexyl-3-methoxy-6-methyl-5,6,7,8-tetrahydroindolo[2,1-a][2,5]benzodiazocin-11-yl)carbonyl]amino}sulfonyl)acetate; ({[(14-cyclohexyl-3-methoxy-6-methyl-5,6,7,8-tetrahydroindolo[2,1-a][2,5]benzodiazocin-11-yl)carbonyl]amino}sulfonyl)acetic acid; 14-cyclohexyl-N-[(dimethylamino)sulfonyl]-3-methoxy-6-methyl-5,6,7,8-tetrahydroindolo[2,1-a][2,5]benzodiazocine-11-carboxamide; 3-chloro-14-cyclohexyl-6-[2-(dimethylamino)ethyl]-7-oxo-5,6,7,8-tetrahydroindolo[2,1-a][2,5]benzodiazocine 11-carboxylic acid; N'-(11-carboxy-14-cyclohexyl-7,8-dihydro-6H-indolo[1,2-e][1,5]benzoxazocin-7-yl)-N,N-dimethylethane-1,2-diaminium bis (trifluoroacetate); 14-cyclohexyl-7,8-dihydro-6H-indolo[1,2-e][1,5]benzoxazocine-11-carboxylic acid; 14-cyclohexyl-6-methyl-7-oxo-5,6,7,8-tetrahydroindolo[2,1-a][2,5]benzodiazocine-11-carboxylic acid; 14-cyclohexyl-3-methoxy-6-methyl-7-oxo-5,6,7,8-tetrahydroindolo[2,1-a][2,5]benzodiazocine-11-carboxylic acid; 14-cyclohexyl-6-[2-(dimethylamino)ethyl]-3-methoxy-7-oxo-5,6,7,8-tetrahydroindolo[2,1-a][2,5]benzodiazocine-11-carboxylic acid; 14-cyclohexyl-6-[3-(dimethylamino)propyl]-7-oxo-5,6,7,8-tetrahydroindolo[2,1-a][2,5]benzodiazocine-11-carboxylic acid; 14-cyclohexyl-7-oxo-6-(2-piperidin-1-ylethyl)-5,6,7,8-tetrahydroindolo[2,1-a][2,5]benzodiazocine-11-carboxylic acid; 14-cyclohexyl-6-(2-morpholin-4-ylethyl)-7-oxo-5,6,7,8-tetrahydroindolo[2,1-a][2,5]benzodiazocine-11-carboxylic acid; 14-cyclohexyl-6-[2-(diethylamino)ethyl]-7-oxo-5,6,7,8-tetrahydroindolo[2,1-a][2,5]benzodiazocine-11-carboxylic acid; 14-cyclohexyl-6-(1-methylpiperidin-4-yl)-7-oxo-5,6,7,8-tetrahydroindolo[2,1-a][2,5]benzodiazocine-11-carboxylic acid; 14-cyclohexyl-N-[(dimethylamino)sulfonyl]-7-oxo-6-(2-piperidin-1-ylethyl)-5,6,7,8-tetrahydroindolo[2,1-a][2,5]benzodiazocine-11-carboxamide; 14-cyclohexyl-6-[2-(dimethylamino)ethyl]-N-[(dimethylamino)sulfonyl]-7-oxo-5,6,7,8-tetrahydroindolo[2,1-a][2,5]benzodiazocine-11-carboxamide; 14-cyclopentyl-6-[2-(dimethylamino)ethyl]-7-oxo-5,6,7,8-tetrahydroindolo[2,1-a][2,5]benzodiazocine-11-carboxylic acid; 14-cyclohexyl-5,6,7,8-tetrahydroindolo[2,1-a][2,5]benzodiazocine-11-carboxylic acid; 6-allyl-14-cyclohexyl-3-methoxy-5,6,7,8-tetrahydroindolo[2,1-a][2,5]benzodiazocine-11-carboxylic acid; 14-cyclopentyl-6-[2-(dimethylamino)ethyl]-5,6,7,8-tetrahydroindolo[2,1-a][2,5]benzodiazocine-11-carboxylic acid; 14-cyclohexyl-6-[2-(dimethylamino)ethyl]-5,6,7,8-tetrahydroindolo[2,1-a][2,5]benzodiazocine-11-carboxylic acid; 13-cyclohexyl-5-methyl-4,5,6,7-tetrahydrofuro[3',2':6,7][1,4]diazocino[1,8-a]indole-10-carboxylic acid; 15-cyclohexyl-6-[2-(dimethylamino)ethyl]-7-oxo-6,7,8,9-tetrahydro-5H-indolo[2,1-a][2,6]benzodiazonine-12-carboxylic acid; 15-cyclohexyl-8-oxo-6,7,8,9-tetrahydro-5H-indolo[2,1-a][2,5]benzodiazonine-12-carboxylic acid; 13-cyclohexyl-6-oxo-6,7-dihydro-5H-indolo[1,2-d][1,4]benzodiazepine-10-carboxylic acid; and pharmaceutically acceptable salts thereof.

The HCV NS3 protease inhibitory activity of the present compounds may be tested using assays known in the art. One such assay is HCV NS3 protease time-resolved fluorescence (TRF) assay as described below and in International Patent Application Publication WO 2006/102087. Other examples of such assays are described in e.g., International Patent Application Publication WO 2005/046712. HCV NS3 protease inhibitors, such as those described herein have a Ki less than 50 μM, such as less than 10 μM, and less than 100 nM. Ki is determined by an NS3 protease assay. The assay is performed in a final volume of 100 μl in assay buffer containing 50 mM HEPES, pH 7.5, 150 mM NaCl, 15% glycerol, 0.15% Triton X-100, 10 mM DTT, and 0.1% PEG 8000. NS3 protease is pre-incubated with various concentrations of inhibitors in DMSO for 30 minutes. The reaction is initiated by adding the TRF peptide substrate (final concentration 100 nM). NS3 mediated hydrolysis of the substrate is quenched after 1 hour at room temperature with 100 μl of 500 mM MES, pH 5.5. Product fluorescence is detected using either a VICTOR V2 or FUSION fluorophotometer (Perkin Elmer Life and Analytical Sciences) with excitation at 340 nm and emission at 615 nm with a 400 μs delay. Testing concentrations of different enzyme forms are selected to result in a signal to background ratio (SB) of 10-30. $IC_{50}$ values are derived using a standard four-parameter fit to the data. $K_i$ values are derived from $IC_{50}$ values using the following formula, $$IC_{50}=K_i(1+[S]/K_M),\qquad \text{Eqn (1)},$$

where [S] is the concentration of substrate peptide in the reaction and $K_M$ is the Michaelis constant. See P. Gallinari et al., 38 BIOCHEM. 5620-32 (1999); P. Gallinari et al., 72 J. VIROL. 6758-69 (1998); M. Taliani et al., 240 ANAL. BIOCHEM. 60-67 (1996).

The present invention also includes processes for making compounds of formula (I). The compounds of the present invention can be readily prepared according to the following reaction schemes and examples, or modifications thereof, using readily available starting materials, reagents and conventional synthesis procedures. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, all variables are as defined above. The following reaction schemes and examples serve only to illustrate the invention and its practice.

General Description of Synthesis:

The compounds of the present invention may be synthesized as outlined in the general Schemes 1-3. Compounds wherein $R_1$ is $CONHP(O)R_{11}R_{12}$ or $P(O)R_{11}R_{12}$ can be made analogously according to the methods described in WO 2006/020276.

Scheme 1 outlines the synthesis of the proline portion of the molecule. An appropriately protected 4-hydroxyproline derivative (for example, a carbamate-protected nitrogen) and an ester-protected acid can be reacted with an appropriately substituted 4-hydroxyquinolinone in a single step via a Mitsunobu reaction (Mitsunobu, Synthesis 1-28 (1981)). Alternatively, a two-step process can be utilized in which the alcohol is converted to a leaving group such as a mesylate, benzenesulfonate, toluenesulfonate or 4-bromobenzenesulfonate in the first step by reaction with the appropriate sulfonyl chloride in a solvent with an amine base as acid scavenger. In a second step, the leaving group is displaced with an appropriately substituted quinoline in a number of organic solvents (for example DMF, acetonitrile or N-methylpyrrolidinone) with either an organic or inorganic base (for example, $K_2CO_3$ or $Cs_2CO_3$). The alkenyl functionality on the quinoline may be introduced at this or a later stage by palladium-catalyzed reaction of a halide substituent such as bromide or iodide, or other functionality such as a triflate with an organometallic reagent such as a vinyl or allyltrialkyltin. Alternatively, the alkenyl functionality may be introduced prior to the reaction with protected prolinol. In Scheme 1, P is a protecting group and R is H or $C_1$-$C_6$ alkyl.

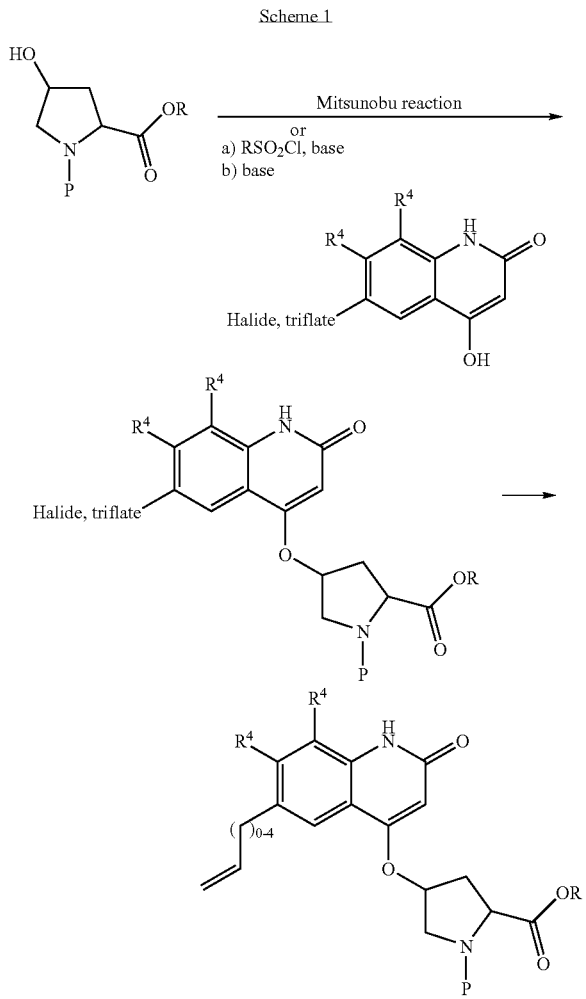

Scheme 2 describes the synthesis of the olefin-containing amino acid portion. Carbamate derivatives A may be prepared from the appropriate unsaturated alcohol by activation of the alcohol with phosgene or triphosgene in an organic solvent such as dioxane, followed by addition of an aqueous solution of the amino acid, which has been basified with, for example, sodium hydroxide. The same intermediates may also be prepared by reaction of an olefin containing alcohol with carbonyldiimidazole (or phosgene, triphosgene or diphosgene) in an organic solvent, followed by addition of the amino ester. The ester can then be hydrolyzed under a range of basic conditions known to those skilled in the art (T. W. Greene, Protective Groups in Organic Synthesis, Third Edition, John Wiley and Sons, 1999). In Scheme 2, R is H or $C_1$-$C_6$ alkyl.

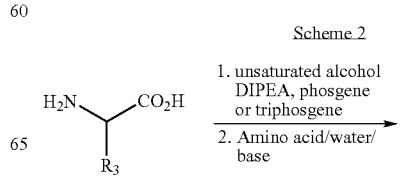

-continued

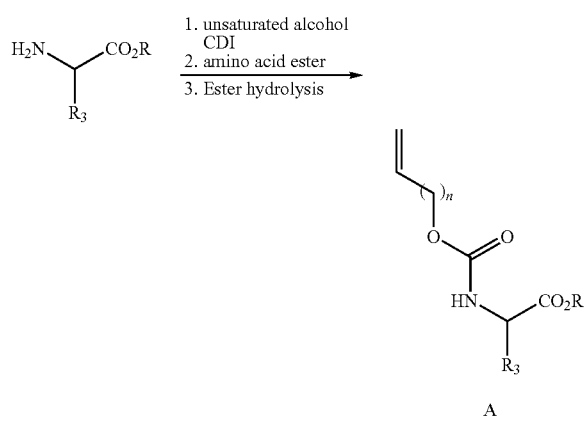

Deprotection of the carbamate protecting group on the proline portion may be carried out by a variety of methods known to persons skilled in the art (T. W. Greene, *Protective Groups in Organic Synthesis*, Third Edition, John Wiley and Sons, 1999). In Scheme 3, P is a protecting group and R is H or $C_1$-$C_6$ alkyl.

To complete the synthesis of the compounds of this invention, an amino acid derivative A can be coupled to the proline derivative utilizing a wide range of peptide-coupling reagents such as DCC, EDC, BOP, TBTU etc. Macrocyclization is then achieved by an olefin metathesis using a range of catalysts that have been described in the literature for this purpose in an appropriate solvent such as DCM, DCE or toluene. At this stage the olefinic bond produced in the ring-closing metathesis may be optionally hydrogenated to give a saturated linkage or functionalized in alternative ways such as cyclopropanation. The proline ester can then be hydrolyzed under basic conditions and coupled with the cyclopropylamino acid ester (the appropriate alkenyl or alkylcyclopropane portion of the molecule can be prepared as described previously (Llinas-Brunet et al., U.S. Pat. No. 6,323,180)) or acylsulfonamide. Appropriate functionalization of the quinoline, for example by alkylation with an alkyl halide, triflate, mesylate, then affords the desired compounds. Functionalization of the quinoline may also be carried out by initial conversion to the corresponding triflate and then reaction of the triflate with an appropriate amine. The coupling and quinoline functionalization steps may also be carried out in the reverse order.

Scheme 3

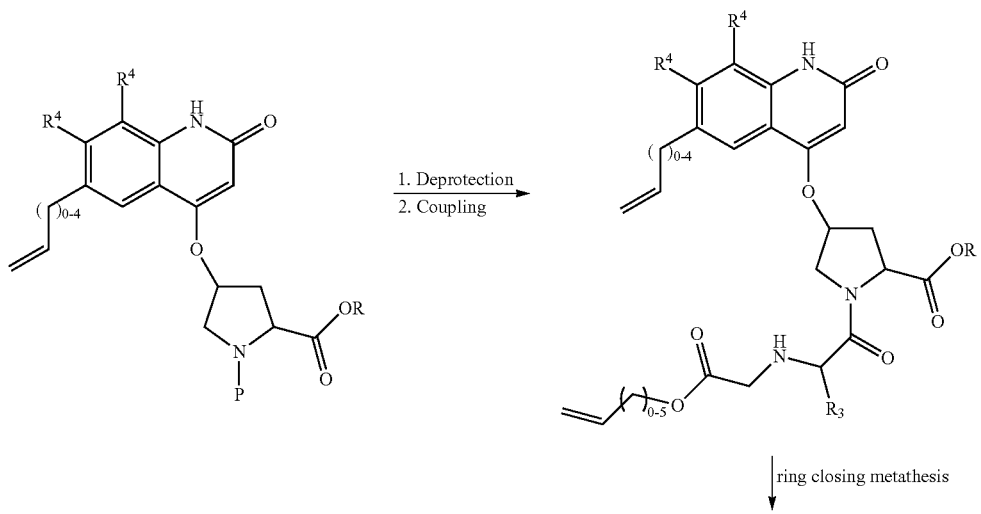

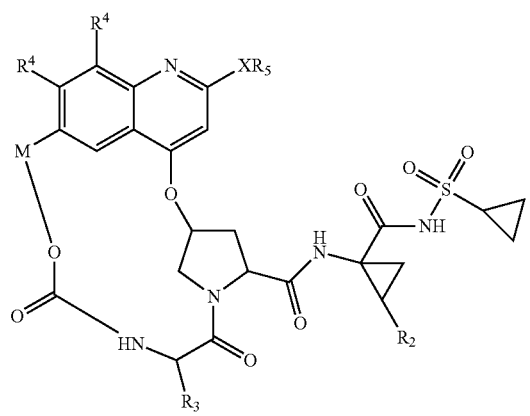

-continued either
a) functionaliztion of quinolone
b) coupling with

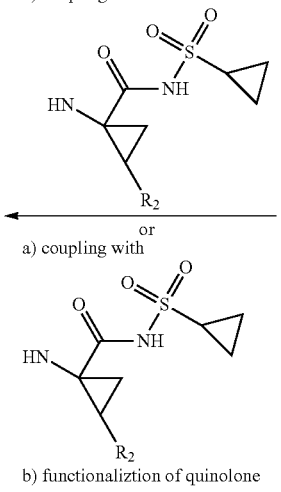

or
a) coupling with b) functionaliztion of quinolone

Olefin-metathesis catalysts include the following Ruthenium-based species: F. Miller et al., 118 *J. Am. Chem. Soc.* 9606 (1996); G. Kingsbury et al., 121 *J. Am. Chem. Soc.* 791 (1999); H. Scholl et al., 1 *Org. Lett.* 953 (1999); U.S. Patent Application Publication US2002/0107138; K. Furstner et al., 64 *J. Org. Chem.* 8275 (1999). The utility of these catalysts in ring-closing metathesis is well known in the literature (e.g. Trnka and Grubbs, 34 *Acc. Chem. Res.* 18 (2001).

F

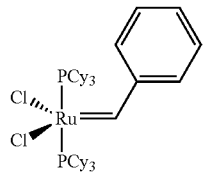

G

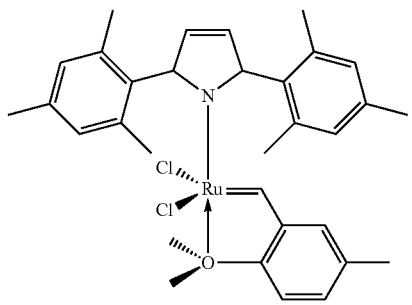

(Zhan catalyst 1A, Zannan Pharma Ltd.)

H

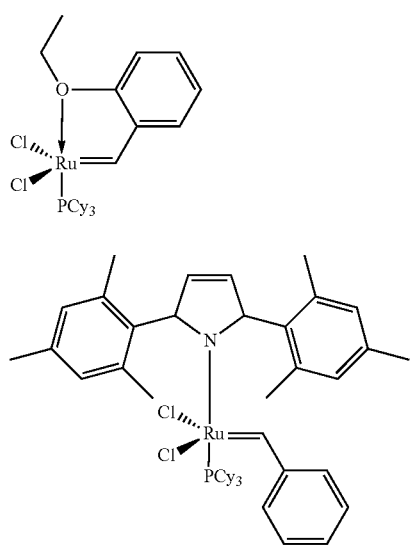

K

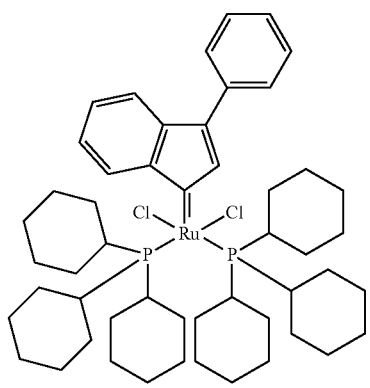

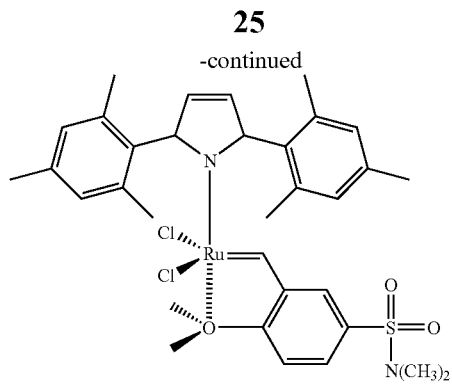
Zhan ruthenium metathesis catalyst RC-303
(Zhan catalyst 1B, RC-303,
Zannan Pharma Ltd.)
Scheme 4 illustrates the synthetic scheme to produce the specific compound in Example 1.
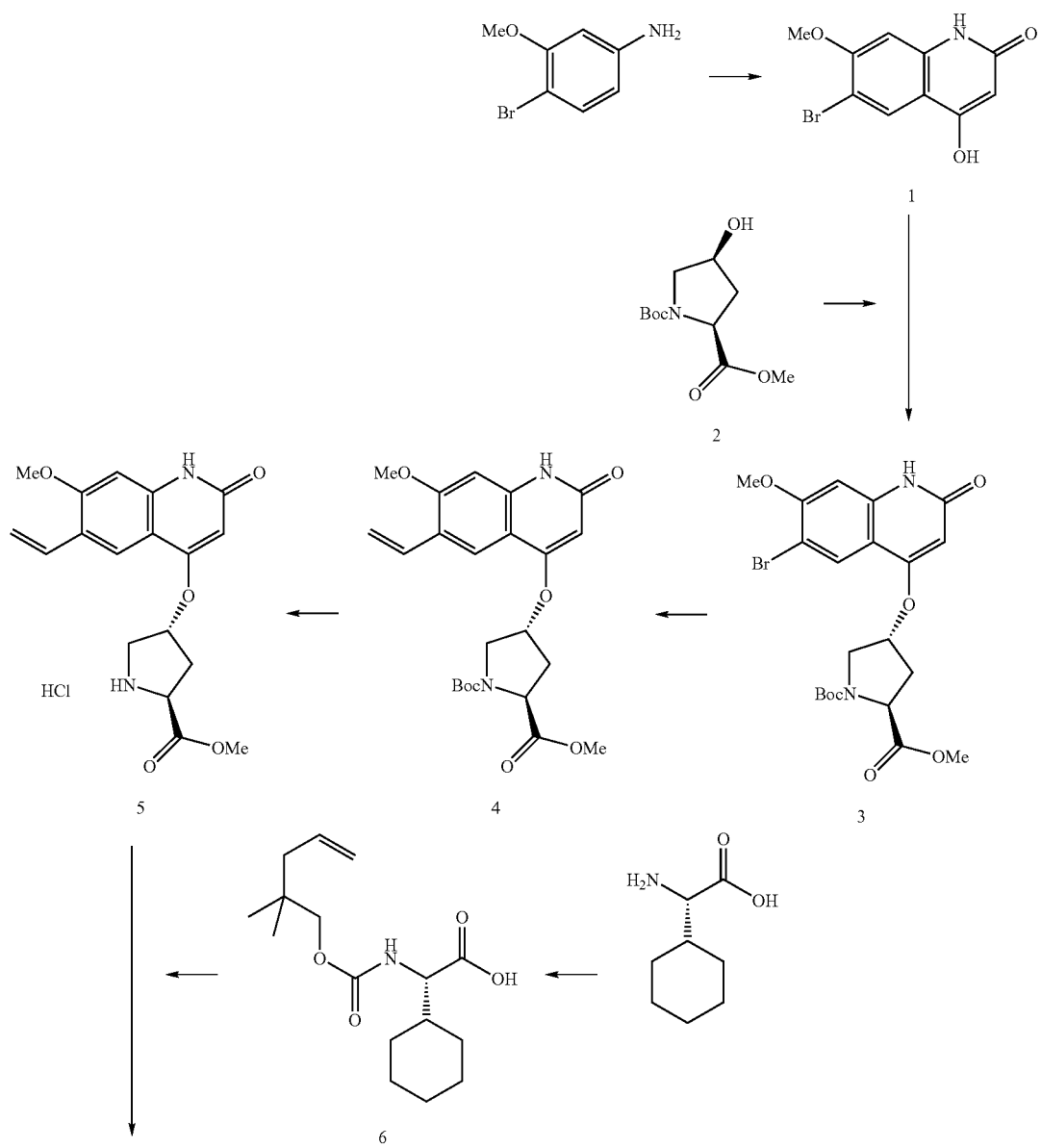

27
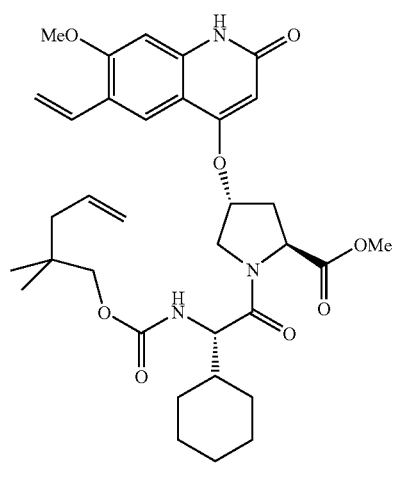
7
28
-continued
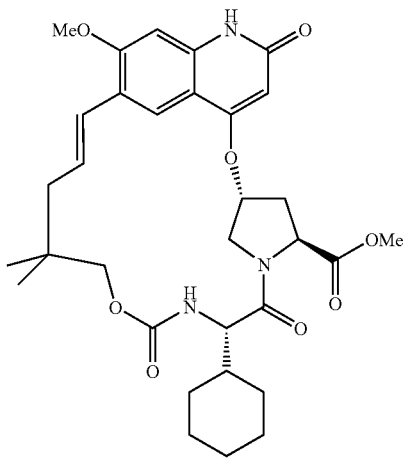
8
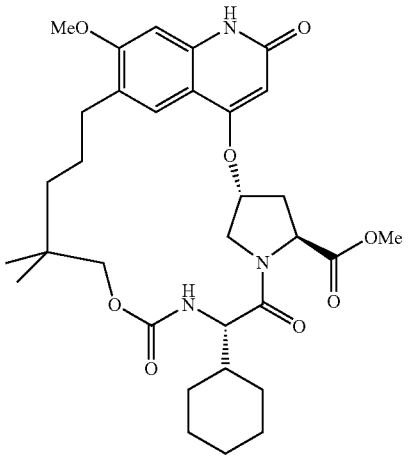
9
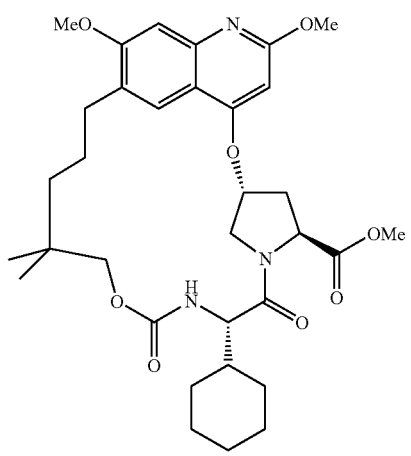
11
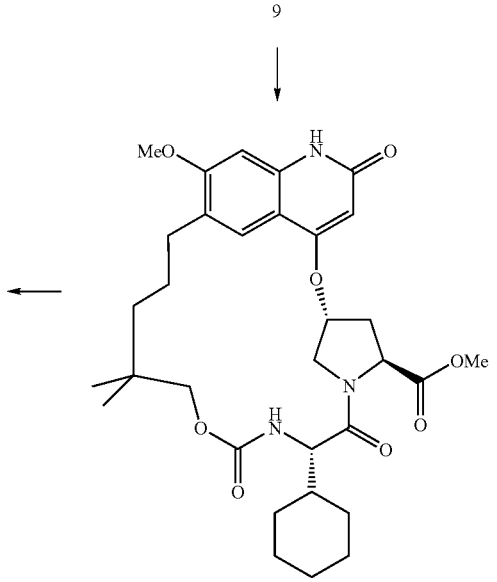
10

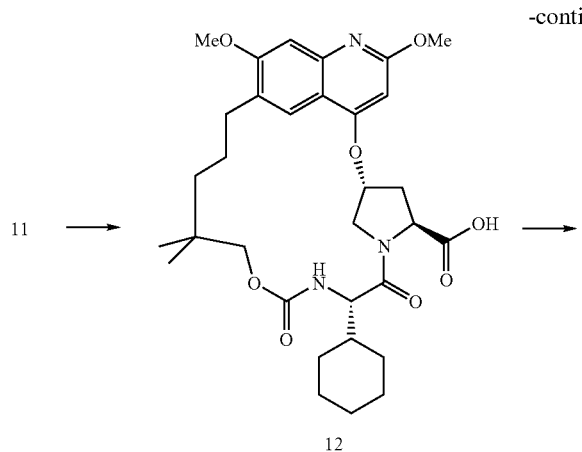

11 →

12

-continued

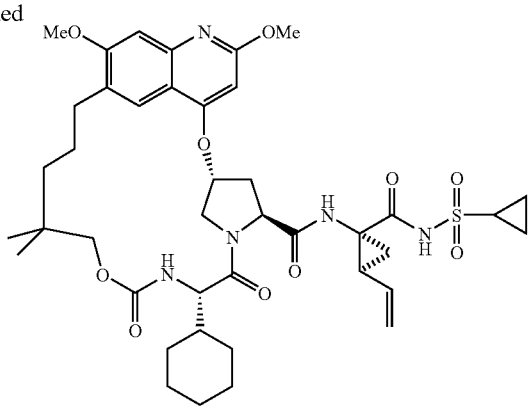

Example 1

LIST OF ABBREVIATIONS

BOP Benzotriazole-1-yl-oxy-tris-(dimethylamino)-phosphonium hexafluorophosphate
$Br_2BH$-SMe Dibromoborane-methylsulfide complex
n-BuLi n-Butyl lithium
$CDCl_3$ Deuterio-trichloromethane
CDI N,N'-Carbonyl diimidazole
$Cs_2CO_3$ Cesium carbonate
DCC Dicyclohexylcarbodiimide
DCE Dichloroethane
DCM Dichloromethane
DIAD Diisopropyl azodicarboxylate
DIEA Diethylamine
DIPA Diethylpropylamine
DMF Dimethylformamide
DMSO Dimethyl Sulfoxide
DPPF (also dppf) 1,1'-bid(Diphenylphosphino)ferrocene
EDC N-(3-Dimethylaminopropyl)-N'-ethylcarbodiimide
$Et_2O$ Diethyl ether
$Et_3N$ Triethylamine
EtOAc Ethyl acetate
EtOH Ethanol
$H_2$ Hydrogen or hydrogen atmosphere
HATU O-(7-Azabenzotriazol-1-yl)-N,N,N',N'-tetramethyluronium hexafluorophosphate
HCl Hydrochloric acid
$(HF)_3$-$Et_3N$ Triethylamine trihydrofluoride
IPA Isopropanol
$KHSO_4$ Potassium bisulfate
$K_2CO_3$ Potassium carbonate
LAH Lithium aluminium hydride
LiOH Lithium hydroxide
MeCN Acetonitrile
MeOH Methanol
$MgSO_4$ Magnesium sulfate
$N_2$ Nitrogen or nitrogen atmosphere
$NaHCO_3$ Sodium hydrogen carbonate (sodium bicarbonate)
NaOH Sodium hydroxide
$Na_2SO_4$ Sodium sulfate (anhydrous)
NIS N-iodosuccinimide
$Pd(Ph_3P)_4$ Tetrakis(triphenylphosphine) palladium (0)
$PdCl_2$(dppf)-DCM adduct dichloro[1,1'-bis(diphenylphosphino)ferrocene]palladium (II) dichloromethane adduct
$POCl_3$ Phosphoryl trichloride
$PPh_3$ Triphenyl phosphine
PhMe Toluene
RT Room temperature, approximately 25 C
TBTU O-Benzotriazol-1-yl-N,N,N',N'-tetramethyluronium tetrafluoroborate
TFA Trifluoroacetic acid
$Tf_2O$ Triflic anhydride
TfOH Trifluoromethane sulfonic acid
THF Tetrahydrofuran Synthesis of Intermediates Intermediates A

| Intermediate # | Structure | Name | Literature Reference |
|---|---|---|---|
| A1 | 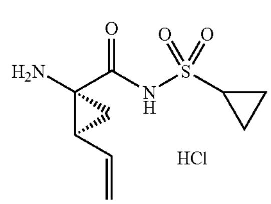 | (1R,2S)-1-Amino-N-(cyclopropylsulfonyl)-2-vinylcyclopropanecarboxamide hydrochloride | U.S. Pat. No. 6,995,174 |

| Intermediate # | Structure | Name | Literature Reference |
|---|---|---|---|
| A2 | 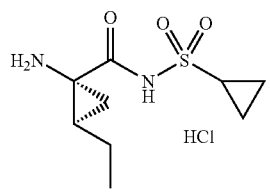 | Ethyl (1R,2S)-1-amino-2-vinylcyclopropanecarboxylate hydrochloride | U.S. Pat. No. 6,323,180 |

Intermediate A3: (1R,2R)-1-Amino-N-(cyclopropylsulfonyl)-2-ethylcyclopropanecarboxamide hydrochloride

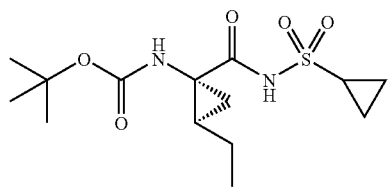

Step 1: t-Butyl ((1R,2R)-1-{[(cyclopropylsulfonyl)amino]carbonyl}-2-ethylcyclopropyl)carbamate A hydrogenation vessel was charged with a MeOH (1000 mL) slurry of t-butyl ((1R,2S)-1-{[(cyclopropylsulfonyl)amino]carbonyl}-2-vinylcyclopropyl)carbamate (164 g, 0.50 mol) (U.S. Pat. No. 6,995,174) and 5% Ru/C (dry, 7.5 wt %, 12.4 g) and stirred. The vessel was placed under $N_2$ (20 psi) and vented to atmospheric pressure (3×) to remove residual oxygen. The vessel was then placed under $H_2$ (50 psi). After 20 hours, the vessel was vented to atmospheric pressure. The reaction slurry was then transferred out of the reaction vessel and filtered through SOLKA FLOK (34 g, wetted with 100 mL MeOH) to yield a clear, light brown solution. The SOLKA FLOK was rinsed with MeOH (200 mL×2). The combined MeOH solutions were concentrated under reduced pressure to yield crude product as a white solid (153 g). The crude product was slurried in EtOAc (800 mL), warmed to 40° C. and aged 30 minutes. The solution was then seeded, aged 30 minutes, and heptane (500 mL) was added via addition funnel over 30 minutes. The partially crystallized solid was cooled to RT and aged overnight, after which additional heptane (500 mL) was added. After 1 hour, additional heptane (250 mL) was added via addition funnel, and the white slurry aged for 1 hour. The solution was filtered, and the solid was rinsed with heptane/EtOAc (500 mL, 4:1) and dried under reduced pressure to give t-butyl ((1R,2R)-1-{[(cyclopropylsulfonyl)amino]carbonyl}-2-ethylcyclopropyl)carbamate (125.9 g).

Step 2: (1R,2R)-1-Amino-N-(cyclopropylsulfonyl)-2-ethylcyclopropanecarboxamide hydrochloride (Intermediate A3)

A solution of the product from Step 1 (92 g, 0.28 mol) in DCM (1200 mL) was cooled to 0° C., and HCl was bubbled through the solution for 10 minutes. The cooling bath was then removed, and the reaction mixture stirred for 2 hours. $N_2$ was bubbled through the reaction mixture for 5 minutes, and the volatiles evaporated. The residue was azeotroped with DCM (3×) to give an off-white powder (75 g). LRMS $(M+H)^+$ Calcd.=233. found 233.

Intermediates B

Intermediate B1: (2S)-Cyclohexyl({[(2,2-dimethylpent-4-en-1-yl)oxy]carbonyl}amino)acetic acid

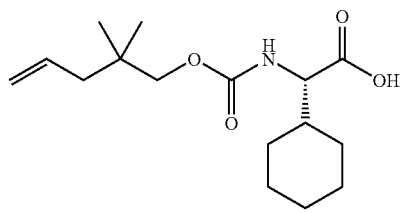

Step 1: Methyl (2S)-cyclohexyl({[(2,2-dimethylpent-4-en-1-yl)oxy]carbonyl}amino)acetate

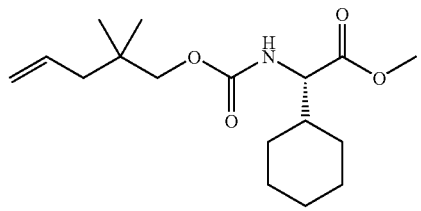

CDI (1.42 g, 8.76 mmol) was added to a solution of 2,2-dimethylpent-4-en-1-ol [Ref.: E. Alexander Hill et al., 46(6) J. Org. Chem. 1177-82 (1981).] (1.00 g, 8.76 mmol) in DMF (12 mL) cooled with a water bath. The mixture was stirred for 30 minutes at RT. Methyl (2S)-amino(cyclohexyl)acetate hydrochloride (1.82 g, 8.76 mmol) was then added, and the mixture was heated to 50° C. for 16 hours and then cooled to RT. The reaction mixture was partitioned between EtOAc and water/1N HCl. The organic layer was extracted with water (3×) and brine. The organic layer was then dried over MgSO$_4$, filtered and concentrated. The crude material was purified on silica gel (gradient elution, 0-10% EtOAc/hexane) to yield the title product (2.04 g, 75% yield). LRMS ESI$^+$ (M+H)$^+$ 312.5.

Step 2: (2S)-Cyclohexyl({[(2,2-dimethylpent-4-en-1-yl)oxy]carbonyl}amino)acetic acid LiOH (13.0 g, 310 mmol) was added to a solution of methyl (2S)-cyclohexyl({[(2,2-dimethylpent-4-en-1-yl)oxy]carbonyl}amino)acetate (19.3 g, 61.9 mmol) in THF (50 mL), MeOH (50 mL), and water (25 mL). The mixture was stirred for 18 hours at RT and concentrated to remove the MeOH and THF. The aqueous mixture was extracted with Et$_2$O. The pH was adjusted to pH 2 with 4 N HCl, and the mixture was extracted with Et$_2$O (2×). The organic layer was dried over MgSO$_4$, filtered and concentrated to yield Intermediate B1 (15.8 g, 86% yield). LRMS ESI$^+$ (M+H)$^+$ 298.4.

The following Intermediates B were prepared according to the procedures described for Intermediate B1 using the appropriate amino acid and alcohol.

| Int. | Amino Acid | Alcohol | Structure | Name | LRMS (M + H)$^+$ |
|---|---|---|---|---|---|
| B2 | L-cyclopentyl-glycine | (1R,2S)-2-allylcyclopentanol | 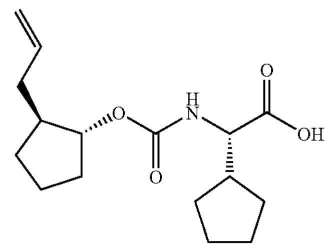 | (2S)-[({[(1R,2S)-2-allylcyclopentyl]oxy}carbonyl)amino](cyclopentyl)acetic acid | 296.2 |
| B3 | L-cyclopentyl-glycine | (1S,2R)-2-allylcyclopentanol | 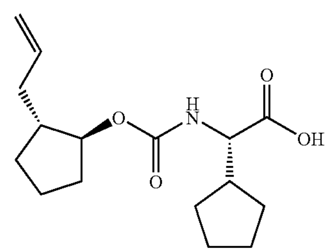 | (2S)-[({[(1S,2R)-2-allylcyclopentyl]oxy}carbonyl)amino](cyclopentyl)acetic acid | 296.2 |
| B4 | L-cyclopentyl-glycine | Cis-2-allylcyclopentanol | 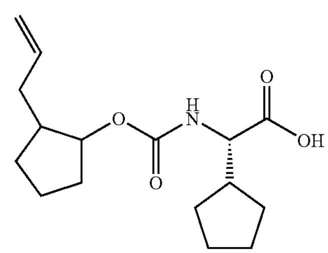 | (2S)-[({[(cis)-2-allylcyclopentyl]oxy}carbonyl)amino](cyclopentyl)acetic acid | 296.2 |
| B5 | L-cyclohexyl-glycine | (1R,2S)-2-allylcyclopentnol | 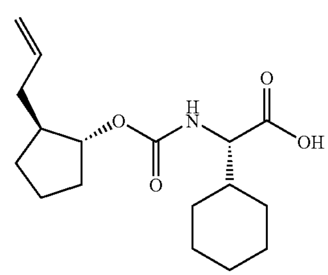 | (2S)-[({[(1R,2S)-2-allylcyclopentyl]oxy}carbonyl)amino](cyclohexyl)acetic acid | 310.2 |

-continued

| Int. | Amino Acid | Alcohol | Structure | Name | LRMS (M + H)+ |
|---|---|---|---|---|---|
| B6 | L-cyclohexyl-glycine | (1S,2R)-2-allylcyclopentanol | 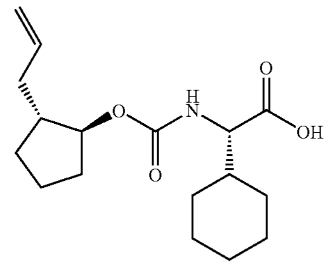 | (2S)-[({[(1S,2R)-2-allylcyclopentyl]oxy}carbonyl)amino](cyclohexyl)acetic acid | 310.2 |
| B7 | L-cyclohexyl-glycine | Cis-2-allylcyclopentanol | 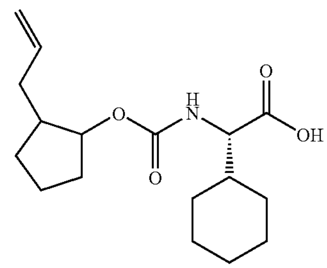 | (2S)-[({[(cis)-2-allylcyclopentyl]oxy}carbonyl)amino](cyclohexyl)acetic acid | 310.2 |
| B8 | L-t-butyl-glycine | 2,2-dimethylpent-4-en-1-ol | 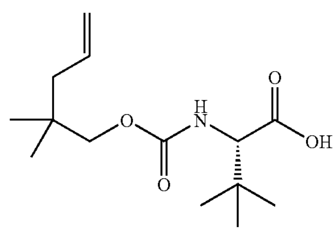 | N-{[(2,2-dimethylpent-4-en-1-yl)oxy]carbonyl}-3-methyl-L-valine | 272.2 |
| B9 | L-cyclohexyl-glycine | (2R)-2-methylpent-4-en-1-ol | 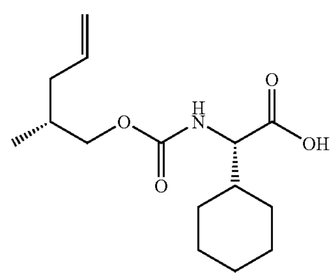 | (2S)-cyclohexyl[({[(2R)-2-methylpent-4-en-1-yl]oxy}carbonyl)amino]acetic acid | 284.2 |
| B10 | L-n-butyl glycine | 2,2-dimethylpent-4-en-1-ol | 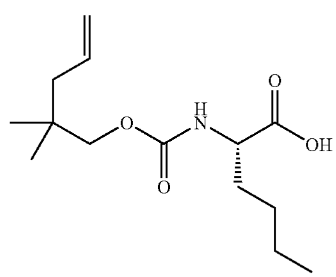 | N-{[(2,2-dimethylpent-4-en-1-yl)oxy]carbonyl}-L-norleucine | 272.2 |

-continued

| Int. | Amino Acid | Alcohol | Structure | Name | LRMS (M + H)+ |
|---|---|---|---|---|---|
| B11 | L-cyclohexyl-glycine | Trans-2-allylcyclohexanol | 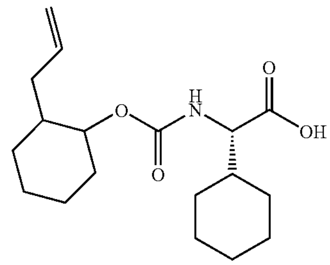 | (2S)-[({[(trans)-2-allylcyclohexyl]oxy}carbonyl)amino](cyclohexyl)acetic acid | 324.2 |
| B12 | L-cyclohexyl-glycine | Trans-2-(allyloxy)cyclo pentanol | 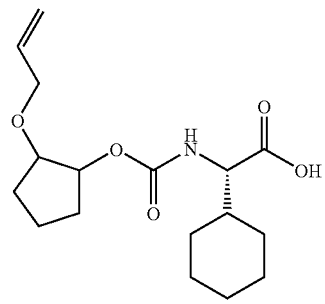 | (2S)-[({[(trans)-2-(allyloxy)cyclopentyl]oxy}carbonyl)amino](cyclohexyl)acetic acid | 326.2 |
| B13 | L-t-butyl-glycine | Trans-2-allylcyclohexanol | 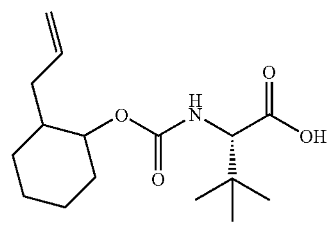 | N-{[(trans-2-allylcyclohexyl)oxy]carbonyl}-3-methyl-L-valine | 298.2 |
| B14 | L-t-butyl-glycine | Trans-4-allyltetrahydrofuran-3-ol | 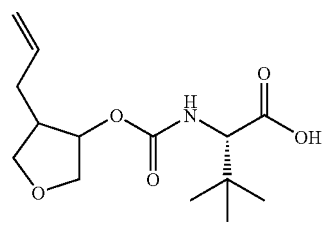 | N-{[(trans-4-allyltetrahydrofuran-3-yl)oxy]carbonyl}-3-methyl-L-valine | 286.2 |
| B15 | L-cyclopentyl-glycine | (1R,2S and 1S,2R)-2-allyl-2-methylcyclopentanol | 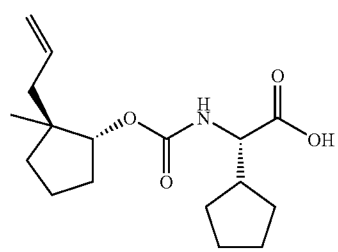 | (2S)-[({[(1R,2S and 1S,2R)-2-allyl-2-methylcyclopentyl]oxy}carbonyl)amino](cyclopentyl)acetic acid | 310.2 |
| B16 | L-t-butyl-glycine | (1R,2S)-2-allylcyclopentanol | 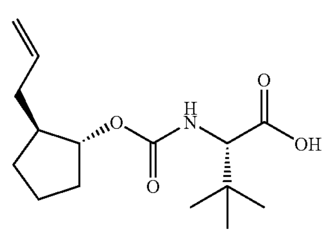 | N-({[(1R,2S)-2-allylcyclopentyl]oxy}carbonyl)-3-methyl-L-valine | 284.2 |

| Int. | Amino Acid | Alcohol | Structure | Name | LRMS (M + H)+ |
|---|---|---|---|---|---|
| B17 | L-t-butyl-glycine | (1S,2R)-2-allylcyclo pentanol | 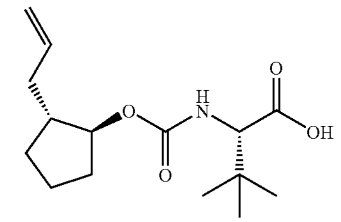 | N-({[(1S,2R)-2-allylcyclopentyl]oxy}carbonyl)-3-methyl-L-valine | 284.2 |
| B18 | L-t-butyl-glycine | (4-allylphenyl) methanol | 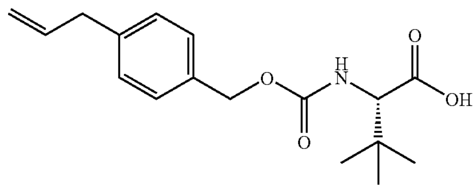 | N-{[(4-allylbenzyl)oxy]carbonyl}-3-methyl-L-valine | 306.2 |
| B20 | L-cyclopentyl-glycine | 2,2-dimethyl pent-4-en-1-ol | 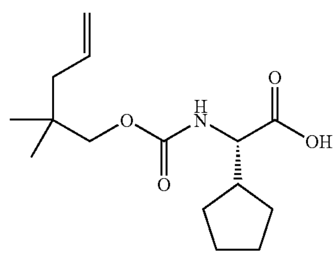 | (2S)-cyclopentyl({[(2,2-dimethylpent-4-en-1-yl)oxy]carbonyl}amino)acetic acid | 284.2 |

Intermediate B21: t-Butyl[(2,2-dimethylpent-4-yn-1-yl)oxy]dimethylsilane

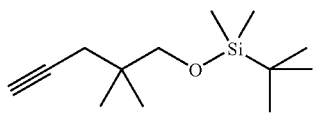

Step 1: Ethyl 2,2-dimethylpent-4-ynoate

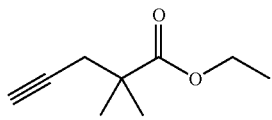

A solution of n-BuLi (199 mL, 498 mmol) as 2.5M in hexane was added slowly to a stirred solution of DIPA (74.3 mL, 521 mmol) in anhydrous THF (500 mL), at −75° C. and under nitrogen. The solution was stirred for 20 minutes, and a solution of ethyl isobutyrate (64 mL, 474 mmol) in THF (100 mL) was added dropwise to the solution over 1.5 hours. The solution was warmed to 0° C. and recooled to −75° C., then a solution of propargyl bromide (53.6 mL, 498 mmol) as 80% in PhMe was added dropwise. The reaction solution was slowly warmed to 22° C. and stirred for 20 hours, then quenched with water (150 mL). The water layer was extracted with ether (2×200 mL). The combined organic layer was washed with water (150 mL), brine (100 mL), dried over $Na_2SO_4$, filtered and concentrated. The residue was chromatographed on silica gel 60 eluting with 0 to 25% EtOAc in hexane, to give the title product. $^1H$ NMR (500 MHz, $CDCl_3$) δ 4.12 (q, J=7.1 Hz, 2H); 2.41 (s, 2H); 1.98 (s, 1H); 1.25 (s, 6H); 1.23 (t, J=7.1 Hz, 3H) ppm.

Step 2: 2,2-Dimethylpent-4-yn-1-ol

A solution of LAH (416 mL, 416 mmol) as 1M in $Et_2O$ was added slowly to a stirred solution of ethyl 2,2-dimethylpent-4-ynoate (64.1 g, 416 mmol) in anhydrous $Et_2O$ (416 mL), at −75° C. and under nitrogen, over 30 minutes. The reaction solution was stirred at 22° C. for 3 hours, then cooled to −75° C. and quenched with water (16 mL), 3M NaOH (20 mL), water (48 mL), then dried over $Na_2SO_4$, filtered and concentrated to give the title product. $^1H$ NMR (400 MHz, $CDCl_3$) δ 3.44 (d, J=6.0 Hz, 2H); 2.17 (d, J=2.8 Hz, 2H); 2.01 (t, J=2.6 Hz, 1H); 1.58 (s, 1H); 0.99 (s, 6H) ppm.

Step 3: t-Butyl[(2,2-dimethylpent-4-yn-1-yl)oxy]dimethylsilane

Imidazole (58.3 g, 857 mmol) and t-butydimethylchlorosilane (64.6 g, 429 mmol) were added to a stirred solution of 2,2-dimethylpent-4-yn-1-ol (43.7 g, 390 mmol) in DMF (195 mL), then the solution was stirred at 22° C., under $N_2$, for 20 hours. The reaction solution was extracted with ether (3×300 mL), washed with water (100 mL), brine (75 mL), dried over Na$_2$SO$_4$, filtered and concentrated. The residue was chromatographed on silica gel 60 (330 g), eluting with hexane, to give the title product. $^1$H NMR (400 MHz, CDCl$_3$) δ 3.29 (s, 2H); 2.10 (d, J=2.8 Hz, 2H); 1.91 (t, J=2.6 Hz, 1H); 0.90 (s, 6H); 0.86 (s, 9H); 0.00 (s, 6H) ppm.

Intermediates C

Intermediate C1: Methyl (2R,4S,7S)-7-cyclohexyl-23-methoxy-12,12-dimethyl-6,9,20-trioxo-3,4,6,7,8,9,12,13,14,15,19,20-dodecahydro-2H,11H-16,18-etheno-2,5-methanopyrido[4,3-k][1,10,3,6]dioxadiazacyclononadecine-4-carboxylate

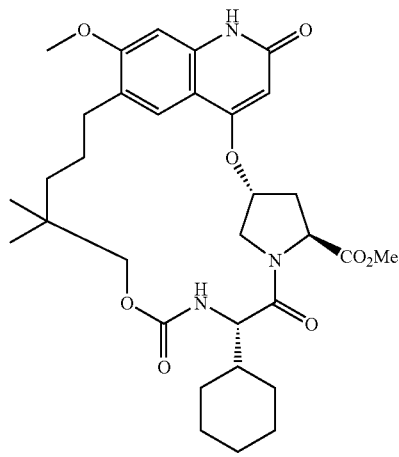

Step 1:
6-Bromo-4-hydroxy-7-methoxyquinolin-2(1H)-one

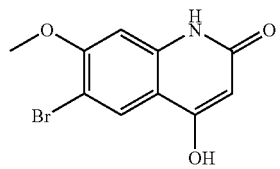

POCl$_3$ (5.07 mL, 54.4 mmol) was added to a mixture of 4-bromo-3-methoxyaniline (10 g, 49.5 mmol) and malonic acid (5.15 g, 49.5 mmol) with thorough mixing, and the mixture was then heated to 105° C. After 5 minutes, the reaction began to bubble vigorously, and eventually formed a hard foam; heating was continued for 1 hour. After cooling, water (200 mL) was added, and the mixture was stirred for 30 minutes. The solid was filtered off and washed with water. 2N NaOH (300 mL) was added to the solid, and stirring was continued overnight. The remaining solid was filtered off; EtOH (5 mL) was then added to the filtrate; and the basic layer was then acidified with concentrated HCl to pH 2. The resulting solid was then filtered off, washed with water. The solid was then transferred to a flask, and the remaining water was removed by stripping off EtOH (200 mL×2). The solid was then further dried under high vacuum for 15 hours to yield 8.75 g (66%) of the title compound as an off-white solid. LRMS ESI$^+$ (M+H)$^+$ 270.2/272.2.

Step 2: 1-t-butyl 2-methyl (2S,4R)-4-[(6-bromo-7-methoxy-2-oxo-1,2-dihydroquinolin-4-yl)oxy]pyrrolidine-1,2-dicarboxylate

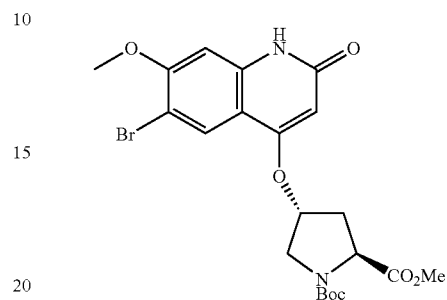

Cs$_2$CO$_3$ (8.42 g, 25.8 mmol) was added to a solution of 1-t-butyl 2-methyl (2S,4S)-4-{[(4-bromophenyl)sulfonyl]oxy}pyrrolidine-1,2-dicarboxylate (4 g, 8.61 mmol) and the product from Step 1, (3.49 g, 12.92 mmol) in NMP (86 ml) under N$_2$. The mixture was then heated to 60° C. for 6.5 hours, cooled to RT and partitioned between water and EtOAc. The organic layer was washed with water and brine, dried over MgSO$_4$, and the solvent removed in vacuo. The crude product (6.5 g) was purified on silica (gradient elution, 0-100% EtOAc/hexane, then 0-5% MeOH/DCM) to yield the title compound (2.26 g). LRMS ESI$^+$ ((M-Boc)+H)$^+$ 397.3/399.3.

Step 3: 1-t-butyl 2-methyl (2S,4R)-4-[(7-methoxy-2-oxo-6-vinyl-1,2-dihydroquinolin-4-yl)oxy]pyrrolidine-1,2-dicarboxylate

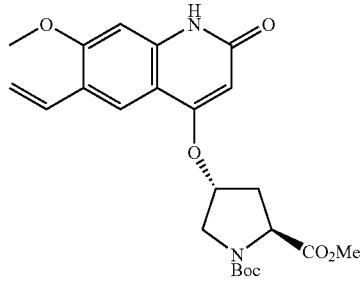

Potassium vinyltrifluoroborate (0.913 g, 6.82 mmol), Et$_3$N (0.950 mL, 6.82 mmol), and PdCl$_2$(dppf)-DCM adduct (0.186 g, 0.227 mmol) were added to a solution of the product from Step 2 (2.26 g, 4.54 mmol) in EtOH (45 mL), and the mixture heated to reflux for 1 hour. The volatiles were removed in vacuo, and the residue was partitioned between EtOAc and water. The organic layer was dried over MgSO$_4$; the solvent was removed in vacuo; and the crude material was purified on silica (gradient elution, 0-5% MeOH/DCM) to give the title compound (2.0 g). LRMS ESI⁺ ((M-Boc)+H)⁺ 345.3.

Step 4: Methyl (4R)-4-[(7-methoxy-2-oxo-6-vinyl-1,2-dihydroquinolin-4-yl)oxy]-L-prolinate hydrochloride

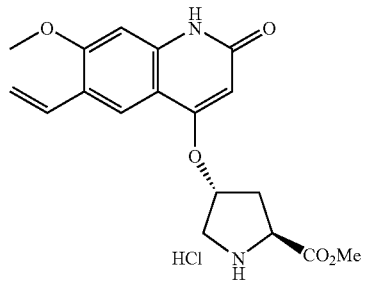

HCl (4M in dioxane) (23 mL, 91 mmol) was added to the product from Step 3 (2.02 g, 4.54 mmol) at RT. After 1.5 hours, the solvent was removed in vacuo, and the residue was azeotroped with Et₂O to yield the title compound (1.73 g) as a tan solid. LRMS ESI⁺ (M+H)⁺ 345.4.

Step 5: Methyl (4R)-1-[(2S)-2-cyclohexyl-2-([{(2,2-dimethylpent-4-en-1-yl)oxy]carbonyl}amino) acetyl]-4-[(7-methoxy-2-oxo-6-vinyl-1,2-dihydro quinolin-4-yl)oxy]-L-prolinate

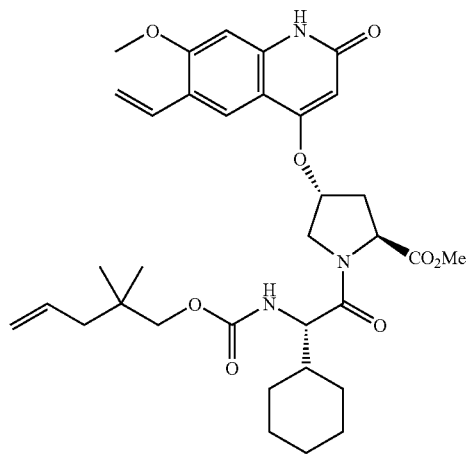

DIEA (1.16 mL, 6.62 mmol) and HATU (1.090 g, 2.87 mmol) were added to a solution of the product from Step 4 (0.84 g, 2.206 mmol) and Intermediate B1, (0.69 g, 2.32 mmol) in DMF (2 mL). After 15 minutes, 1N HCl and EtOAc were added; the organic layer was washed with water and brine and was dried over MgSO₄; and the solvent was removed in vacuo. The crude product was chromatographed on silica (gradient elution, 0-5% MeOH/DCM) to yield 1.65 g of impure material, which was dissolved in EtOAc and washed with 1N HCl (4×), water and brine. The organic layer was dried over MgSO₄, and the solvent was removed in vacuo to yield 1.13 g of the title compound. LRMS ESI⁺ (M+H)⁺ 624.6.

Step 6: Methyl (2R,4S,7S,14E)-7-cyclohexyl-23-methoxy-12,12-dimethyl-6,9,20-trioxo-3,4,6,7,8,9,12,13,19,20-decahydro-2H,11H-16,18-etheno-2,5-methanopyrido[4,3-k][1,10,3,6] dioxadiazacyclononadecine-4-carboxylate

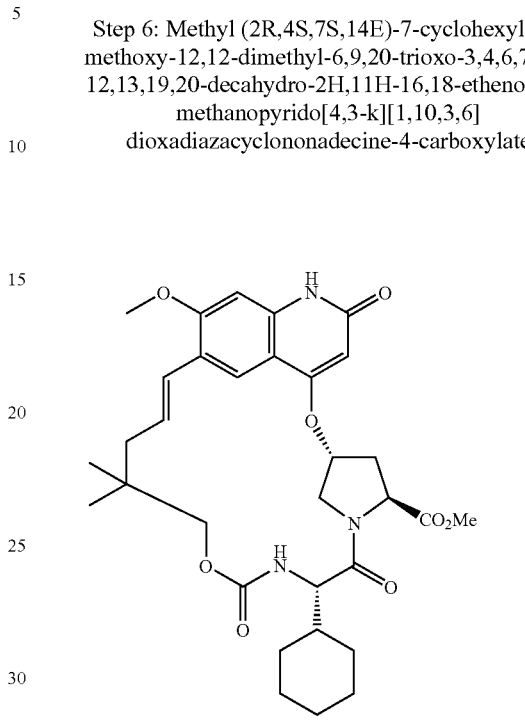

A solution of the product from Step 5 (1.61 g, 2.58 mmol) in DCM (520 mL) was degassed (N₂ bubbling for 15 minutes) and the Zhan 1B catalyst (0.189 g, 0.258 mmol) was added. After stirring for 24 hours at RT and 8 hours at reflux, the reaction mixture was cooled, the solvent removed in vacuo, and the crude product was purified on silica (gradient elution, 0-5% MeOH/DCM) to yield 1.53 g of the title compound as a greenish solid. LRMS ESI⁺ (M+H)⁺ 596.5.

Step 7: Methyl (2R,4S,7S)-7-cyclohexyl-23-methoxy-12,12-dimethyl-6,9,20-trioxo-3,4,6,7,8,9,12,13,14,15,19,20-dodecahydro-2H,11H-16,18-etheno-2,5-methanopyrido[4,3-k][1,10,3,6] dioxadiazacyclononadecine-4-carboxylate Pd/C (0.137 g, 0.128 mmol) was added to a solution of the product from Step 6 (1.53 g, 2.57 mmol) in EtOH (26 mL) under N₂. The atmosphere was then exchanged for H₂, and the mixture was stirred for 2 days. Additional Pd/C (0.137 g, 0.128 mmol) was added, and stirring was continued for 2 additional days. The reaction mixture was then filtered through glass wool, which was washed with EtOH. The solvent was removed in vacuo to yield 1.42 g of the title compound as a tan solid. ¹H NMR (500 MHz, CDCl₃): δ 9.87 (s, 1H), 7.36 (s, 1H), 6.51 (s, 1H), 5.77 (s, 1H), 5.29 (d, J=9.5 Hz, 1H), 5.11 (s, 1H), 4.66 (dd, J=10.25, 7.5 Hz, 1H), 4.57 (d, J=12.0 Hz, 1H), 4.40 (t, J=10.0 Hz, 1H), 4.33 (d, J=11.0 Hz, 1H), 3.93 (m, 1H), 3.88 (s, 3H), 3.76 (s, 3H), 3.30 (d, J=10.5 Hz, 1H), 2.98 (m, 1H), 2.72 (m, 1H), 2.15 (m, 2H), 1.89 (m, 2H), 1.75 (m, 3H), 1.67 (m, 1H), 1.47-1.03 (m, 8H), 1.01 (s, 3H), 0.83 (m, 1H), 0.78 (s, 3H). LRMS ESI⁺ (M+H)⁺ 598.5.

Intermediate C2: (2R,4S,7S)-7-cyclohexyl-4-{[((1R,2S)-1-{[(cyclopropylsulfonyl)amino]carbonyl}-2-vinylcyclopropyl)amino]carbonyl}-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecin-20-yl trifluoromethanesulfonate Step 1: (2R,4S,7S)-7-cyclohexyl-23-methoxy-12,12-dimethyl-6,9,20-trioxo-3,4,6,7,8,9,12,13,14,15,19,20-dodecahydro-2H,11H-16,18-etheno-2,5-methanopyrido[4,3-k][1,10,3,6]dioxadiazacyclononadecine-4-carboxylic acid

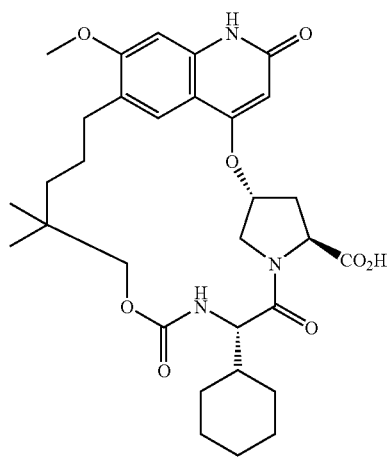

LiOH-monohydrate (1.4 g, 33.5 mmol) was added to a solution of Intermediate C1 (2 g, 3.35 mmol) in THF (20 mL), MeOH (1 mL) and water (20 mL). After 10 minutes, 1N HCl and Et₂O were added, resulting in precipitation of a solid. The solid was removed by filtration; the organic layer was separated from the filtrate and combined with the solid after dissolution in 10% MeOH/DCM. The solution was then dried over MgSO₄, and the solvent was removed in vacuo to yield the title compound (1.9 g). LRMS ESI⁺ (M+H)⁺ 584.5.

Step 2: (2R,4S,7S)-7-cyclohexyl-N-((1R,2S)-1-{[(cyclopropylsulfonyl)amino]carbonyl}-2-vinylcyclopropyl)-23-methoxy-12,12-dimethyl-6,9,20-trioxo-3,4,6,7,8,9,12,13,14,15,19,20-dodecahydro-2H,11H-16,18-(ethanediylidene)-2,5-methanopyrido[4,3-k][1,10,3,6]dioxadiazacyclononadecine-4-carboxamide

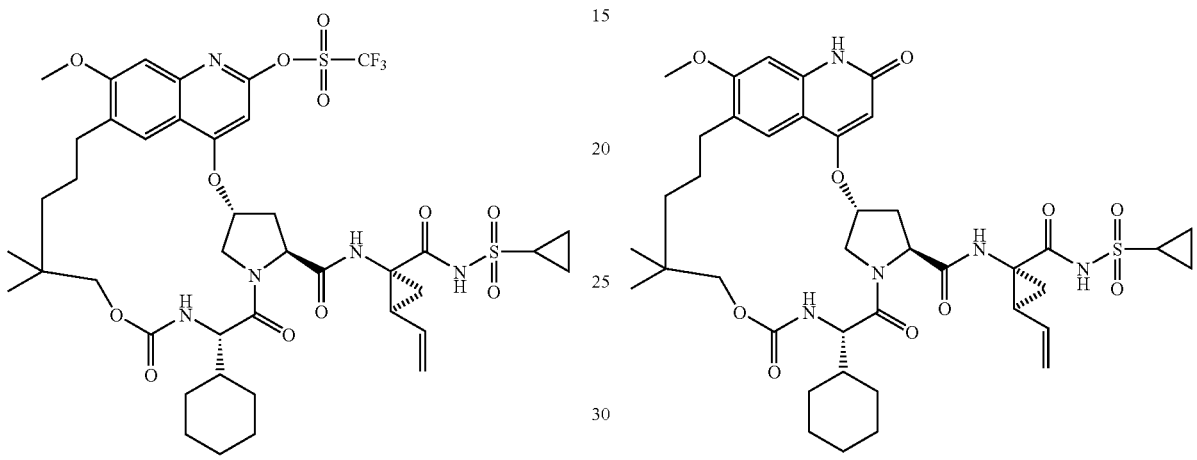

Intermediate A1 (1.11 g, 4.15 mmol), DMA (1.74 mL, 9.97 mmol) and HATU (1.58 g, 4.15 mmol) were added to a solution of the product from Step 1 (1.94 g, 3.32 mmol) in DCM (10 mL) and DMF (10 mL). After 18 hours, the mixture was poured into saturated NaHCO₃ and EtOAc. The organic layer was washed with 1N HCl, water, and brine. The organic layer was then dried over MgSO₄, and the solvent was removed in vacuo. The residue was purified on silica (gradient elution, 0-5% MeOH/DCM) to give the title compound (2.12 g). LRMS ESI⁺ (M+H)⁺ 796.7.

Step 3: (2R,4S,7S)-7-cyclohexyl-4-{[((1R,2S)-1-{[(cyclopropylsulfonyl)amino]carbonyl}-2-vinylcyclopropyl)amino]carbonyl}-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecin-20-yl trifluoromethanesulfonate Pyridine (0.215 mL, 2.66 mmol) and Tf₂O (0.45 mL, 2.66 mmol) were added to a solution of the product from Step 2 (2.12 g, 2.66 mmol) in DCM (100 mL) that had been cooled to 0° C. After 18 hours, the reaction mixture was extracted with aqueous NaHCO₃ and Et₂O. The organic layer was dried over MgSO₄, and the solvent was removed in vacuo. The residue was chromatographed on silica (gradient elution, 10-65% EtOAc/hexanes) to yield impure product, which was re-purified on silica (gradient elution, 1.5-3% acetone/DCM) and by reverse-phase chromatography (gradient elution, 40-95% MeCN/0.15% THF in water) to yield the title compound as a white solid (1.1 g,). LRMS ESI⁺ (M+H)⁺ 928.6.

Intermediate C3: Methyl (3R,5S,8S)-8-cyclopentyl-18-methoxy-13,13-dimethyl-7,10,22-trioxo-2,11-dioxa-6,9,21-triazatetracyclo[15.6.2.1³,⁶.0²⁰,²⁴]hexacosa-1(23),17,19,24-tetraene-5-carboxylate

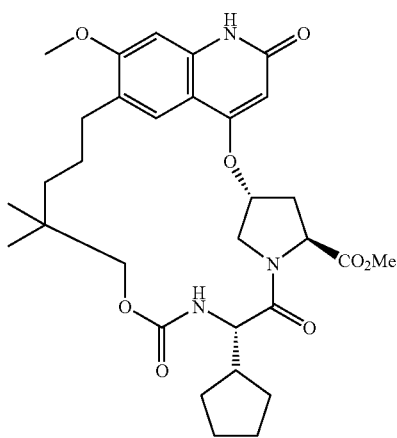

Step 1: Methyl (3R,5S,8S)-8-cyclopentyl-18-methoxy-13,13-dimethyl-7,10,22-trioxo-2,11,21-triazatetracyclo[15.6.2.1³,⁶.0²⁰,²⁴]hexacosa-1(23),17,19,24-tetraene-5-carboxylate The title compound was prepared according to the procedure for Intermediate C1, but using Intermediate B20 in Step 5. $^1$H NMR (500 MHz, CDCl$_3$): δ 9.56 (s, 1H), 7.38 (s, 1H), 6.50 (s, 1H), 5.77 (s, 1H), 5.34 (d, J=9.5 Hz, 1H), 5.10 (s, 1H), 4.65 (m, 2H), 4.43 (m, 2H), 3.93 (m, 1H), 3.88 (s, 3H), 3.9 (m, 1H), 3.88 (s, 3H), 3.76 (s, 3H), 3.72 (m, 2H), 3.30 (d, J=10.5 Hz, 1H), 3.0 (m, 1H), 2.74 (m, 1H), 2.32 (m, 1H), 2.12 (m, 2H), 1.84 (m, 2H), 1.68-1.5 (m, 5H), 1.4-1.3 (m, 5H), 1.26 1.26 (m, 2H), 1.07 (s, 3H), 0.78 (s, 1H). LRMS ESI$^+$ (M+H)$^+$ 584.5; calcd for C$_{31}$H$_{42}$N$_3$O$_8$: 584.3.

Intermediate C4: Methyl (3R,5S,8S)-8-cyclohexyl-18-methoxy-13,13-dimethyl-7,10-dioxo-22-{[(trifluoromethyl)sulfonyl]oxy}-2,11-dioxa-6,9,21-triazatetracyclo[15.6.2.1³,⁶.0²⁰,²⁴]hexacosa-1(24),17,19,20,22,24-hexaene-5-carboxylate

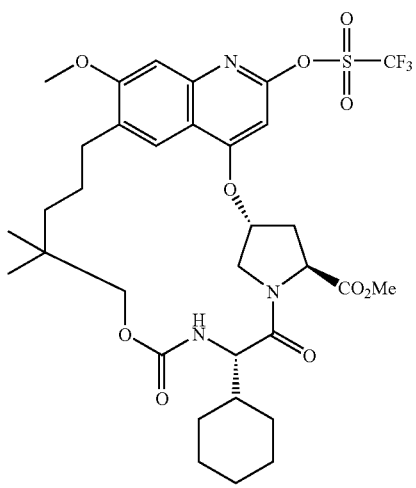

Pyridine (0.218 ml, 2.69 mmol) and then Tf$_2$O (0.137 ml, 0.808 mmol) were added dropwise to a solution of Intermediate C1 (322 mg, 0.539 mmol) in DCM (8 mL) cooled to 0° C. After 1 hour, Et$_2$O and aqueous NaHCO$_3$ were added; the organic layer was dried over MgSO$_4$; and the solvent was removed in vacuo. The crude product was purified on silica (gradient elution, 12 g, 0-50% EtOAc/hexane) to yield 357 mg of the title compound. $^1$H NMR (500 MHz, CDCl$_3$): δ 7.63 (s, 1H), 7.20 (s, 1H), 6.35 (s, 1H), 5.25 (m, 2H), 4.68 (dd, J=10.0 Hz, 8.0 Hz, 1H), 4.62 (dd, J=12.0 Hz, 1.5 Hz, 1H), 4.38 (t, J=9.5 Hz, 1H), 4.32 (d, J=15.5 Hz, 1H), 4.0 (m, 1H), 3.95 (s, 3H), 3.78 (s, 3H), 3.31 (d, J=10.5 Hz, 1H), 3.11 (m, 1H), 2.74 (m, 1H), 2.27 (m, 2H), 1.90 (m, 2H), 1.80 (m, 4H), 1.65 (m, 3H), 1.42 (m, 2H), 1.25 (m, 5H), 1.09 (m, 2H), 1.02 (s, 3H), 0.78 (s, 3H). LRMS ESI$^+$ (M+H)$^+$ 730.4; calcd for C$_{33}$H$_{43}$F$_3$N$_3$O$_{10}$S: 729.3.

Intermediate C5: 1-t-Butyl 2-methyl (2S,4R)-4-[(6-bromo-2-ethoxy-7-methoxyquinolin-4-yl)oxy]pyrrolidine-1,2-dicarboxylate

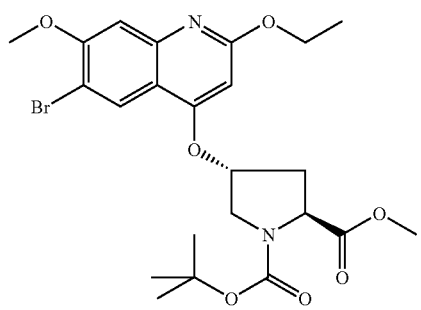

Step 1: Ethyl 3-ethoxy-3-iminopropanoate hydrochloride

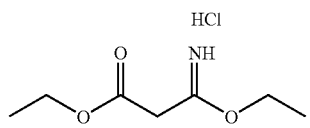

A stirred solution of ethyl cyanoacetate (30 mL, 281 mmol) and EtOH (18.1 mL, 278 mmol) in anhydrous Et$_2$O (28.1 mL), at 0° C., was bubbled with HCl gas until saturated. The reaction was stirred at 22° C. for 20 hours, and then concentrated to give the title product. $^1$H NMR (400 MHz, CDCl$_3$) δ 4.73 (q, J=7.1 Hz, 2H); 4.24 (q, J=7.2 Hz, 2H); 3.89 (s, 2H); 1.51 (t, J=7.0 Hz, 3H); 1.30 (t, J=7.2 Hz, 3H) ppm.

Step 2: Ethyl (3E)-3-[(4-bromo-3-methoxyphenyl)imino]-3-ethoxypropanoate

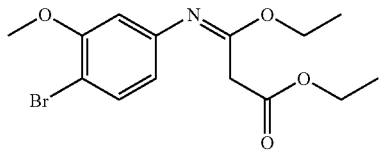

A mixture of ethyl 3-ethoxy-3-iminopropanoate hydrochloride (54.2 g, 277 mmol) and 4-bromo-3-methoxyaniline (56.0 g, 277 mmol) in EtOH (500 mL) was stirred under nitrogen, at 22° C., for 20 hours. The mixture was filtered and concentrated, then stirred in ether (100 mL), filtered and concentrated. The residue was chromatographed on silica gel 60 (gradient elution, 0-50% EtOAc in hexane) to give the title product. $^1$H NMR (400 MHz, CDCl$_3$) δ 7.40 (d, J=8.4 Hz, 1H); 6.43 (d, J=2.0 Hz, 1H); 6.30 (dd, J=8.4 & 2.4 Hz, 1H); 4.28 (q, J=7.1 Hz, 2H); 4.15 (q, J=7.1 Hz, 2H); 3.85 (s, 2H); 3.21 (s, 2H); 1.34 (t, J=7.2 Hz, 3H); 1.26 (t, J=7.0 Hz, 3H) ppm. LRMS (ESI) m/z 344.0 [(M+H)$^+$; calcd for C$_{14}$H$_{19}$BrNO$_4$: 344.0].

Step 3: 6-Bromo-2-ethoxy-7-methoxyquinolin-4-ol

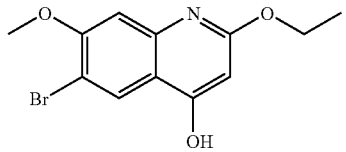

A solution of ethyl (3E)-3-[(4-bromo-3-methoxyphenyl)imino]-3-ethoxypropanoate (30.0 g, 87 mmol) in DOWTHERM (30 mL) was added to a stirred solution of DOWTHERM (300 mL) at 250° C. The resulting solution was stirred at 250° C. for 5 minutes, cooled to RT and filtered, and the cake was washed with hexane (3×50 mL), then dried to give the title product. $^1$H NMR (400 MHz, CD$_3$OD) δ 8.25 (s, 1H); 6.92 (s, 1H); 5.80 (s, 1H); 4.27 (q, J=7.1 Hz, 2H); 3.97 (s, 3H); 1.46 (t, J=7.0 Hz, 3H) ppm. LRMS (ESI) m/z 298.0 [(M+H)$^+$; calcd for C$_{12}$H$_{13}$BrNO$_3$: 298.0].

Step 4: 1-t-butyl 2-methyl (2S,4R)-4-[(6-bromo-2-ethoxy-7-methoxyquinolin-4-yl)oxy]pyrrolidine-1,2-dicarboxylate A suspension of 1-t-butyl 2-methyl (2S,4S)-4-{[(4-bromophenyl)sulfonyl]oxy}pyrrolidine-1,2-dicarboxylate (25.0 g, 53.8 mmol), 6-bromo-2-ethoxy-7-methoxyquinolin-4-ol (16.1 g, 53.8 mmol) and Cs$_2$CO$_3$ (52.6 g, 162 mmol) in NMP (300 mL) was stirred at 75° C., under N$_2$, for 2 hours. At 22° C., the reaction was diluted with water (500 mL) and extracted with EtOAc (3×500 mL). The combined EtOAc layers were washed with water (3×100 mL), brine (100 mL), dried over Na$_2$SO$_4$, filtered and concentrated. The residue was chromatographed on silica gel 60, eluting with 0 to 50% EtOAc in hexane, to give the title product. $^1$H NMR (400 MHz, CDCl$_3$) δ 8.13 (s, 1H); 7.16 (s, 1H); 6.02 (s, 1H); 5.05 (m, 1H); 4.49 (m, 3H); 4.00 (s, 3H); 3.91 (m, 2H); 3.78 (s, 3H); 2.67 (m, 1H); 2.37 (m, 1H); 1.47 (s, 3H); 1.44 (s, 9H) ppm. LRMS (ESI) m/z 525.0 [(M+H)$^+$; calcd for C$_{23}$H$_{30}$BrN$_2$O$_7$: 298.0].

EXAMPLES

Example 1

(2R,4S,7S)-7-cyclohexyl-N-((1R,2S)-1-{[(cyclopropylsulfonyl)amino]carbonyl}-2-vinylcyclopropyl)-20,23-dimethoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide

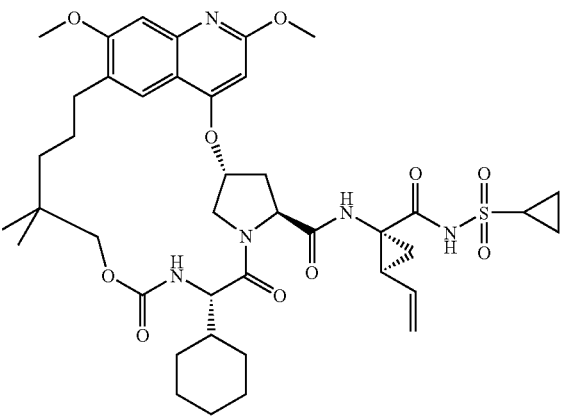

Step 1: Methyl (2R,4S,7S)-7-cyclohexyl-20,23-dimethoxy-12,12-dimethyl-6,9-dioxo-3,4,6,7,8,9,12,13,14,15-decahydro-2H,11H-16,18-etheno-2,5-methanopyrido[4,3-k][1,10,3,6]dioxadiazacyclononadecine-4-carboxylate

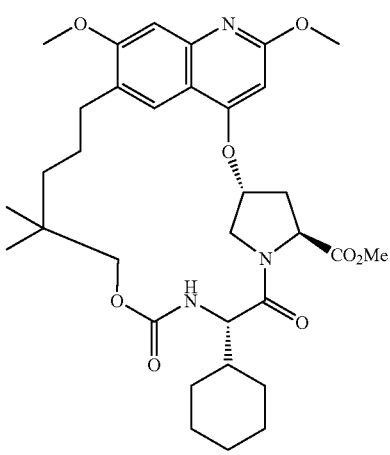

Trimethyloxonium trifluoroborate (12.99 mg, 0.088 mmol) was added to a solution of Intermediate C1 (50 mg, 0.084 mmol) in DCM (5 mL). The mixture was then stirred at RT for 5 hours, and partitioned between aqueous NaHCO$_3$ and DCM. The organic layer was dried over MgSO$_4$, and the solvent was removed in vacuo to yield 42 mg of the title compound as an 85:15 mixture with starting material. LRMS ESI⁺ (M+H)⁺ 612.7.

Step 2: (2R,4S,7S)-7-cyclohexyl-20,23-dimethoxy-12,12-dimethyl-6,9-dioxo-3,4,6,7,8,9,12,13,14,15-decahydro-2H,11H-16,18-etheno-2,5-methanopyrido[4,3-k][1,10,3,6]dioxadiazacyclononadecine-4-carboxylic acid

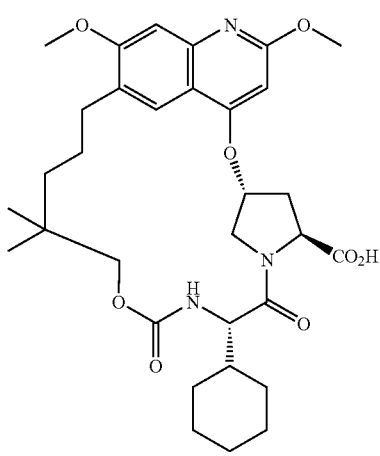

LiOH (27.4 mg, 0.654 mmol) was added to a solution of product from Step 1 (40 mg, 0.065 mmol) in THF (1 mL), MeOH (1.0 mL), and water (0.5 mL). After 30 minutes, Et$_2$O and 1N HCl were added. This caused a solid to precipitate, and after filtration, the solid was dissolved with 10% MeOH/DCM. The organic layers (Et$_2$O layer and DCM/MeOH) were then combined and dried over Na$_2$SO$_4$, and the solvent was removed in vacuo to yield 46 mg of the title compound. LRMS ESI⁺(M+H)⁺ 598.6.

Step 3: (2R,4S,7S)-7-cyclohexyl-N-((1R,2S)-1-{[(cyclopropylsulfonyl)amino]carbonyl}-2-vinylcyclopropyl)-20,23-dimethoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide DIEA (0.054 mL, 0.308 mmol) and HATU (52.7 mg, 0.139 mmol) were added to a solution of the product from Step 2 (46 mg, 0.077 mmol) and Intermediate A1 (30.8 mg, 0.115 mmol) in DMF (1.0 mL). The reaction mixture was stirred for 5 minutes at RT, then purified directly by reverse-phase chromatography (CH$_3$CN/water/0.05% TFA) to yield 27 mg of the title compound as a white solid. ¹H NMR (500 MHz, CD$_3$OD): δ 9.30 (s, 1H), 7.71 (s, 1H), 7.45 (d, J=9.0 Hz, 1H), 7.11 (s, 1H), 6.79 (s, 1H), 5.72 (m, 2H), 5.26 (d, J=17.0 Hz, 1H), 5.11 (d, J=10.5 Hz, 1H), 4.62 (d, J=12.0 Hz, 1H), 4.44 (m, 1H), 4.31 (d, J=11.0 Hz, 1H), 4.25 (m, 1H), 4.22 (s, 3H), 4.07 (m, 1H), 3.99 (s, 3H), 3.28 (m, 1H), 3.15 (m, 1H), 2.95 (m, 1H), 2.75 (m, 1H), 2.33-2.14 (m, 3H), 1.89 (m, 3H), 1.77-1.50 (m, 6H), 1.48-1.20 (m, 8H), 1.11 (m, 2H), 1.06 (s, 3H), 0.99 (m, 1H), 0.77 (s, 3H). LRMS ESI⁺ (M+H)⁺ 810.6.

Example 2

(2R,4S,7S)-7-cyclohexyl-N-((1R,2S)-1-{[(cyclopropylsulfonyl)amino]carbonyl}-2-vinylcyclopropyl)-20-ethoxy-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide

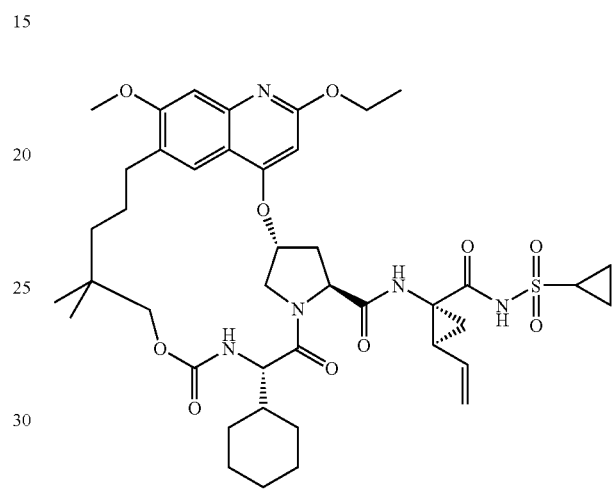

Step 1: Methyl (2R,4S,7S)-7-cyclohexyl-20-ethoxy-23-methoxy-12,12-dimethyl-6,9-dioxo-3,4,6,7,8,9,12,13,14,15-decahydro-2H,11H-16,18-etheno-2,5-methanopyrido[4,3-k][1,10,3,6]dioxadiazacyclononadecine-4-carboxylate

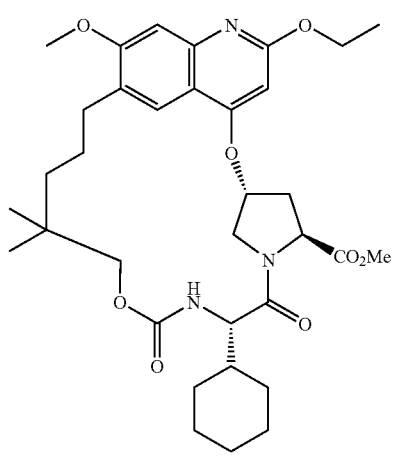

K$_2$CO$_3$ (111 mg, 0.803 mmol) was added to a solution of Intermediate C1 (80 mg, 0.134 mmol) in DMF (2 mL), followed by slow addition of ethyl iodide (0.022 mL, 0.268 mmol). The reaction mixture was then heated to 70° C. for 3 hours and cooled to RT, and water, Et₂O, and EtOAc were added. The organic layer was dried over MgSO₄, and the solvent was removed in vacuo to give 90 mg of the title compound as a ~1:1 mixture with the corresponding N-alkylated product, methyl (2R,4S,7S)-7-cyclohexyl-19-ethyl-23-methoxy-12,12-dimethyl-6,9,20-trioxo-3,4,6,7,8,9,12,13,14,15,19,20-dodecahydro-2H,11H-16,18-etheno-2,5-methanopyrido[4,3-k][1,10,3,6]dioxadiazacyclononadecine-4-carboxylate. The mixture was used directly in the next step. LRMS ESI⁺ (M+H)⁺ 626.5.

Step 2: (2R,4S,7S)-7-cyclohexyl-N-((1R,2S)-1-{[(cyclopropylsulfonyl)amino]carbonyl}-2-vinylcyclopropyl)-20-ethoxy-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide The title compound was prepared from the product of Step 1, according to the procedures in Example 1 Steps 2 and 3. ¹H NMR (500 MHz, CD₃OD): δ 9.32 (s, 1H), 7.75 (s, 1H), 7.10 (s, 1H), 6.94 (s, 1H), 5.85 (s, 1H), 5.75 (m, 1H), 2.98 (d, J=17.5 Hz, 1H), 5.11 (d, J=10.5 Hz, 1H), 4.63 (m, 3H), 4.43 (m, 1H), 4.31 (d, J=11.0 Hz, 1H), 4.24 (d, J=10.0 Hz, 1H), 4.09 (m, 1H), 4.01 (s, 3H), 3.27 (d, J=10.0 Hz, 1H), 3.16 (m, 1H), 2.96 (m, 1H), 2.59 (m, 1H), 2.33 (m, 1H), 2.26 (m, 1H), 2.19 (m, 1H), 2.03 (s, 1H), 1.88 (m, 2H), 1.79-1.46 (m, 9H), 1.39 (m, 1H), 1.33-1.20 (m, 7H), 1.10 (m, 2H), 1.05 (s, 3H), 0.98 (m, 1H), 0.76 (s, 3H). LRMS ESI⁺(M+H)⁺ 824.7.

Example 3

(3R,5S,8S)-8-cyclohexyl-N-((1R,2S)-1-{[(cyclopropylsulfonyl)amino]carbonyl}-2-vinylcyclopropyl)-18-methoxy-13,13-dimethyl-22-[(2-methyl-1,3-thiazol-4-yl)methoxy]-7,10-dioxo-2,11-dioxa-6,9,21-triazatetracyclo[15.6.2.1³,⁶.0²⁰,²⁴]hexacosa-1(23),17,19,21,24-pentaene-5-carboxamide

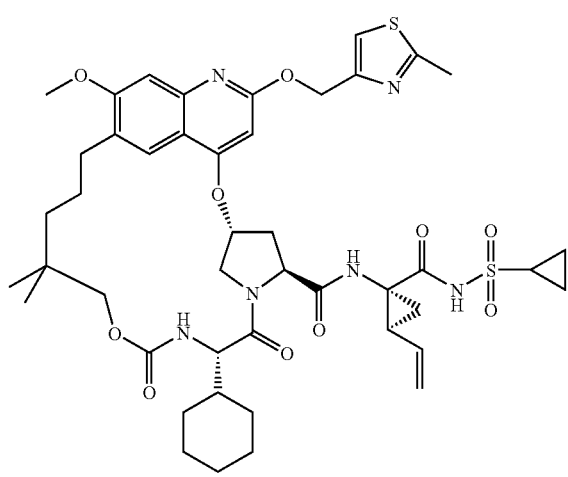

Step 1: Methyl (3R,5S,8S)-8-cyclohexyl-18-methoxy-13,13-dimethyl-22-[(2-methyl-1,3-thiazol-4-yl)methoxy]-7,10-dioxo-2,11-dioxa-6,9,21-triazatetracyclo[15.6.2.1³,⁶.0²⁰,²⁴]hexacosa-1(23),17,19,21,24-pentaene-5-carboxylate

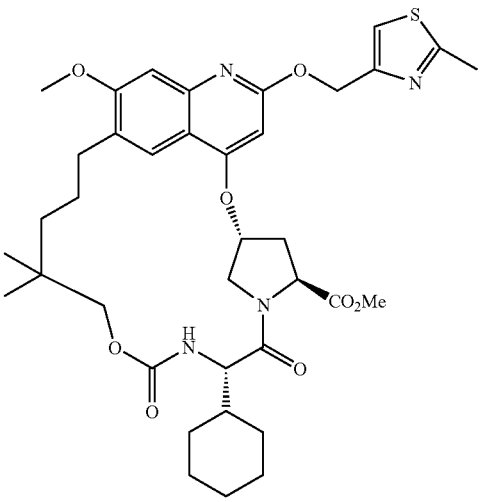

Silver oxide (100 mg, 0.42 mmol) and 4-(chloromethyl)-2-methyl-1,3-thiazole (33 mg, 0.225 mmol) were added to a solution of Intermediate C3 (50 mg, 0.084 mmol) in DMF (2 mL). The mixture was then heated to 100° C. for 15 hours, diluted with EtOAc, and filtered through a pad of glass wool. The mixture was then extracted with water and brine and dried over MgSO₄; and the solvent was removed in vacuo. The crude material was then purified on silica (gradient elution, 0-70% EtOAc/hexanes) to yield 55 g of the title compound. LRMS ESI⁺(M+H)⁺ 709.5; calcd for C₃₇H₄₉N₄O₈S: 709.3.

Step 2: (3R,5S,8S)-8-cyclohexyl-N-((1R,2S)-1-{[(cyclopropylsulfonyl)amino]carbonyl}-2-vinylcyclopropyl)-18-methoxy-13,13-dimethyl-22-[(2-methyl-1,3-thiazol-4-yl)methoxy]-7,10-dioxo-2,11-dioxa-6,9,21-triazatetracyclo[15.6.2.1³,⁶.0²⁰,²⁴]hexacosa-1(23),17,19,21,24-pentaene-5-carboxam The title compound was prepared according to Steps 2 and 3 of Example 1. ¹H NMR (500 MHz, CD₃OD): δ 9.31 (s, 1H), 7.76 (s, 1H), 7.69 (s, 1H), 7.10 (s, 1H), 7.09 (s, 1H), 5.81 (br s, 1H), 5.73 (m, 1H), 5.65 (m, 2H), 5.27 (dd, J=17.0 Hz, 1.5 Hz, 1H), 5.11 (dd, J=10.5 Hz, 1.5 hz, 1H), 4.68 (d, J=12.5 Hz, 1H), 4.43 (dd, J=11.0 Hz, 7 Hz, 1H), 4.32 (d, J=11.0 Hz, 1H), 4.26 (d, J=11.0 Hz, 1H), 4.10 (dd, j=12.0 Hz, 2.5 Hz, 1H), 4.0 (s, 3H), 3.16 (m, 2H), 2.95 (m, 1H), 2.71 (s, 3H), 2.61 (m, 1H), 2.36 (m, 1H), 2.28 (m, 1H), 2.18 (m, 1H), 1.91 (m, 3H), 1.77-1.51 (m, 7H), 1.4-1.2 (m, 9H), 1.1 (m, 2H), 1.06 (s, 3H), 1.0 (m, 2H), 0.77 (s, 3H). LRMS ESI⁺ (M+H)⁺ 907.5; calcd for C₄₅H₅₉N₆O₁₃S₂: 907.4.

The following compounds were prepared according to Example 2 or Example 3, using the appropriate alkylating agent in place of ethyl iodide in Step 1 and the appropriate Intermediate C.

| Ex. | Structure | Name | Int. | Alkylating agent | Procedure | LRMS (M + H)+ |
|---|---|---|---|---|---|---|
| 4 | 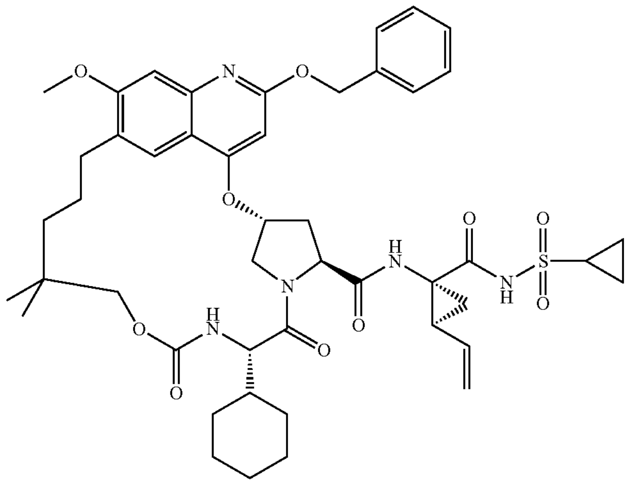 | (2R,4S,7S)-20-(benzyloxy)-7-cyclohexyl-N-((1R,2S)-1-[[(cyclopropylsulfonyl)amino]carbonyl]-2-vinylcyclopropyl)-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide | C1 | Benzyl bromide | Example 2 | 886.8 |
| 5 | 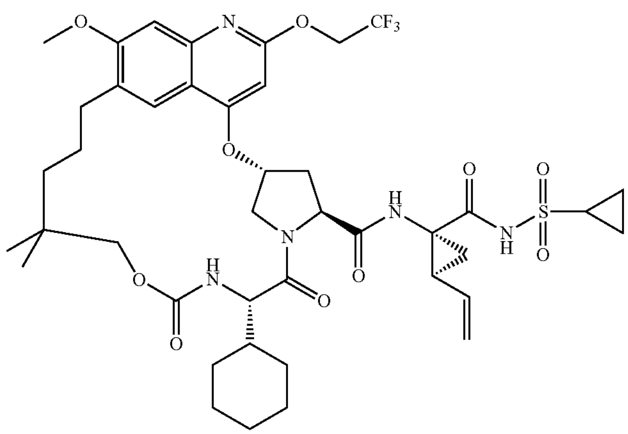 | (2R,4S,7S)-7-cyclohexyl-N-((1R,2S)-1-[[(cyclopropylsulfonyl)amino]carbonyl]-2-vinylcyclopropyl)-23-methoxy-12,12-dimethyl-6,9-dioxo-20-(2,2,2-trifluoroethoxy)-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide | C1 | 2,2,2-trifluoroethyl trifluoromethane sulfonate | Example 2 | 878.7 |

-continued

| Ex. | Structure | Name | Int. | Alkylating agent | Procedure | LRMS (M + H)+ |
|---|---|---|---|---|---|---|
| 6 | 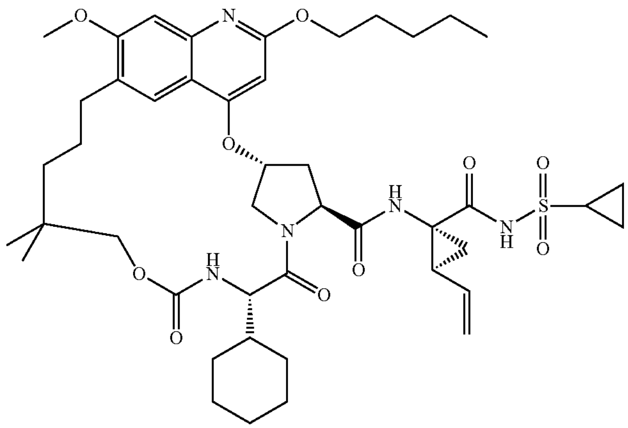 | (2R,4S,7S)-7-cyclohexyl-N-((1R,2S)-1-[[(cyclopropylsulfonyl)amino]carbonyl]-2-vinylcyclopropyl)-23-methoxy-12,12-dimethyl-6,9-dioxo-20-(pentyloxy)-3,4,6,7,8,9,12,13,14,15-decahydro-2H-16,18-(ethanediylidene)-2,5-methanopyrido[4,3-k][1,10,3,6]dioxadiazacyclononadecine-4-carboxamide | C1 | Pentyl iodide | Example 2 | 866.8 |
| 7 | 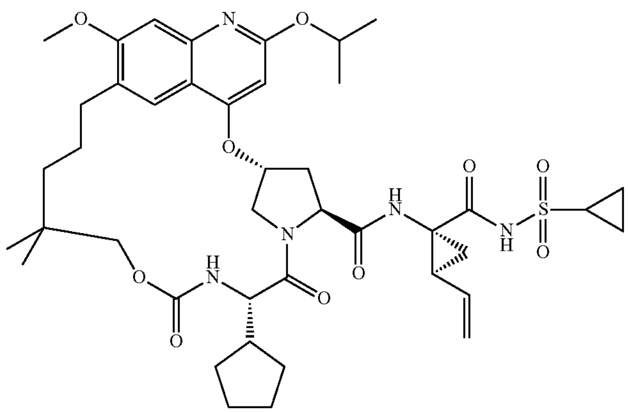 | (2R,4S,7S)-7-cyclohexyl-N-((1R,2S)-1-[[(cyclopropylsulfonyl)amino]carbonyl]-2-vinylcyclopropyl)-20-isopropoxy-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide | C1 | 2-iodopropane | Example 2 | 838.6 |

-continued

| Ex. | Structure | Name | Int. | Alkylating agent | Procedure | LRMS (M + H)+ |
|---|---|---|---|---|---|---|
| 8 | 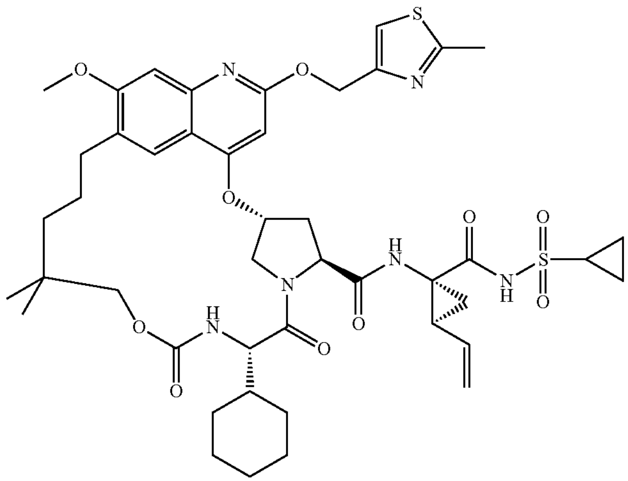 | (2R,4S,7S)-7-cyclohexyl-N-((1R,2S)-1-[[(cyclopropylsulfonyl)amino]carbonyl]-2-vinylcyclopropyl]-23-methoxy-]12,12-dimethyl-20-[(2-methyl-1,3-thiazol-4-yl)methoxy]-6,9-dioxo-3,4,6,7,8,9,12,13,14,15-decahydro-2H,11H-16,18-(ethanediylidene)-2,5-methanopyrido[4,3-k][1,10,3,6]dioxadiazacyclo nonadecine-4-carboxamide | C1 | 4-(chloromethyl)-2-methyl-1,3-thiazole | Example 2 | 907.7 |
| 9 | 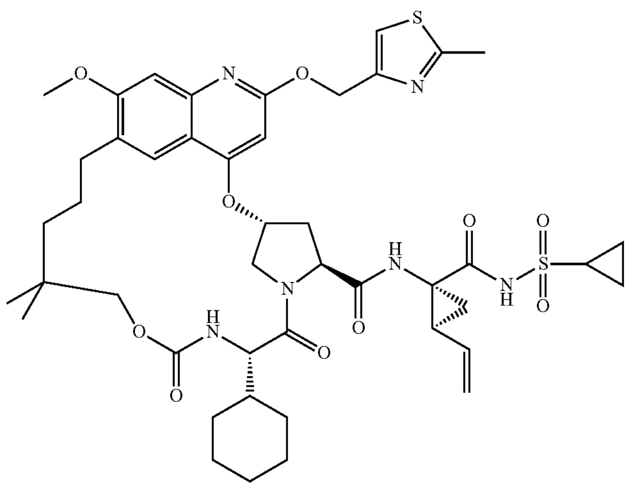 | (3R,5S,8S)-8-cyclopentyl-N-((1R,2S)-1-[[(cyclopropylsulfonyl)amino]carbonyl]-2-vinylcyclopropyl]-18-methoxy-13,13-dimethyl-22-[(2-methyl-1,3-thiazol-4-yl)methoxy]-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide | C3 | 4-(chloromethyl)-2-methyl-1,3-thiazole | Example 3 | 893.5 |

| Ex. | Structure | Name | Int. | Alkylating agent | Procedure | LRMS (M + H)+ |
|---|---|---|---|---|---|---|
| 10 | 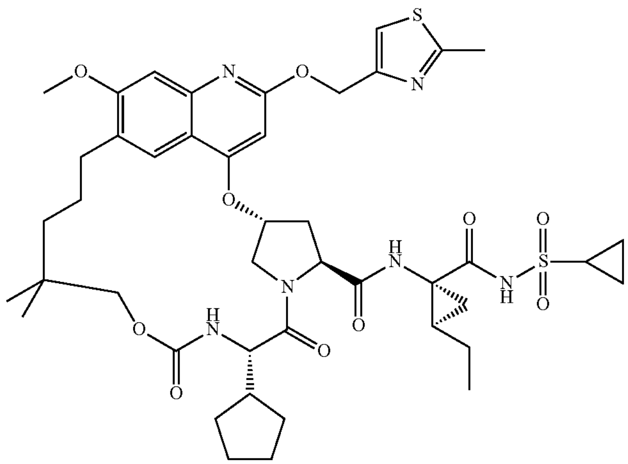 | (3R,5S,8S)-8-cyclopentyl-N-((1R,2R)-1-{[(cyclopropylsulfonyl)amino]carbonyl}-2-ethylcyclopropyl)-18-methoxy-13,13-dimethyl-22-[(2-methyl-1,3-thiazol-4-yl)methoxy]-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide | C3 | 4-(chloromethyl)-2-methyl-1,3-thiazole | Example 3 | 895.6 |
| 11 | 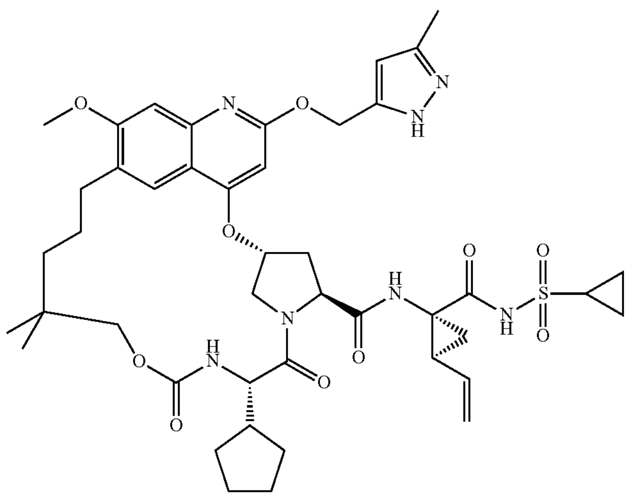 | (3R,5S,8S)-8-cyclopentyl-N-((1R,2S)-1-{[(cyclopropylsulfonyl)amino]carbonyl}-2-vinylcyclopropyl)-18-methoxy-13,13-dimethyl-22-[(3-methyl-1H-pyrazol-5-yl)methoxy]-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide | C3 | 5-(chloromethyl)-1,3-dimethyl-1H-pyrazole | Example 3 | 890.6 |

-continued

| Ex. | Structure | Name | Int. | Alkylating agent | Procedure | LRMS (M+H)+ |
|---|---|---|---|---|---|---|
| 12 | 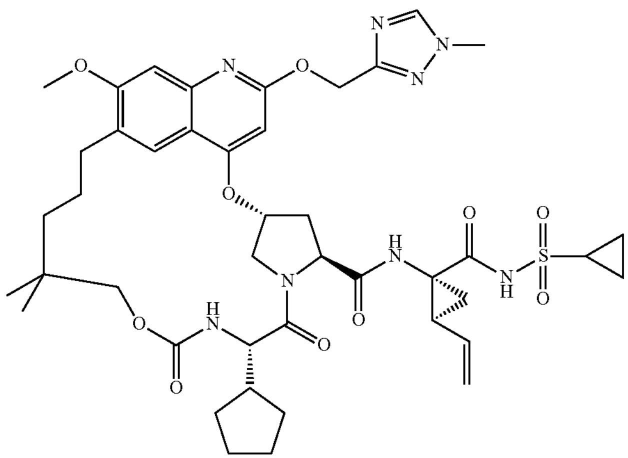 | (3R,5S,8S)-8-cyclopentyl-N-((1R,2S)-1-[[(cyclopropylsulfonyl)amino]carbonyl]-2-vinylcyclopropyl)-18-methoxy-13,13-dimethyl-22-[(1-methyl-1H-1,2,4-triazol-3-yl)methoxy]-7,10-dioxo-2,11-triaza-6,9,21-dioxatetracyclo[15.6.2.1$^{3,6}$.0$^{20,24}$]hexacosa-1(23),17,19,21,24-pentaene-5-carboxamide | C3 | 3-(chloromethyl)-1-methyl-1H-1,2,4-triazole | Example 3 | 877.5 |
| 13 | 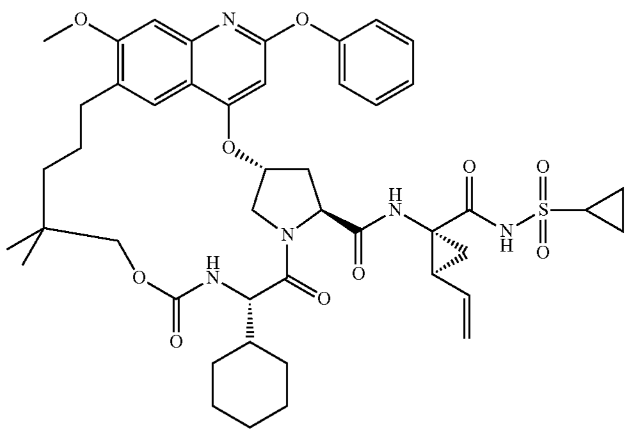 | (3R,5S,8S)-8-cyclohexyl-N-((1R,2S)-1-[[(cyclopropylsulfonyl)amino]carbonyl]-2-vinylcyclopropyl)-18-methoxy-13,13-dimethyl-7,10-dioxo-22-phenoxy-2,11-triazatetracyclo[15.6.2.1$^{3,6}$.0$^{20,24}$]hexacosa-1(23),17,19,21,24-pentaene-5-carboxamide | C1 | Diphenyl iodonium chloride | Example 2 | 872.4 |

| Ex. | Structure | Name | Int. | Alkylating agent | Procedure | LRMS (M + H)+ |
|---|---|---|---|---|---|---|
| 14 | 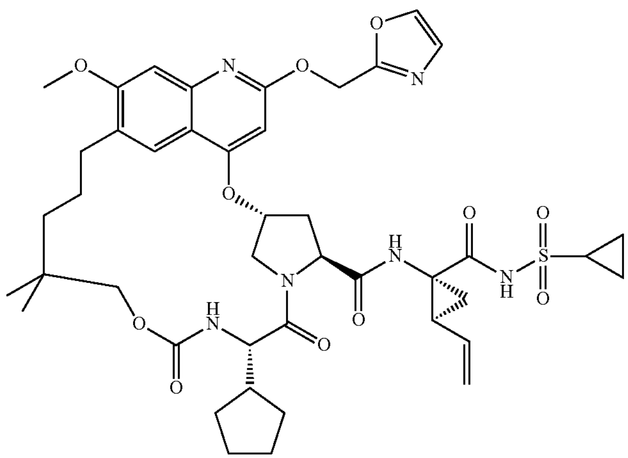 | (3R,5S,8S)-8-cyclopentyl-N-((1R,2S)-1-[[(cyclo-propylsulfonyl)amino]carbonyl]-2-vinylcyclopropyl)-18-methoxy-13,13-dimethyl-22-(1,3-oxazol-2-ylmethoxy)-7,10-dioxa-2,11-triazatetracyclo[15.6.2.1$^{3,6}$.0$^{20,24}$]hexacosa-1(23),17,19,21,24-pentaene-5-carboxamide | C3 | 2-(chloromethyl)-1,3-oxazole | Example 3 | 863.3 |
| 15 | 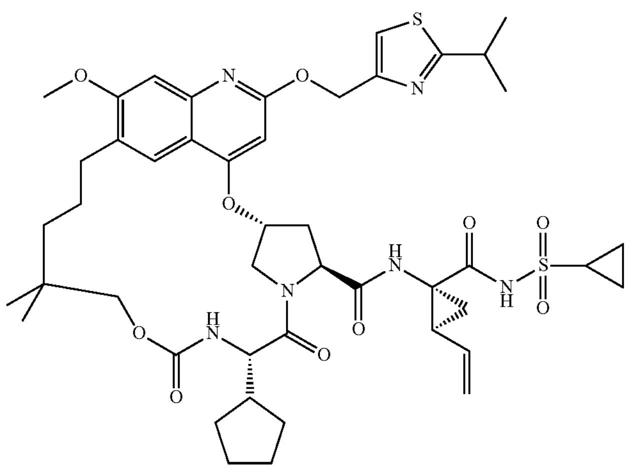 | (3R,5S,8S)-8-cyclopentyl-N-((1R,2S)-1-[[(cyclo-propylsulfonyl)amino]carbonyl]-2-vinylcyclopropyl)-22-[(2-isopropyl-1,3-thiazol-4-yl)methoxy]-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide | C3 | 4-(chloromethyl)-2-isopropyl-1,3-thiazole | Example 3 | 921.3 |

-continued

| Ex. | Structure | Name | Int. | Alkylating agent | Procedure | LRMS (M + H)+ |
|---|---|---|---|---|---|---|
| 16 | 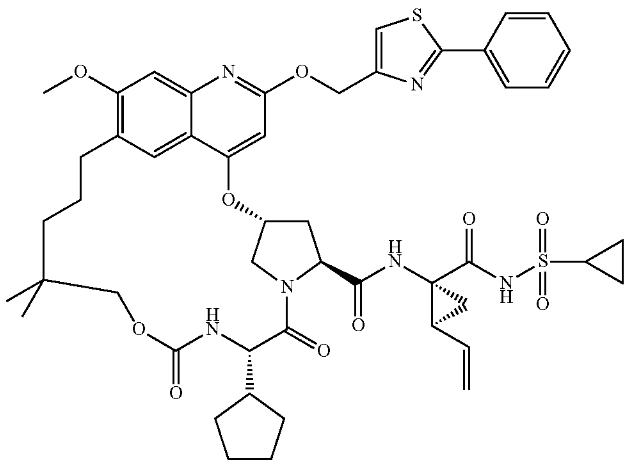 | (3R,5S,8S)-8-cyclopentyl-N-((1R,2S)-1-{[(cyclopropylsulfonyl)amino]carbonyl}-2-vinylcyclopropyl)-18-methoxy-13,13-dimethyl-7,10-dioxo-22-[(2-phenyl-1,3-thiazol-4-yl)methoxy]-2,11-dioxa-6,9,21-triazatetracyclo[15.6.2.1³,⁶.0²⁰,²⁴]hexacosa-1(23),17,19,21,24-pentaene-5-carboxamide | C3 | 4-(chloromethyl)-2-phenyl-1,3-thiazole | Example 3 | 955.3 |
| 17 | 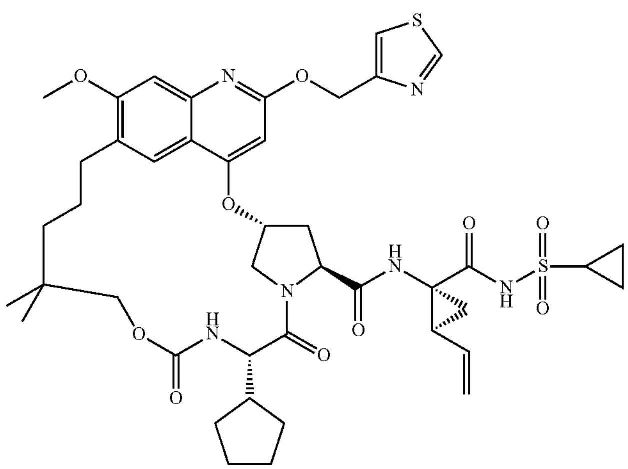 | (3R,5S,8S)-8-cyclopentyl-N-((1R,2S)-1-{[(cyclopropylsulfonyl)amino]carbonyl}-2-vinylcyclopropyl)-18-methoxy-13,13-dimethyl-7,10-dioxo-22-(1,3-thiazol-4-ylmethoxy)-2,11-dioxa-6,9,21-triazatetracyclo[15.6.2.1³,⁶.0²⁰,²⁴]hexacosa-1(23),17,19,21,24-pentaene-5-carboxamide | C3 | 4-(chloromethyl)-1,3-thiazole | Example 3 | 879.3 |

-continued

| Ex. | Structure | Name | Int. | Alkylating agent | Procedure | LRMS (M + H)+ |
|---|---|---|---|---|---|---|
| 18 | 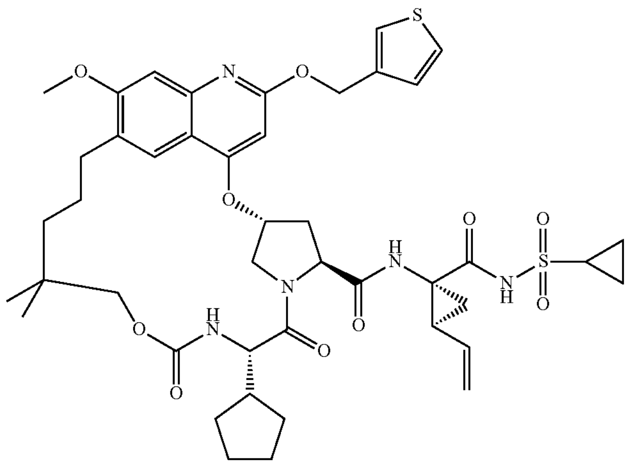 | (3R,5S,8S)-8-cyclopentyl-N-((1R,2S)-1-{[(cyclopropylsulfonyl)amino]carbonyl}-2-vinylcyclopropyl)-18-methoxy-13,13-dimethyl-7,10-dioxo-22-(3-thienylmethoxy)-2,11-dioxa-6,9,21-triazatetracyclo[15.6.2.1³,⁶.0²⁰,²⁴]hexacosa-1(23),17,19,21,24-pentaene-5-carboxamide | C3 | 3-(chloromethyl)thiophene | Example 3 | 878.3 |

Example 19

(2R,4S,7S)-7-cyclohexyl-20-(cyclopentyloxy)-N-((1R,2S)-1-{[(cyclopropylsulfonyl)amino]carbonyl}-2-vinylcyclopropyl)-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide

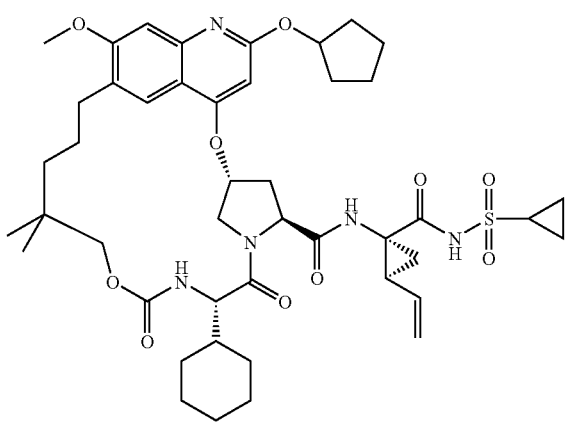

Step 1: (2R,4S,7S)-7-cyclohexyl-20-(cyclopentyloxy)-23-methoxy-12,12-dimethyl-6,9-dioxo-3,4,6,7,8,9,12,13,14,15-decahydro-2H,11H-16,18-etheno-2,5-methanopyrido[4,3-k][1,10,3,6]dioxadiazacyclononadecine-4-carboxylic acid

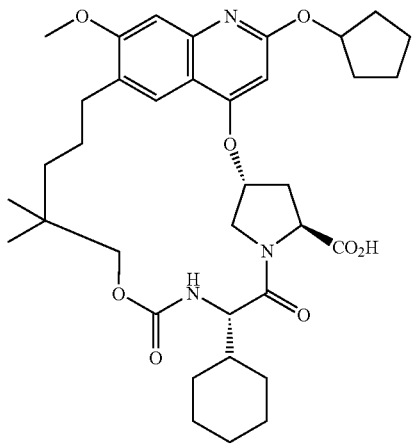

Ph$_3$P (88 mg, 0.335 mmol) and DIAD (0.065 ml, 0.335 mmol) were added to a solution of Intermediate C1 (50 mg, 0.084 mmol) and cyclopentanol (0.030 mL, 0.335 mmol) in THF (2 mL). The reaction mixture was stirred for 18 hours at RT, then water (0.5 mL) and MeOH (0.5 mL) were added, followed by LiOH (52.7 mg, 1.255 mmol). After 1 hour, 1N HCl and Et$_2$O were added; the product precipitated, and the solid was filtered off, dissolved in 10% MeOH/DCM and concentrated to give 29 mg of the title compound as a white solid. LRMS ESI$^+$ (M+H)$^+$ 652.5.

Step 2: (2R,4S,7S)-7-cyclohexyl-20-(cyclopentyloxy)-N-((1R,2S)-1-{[(cyclopropylsulfonyl)amino]carbonyl}-2-vinylcyclopropyl)-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide The title compound was prepared from the product from Step 1, according to the procedure in Example 1 Step 3. $^1$H NMR (500 MHz, CD$_3$OD): δ 9.31 (s, 1H), 7.75 (s, 1H), 7.08 (s, 1H), 6.90 (s, 1H), 5.86 (s, 1H), 5.75 (m, 1H), 5.48 (m, 1H), 5.28 (d, J=17.5 Hz, 1H), 5.12 (d, J=10.5 Hz, 1H), 4.66 (d, J=11.0 Hz, 1H), 4.45 (m, 1H), 4.31 (d, J=11.0 Hz, 1H), 4.24 (d, J=10.0 Hz, 1H), 4.08 (m, 1H), 4.01 (s, 3H), 3.27 (d, J=11.0 Hz, 1H), 3.17 (m, 1H), 2.94 (m, 1H), 2.65 (s, 1H), 2.57 (m, 1H), 2.29 (m, 1H), 2.21 (m, 2H), 2.07-1.49 (m, 16H), 1.40 (m, 1H), 1.34-1.20 (m, 8H), 1.10 (m, 2H), 1.05 (s, 3H), 0.98 (m, 1H), 0.76 (s, 3H). LRMS ESI$^+$ (M+H)$^+$ 864.6.

Example 20

(2R,4S,7S)-7-cyclohexyl-N-((1R,2S)-1-{[(cyclopropylsulfonyl)amino]carbonyl}-2-vinylcyclopropyl)-20-ethoxy-22-iodo-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide

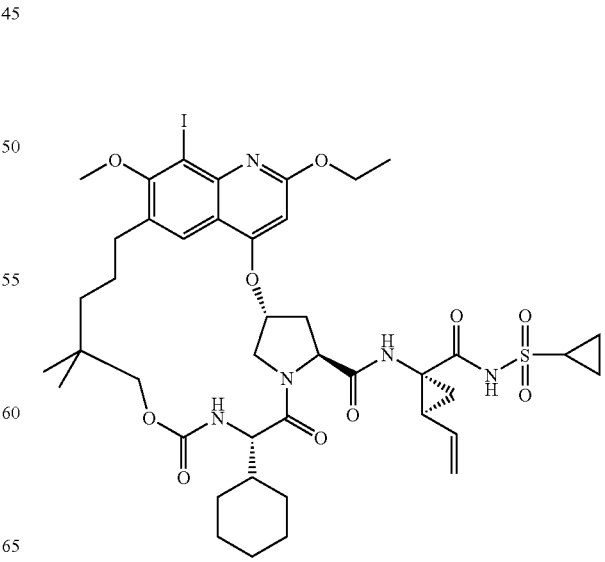

Step 1: Methyl (2R,4S,7S)-7-cyclohexyl-20-ethoxy-22-iodo-23-methoxy-12,12-dimethyl-6,9-dioxo-3,4,6,7,8,9,12,13,14,15-decahydro-2H,11H-16,18-etheno-2,5-methanopyrido[4,3-k][1,10,3,6]dioxadiazacyclononadecine-4-carboxylate

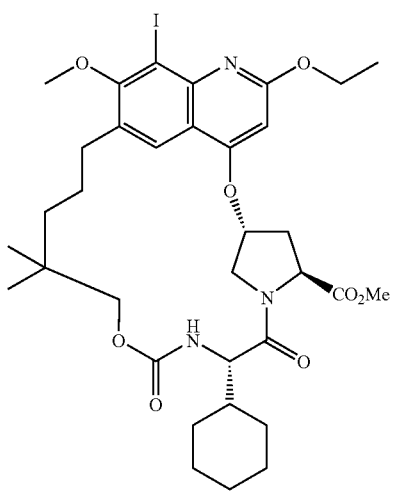

TfOH (0.18 mL, 2.0 mmol) and then NIS (49 mg, 0.22 mmol) were added to a solution of the product from Example 2 Step 1, (62 mg, 0.099 mmol) in DCM (10 mL). After 5 minutes, aqueous NaHCO₃ was added; the organic layer was separated and dried over MgSO₄; and the solvent was removed in vacuo. The residue was purified by reverse-phase chromatography (5-95% MeCN/0.15% aqueous TFA) to yield the title compound (52 mg) as a yellow solid. LRMS ESI⁺ (M+H)⁺ 752.4.

Step 2: (2R,4S,7S)-7-cyclohexyl-N-((1R,2S)-1-{[(cyclopropylsulfonyl)amino]carbonyl}-2-vinylcyclopropyl)-20-ethoxy-22-iodo-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide The title compound was prepared from the product of Step 1, according to the procedure in Example 1 Steps 2 and 3. $^1$H NMR (400 MHz, CDCl₃): 10.05 (s, 1H), 7.61 (s, 1H), 6.79 (s, 1H), 6.13 (s, 1H), 5.75 (m, 1H), 5.33 (d, J=9.6 Hz, 1H), 5.21 (m, 2H), 4.70 (d, J=10.4 Hz, 1H), 4.60 (q, J=6.8 Hz, 2H), 4.40 (d, J=10.8 Hz, 1H), 4.35 (t, J=9.6 Hz, 1H), 4.25 (m, 1H), 3.98 (m, 1H), 3.86 (s, 3H), 3.30 (d, J=10.8 Hz, 1H), 3.05 (m, 1H), 2.91 (m, 1H), 2.54 (m, 1H), 2.39 (m, 2H), 2.2-1.86 (m, 4H), 1.8-1.56 (m, 4H), 1.47 (t, J=7.2 Hz, 3H), 1.43-1.16 (m, 8H), 1.03 (m, 6H), 0.81 (s, 3H). LRMS ESI⁺ (M+H)⁺ 950.5.

Example 21

(3R,5S,8S)-8-cyclohexyl-N-((1R,2S)-1-{[(cyclopropylsulfonyl)amino]carbonyl}-2-vinylcyclopropyl)-22-ethoxy-19-ethyl-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide

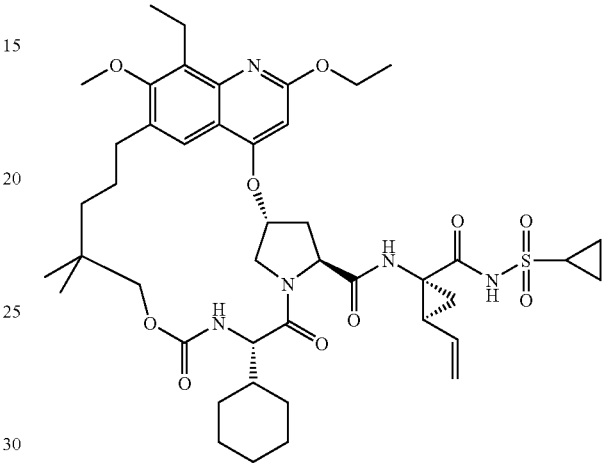

Step 1: Methyl (3R,5S,8S)-8-cyclohexyl-22-ethoxy-18-methoxy-13,13-dimethyl-7,10-dioxo-19-vinyl-2,11-dioxa-6,9,21-triazatetracyclo[15.6.2.1$^{3,6}$.0$^{20,24}$]hexacosa-1(23),17,19,21,24-pentaene-5-carboxylate Vinyltributyltin (0.014 mL, 0.047 mL) and Pd(Ph₃P)₄ (5 mg, 0.005 mmol) was added to a solution of the product from Example 20 Step 1 (35 mg, 0.047 mmol) in PhMe (5 mL). The mixture was heated to 95° C. for 2 hours; the solvent was removed in vacuo; and the crude material was purified on silica (gradient elution, 5-40% EtOAc/hexanes) to yield 25 mg of the title compound. LRMS ESI⁺ (M+H)⁺ 652.5; calcd for C₃₆H₅₀N₃O₈: 652.4.

Step 2: Methyl (3R,5S,8S)-8-cyclohexyl-22-ethoxy-19-ethyl-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxylate

Example 22

(3R,5S,8S)-19-chloro-8-cyclohexyl-N-((1R,2S)-1-{[(cyclopropylsulfonyl)amino]carbonyl}-2-vinylcyclopropyl)-22-ethoxy-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide

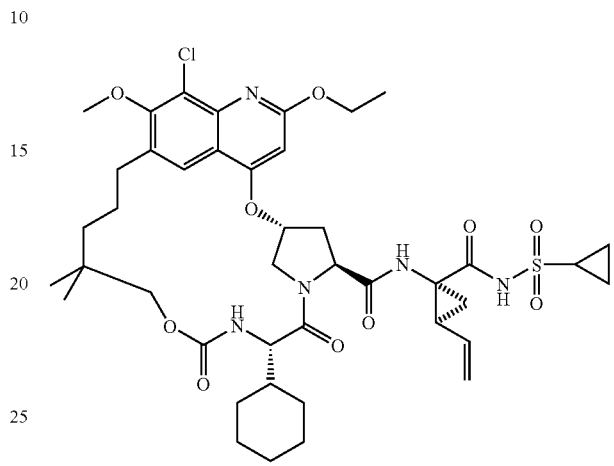

The title compound was prepared according to Example 20 using N-chlorosuccinimide in Step 1. $^1$H NMR (400 MHz, CDCl$_3$) δ 10.05 (s, 1H), 7.54 (s, 1H), 6.81 (s, 1H), 6.14 (s, 1H), 5.74 (m, 1H), 5.31 (m, 1H), 5.21 (m, 2H), 5.11 (m, 1H), 4.69 (m, 1H), 4.58 (m, 1H), 4.40-4.31 (m, 2H), 4.29-4.20 (m, 1H), 3.97 (d, J=11.5 Hz, 1H), 3.90 (s, 3H), 3.04 (m, 1H), 2.92 (m, 1H), 2.54 (m, 1H), 2.42 (m, 1H), 2.30 (m, 1H), 2.00 (m, 2H), 1.92 (m, 2H), 1.80-1.61 (m, 4H), 1.57 (s, 6H), 1.52 (m, 3H), 1.40-1.09 (m, 7H), 1.03 (m, 4H), 0.89 (m, 2H), 0.80 (m, 2H) ppm. LRMS ESI$^+$ (M+H)$^+$ 858.3; calcd for C$_{42}$H$_{57}$ClN$_5$O$_{10}$S: 858.3.

Example 23

(3R,5S,8S,12R,16S,18E)-8-cyclopentyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),18,20,22,23,25,27-heptaene-5-carboxamide

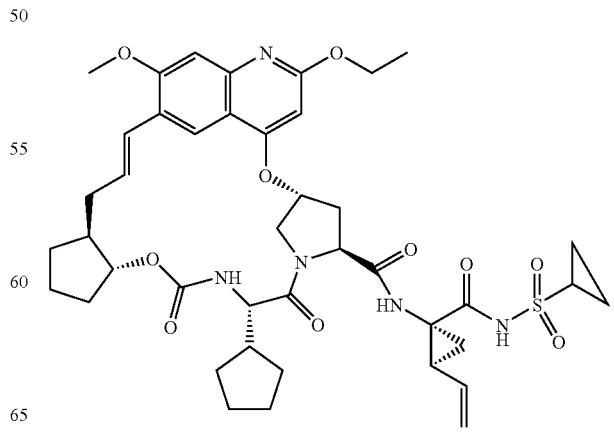

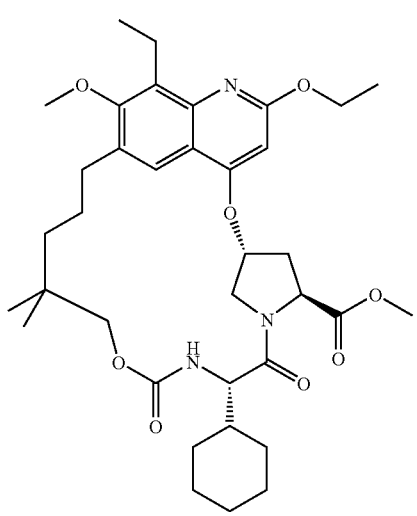

0% Pd/C (4 mg, 0.004 mmol) was added to a solution of the product from Step 1 (25 mg, 0.038 mmol) in EtOH (3 mL), and the mixture was placed under H$_2$. After 18 hours, the mixture was filtered through a pad of glass wool, and the solvent was removed in vacuo. LRMS ESI$^+$ (M+H)$^+$ 654.5; calcd for C$_{36}$H$_{52}$N$_3$O$_8$: 654.4.

Step 3: (3R,5S,8S)-8-cyclohexyl-N-((1R,2S)-1-{[(cyclopropylsulfonyl)amino]carbonyl}-2-vinylcyclopropyl)-22-ethoxy-19-ethyl-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide The title compound was prepared according to Steps 2 and 3 from Example 1. $^1$H NMR (400 MHz, CD$_3$OD) δ 7.57 (s, 1H), 6.30 (s, 1H), 5.82 (t, J=9.2 Hz, 1H), 5.34 (s, 1H), 5.16 (d, J=7.6 Hz, 1H), 4.99 (d, J=10.0 Hz, 1H), 4.57 (d, J=11.0 Hz, 2H), 4.48 (q, J=7.0 Hz, 2H), 4.46 (m, 1H), 4.32 (q, J=7.0 Hz, 2H), 4.16 (d, J=10.0 Hz, 1H), 3.78 (s, 3H), 3.11 (m, J=7.3 Hz, 2H), 2.96 (m, 1H), 2.81 (m, 1H), 2.61 (m, 1H), 2.29 (m, 3H), 1.82 (m, 2H), 1.76 (m, 7H), 1.70 (m, 1H), 1.52-1.42 (m, 3H), 1.41 (t, J=7.0 Hz, 3H), 1.30 (m, 7H), 1.07 (m, 5H), 0.87 (m, 2H), 0.81 (m, 3H) ppm. LRMS ESI$^+$ (M+H)$^+$ 852.4; calcd for C$_{44}$H$_{62}$N$_5$O$_{10}$S: 852.4.

Step 1: 1-t-Butyl 2-methyl (2S,4R)-4-[(2-ethoxy-7-methoxy-6-vinylquinolin-4-yl)oxy]pyrrolidine-1,2-dicarboxylate

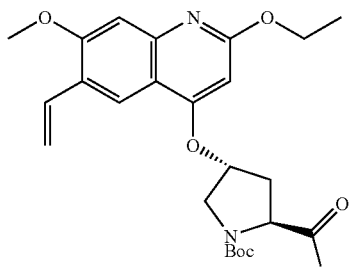

Et$_3$N (2.189 mL, 15.70 mmol) and PdCl$_2$(dppf)-DCM adduct (0.427 g, 0.523 mmol) were added to a solution of Intermediate C5 (5.50 g, 10.47 mmol) and potassium vinyltrifluoroborate (2.103 g, 15.70 mmol) in EtOH (105 mL). The reaction was heated to reflux for 3 hours. The EtOH was removed in vacuo, and the residue was taken up in EtOAc and washed with water. The organic layer was then dried over MgSO$_4$, and the solvent was removed in vacuo. The crude product was purified on silica (gradient elution, 0-50% EtOAc/hexane) to yield 3.90 g of the title compound. LRMS ESI$^+$ (M+H)$^+$ 473.1, calcd for C$_{25}$H$_{33}$N$_2$O$_7$: 473.2.

Step 2: Methyl (4R)-4-[(2-ethoxy-7-methoxy-6-vinylquinolin-4-yl)oxy]-L-prolinate dihydrochloride

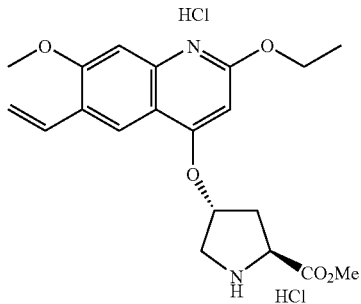

HCl (g) was bubbled for 10 minutes through a solution of the product from Step 1 (3.90 g, 8.25 mmol) in DCM (83 mL). The solution stirred for 1 hour, and the DCM was removed in vacuo to give 3.55 g of the title compound as a white powder. LRMS ESI$^+$ (M+H−2(HCl))$^+$ 373.1, calcd for C$_{20}$H$_{25}$N$_2$O$_5$: 373.2.

Step 3: Methyl (4R)-1-{(2S)-2-[({[(1R,2S)-2-allyl-cyclopentyl]oxy}carbonyl)amino]-2-cyclopentylacetyl}-4-[(2-ethoxy-7-methoxy-6-vinylquinolin-4-yl)oxy]-L-prolinate

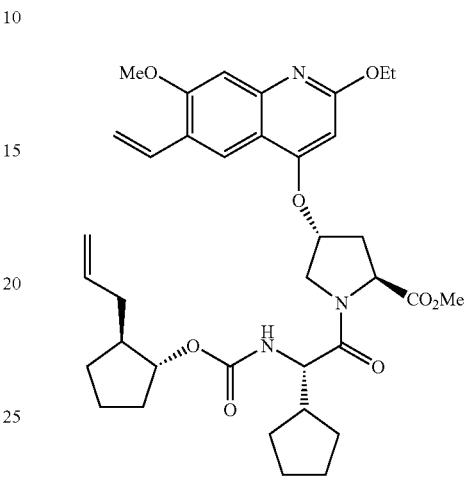

Intermediate B2 (3.20 g, 10.83 mmol), DMA (9.46 mL, 54.2 mmol), and HATU (4.94 g, 13.0 mmol) were added to a solution of the product from Step 2 (4.52 g, 11.0 mmol) in DMF (25 mL). After 1 hour, the mixture was extracted with water and EtOAc. The organic layer was washed with water and brine and dried over MgSO$_4$. The solvent was removed in vacuo, and the crude product was purified on silica (gradient elution, 0-40% EtOAc/hexane) to yield the title compound. LRMS ESI$^+$ (M+H)$^+$ 650.1, calcd for C$_{36}$H$_{48}$N$_3$O$_8$: 650.3.

Step 4: Methyl (6R,8S,11S,14aR,17aS,19E)-11-cyclopentyl-3-ethoxy-23-methoxy-10,13-dioxo-7,8,10,11,12,13,14a,15,16,17,17a,18-dodecahydro-6H-1,21-(ethanediylidene)-6,9-methanocyclopenta[r]pyrido[4,3-k][1,10,3,6]dioxadiazacyclononadecine-8-carboxylate

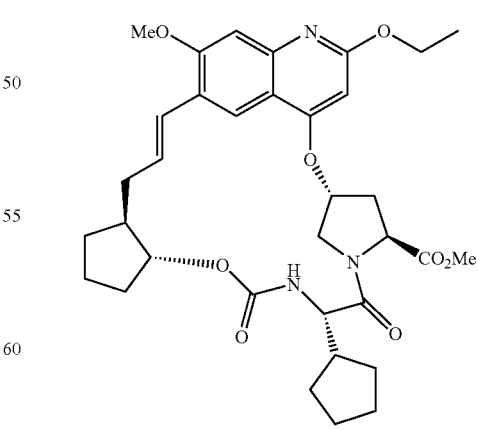

The Zhan 1b catalyst (66 mg, 0.09 mmol) was added to a solution of a portion of the product from Step 3 (2.85 g, 4.39 mmol) in DCE (500 mL). The reaction was heated to 70° C.

for 4 hours, then cooled to RT. After 17 hours at RT, the reaction was concentrated in vacuo, and the crude product was purified on silica (gradient elution, 0-40% EtOAc/hexane) to yield 2.48 g of the title compound. LRMS ESI+ (M+H)+ 622.1, calcd for $C_{34}H_{44}N_3O_8$: 622.3.

Step 5: (6R,8S,11S,14aR,17aS,19E)-11-cyclopentyl-3-ethoxy-23-methoxy-10,13-dioxo-7,8,10,11,12,13,14a,15,16,17,17a,18-dodecahydro-6H-1,21-(ethanediylidene)-6,9-methanocyclopenta[r]pyrido[4,3-k][1,10,3,6]dioxadiazacyclononadecine-8-carboxylic acid

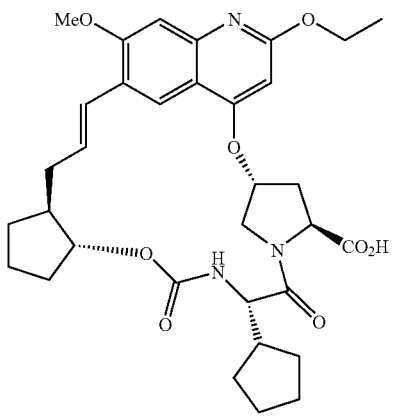

LiOH.H$_2$O (837 mg, 19.94 mmol) was added to a solution of a portion of the product from Step 4 (2.48 g, 3.99 mmol) in THF (4.0 mL), MeOH (4.0 mL) and water (2.0 mL). After 1 hour, 1N HCl and Et$_2$O were added. The organic layer was separated, and the aqueous layer was washed with EtOAc. The combined organic layers were dried over MgSO$_4$, and the solvent was removed in vacuo to yield 2.42 g of the title compound. LRMS ESI+ (M+H)+ 608.1, calcd for $C_{33}H_{42}N_3O_8$: 608.3.

Step 6: (3R,5S,8S,12R,16S,18E)-8-cyclopentyl-N-((1R,2S)-1-{[(cyclopropylsulfonyl)amino]carbonyl}-2-Vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),18,20,22,23,25,27-heptaene-5-carboxamide Intermediate A1 (379 mg, 1.42 mmol), DIEA (821 mL, 4.74 mmol), and HATU (278 mg, 1.18 mmol) were added to a solution of a portion of the product from Step 5 (1.79 g, 1.25 mmol) in DMF (5 mL). After 15 hours, the mixture was partitioned between EtOAc and 1N HCl. The organic layer was separated and dried over MgSO$_4$, and the solvent was removed in vacuo. The crude product was purified by reverse-phase HPLC (C-18), 30-95% MeCN in 0.15% aqueous TFA, eluting with MeCN/water and on silica (gradient elution, 0-10% acetone/DCM) to yield the title compound. LRMS ESI+ (M+H)+ 820.1, calcd for $C_{42}H_{54}N_5O_{10}S$: 820.3. $^1$H NMR (500 MHz) (CD$_3$OD) δ 8.17 (s, 1H), 7.16 (d, J=6.5 Hz, 1H), 7.07 (s, 1H), 6.70 (d, J=16 Hz, 1H), 6.32 (m, 1H), 6.24 (s, 1H), 5.72 (m, 1H), 5.34 (br s, 1H), 5.25 (dd, J=16 Hz, 1.5 Hz, 1H), 5.21 (d, J=4.5 Hz, 1H), 5.08 (dd, J=10.5 Hz, 1.5 Hz, 1H), 4.75 (d, J=12.0 Hz, 1H), 4.40 (q, J=7.0 Hz, 2H), 4.34 (dd, J=11.0 Hz, 6.5 Hz, 1H), 4.14 (d, J=10.5 Hz, 1H), 4.03 (dd, J=12.0 Hz, 3.5 Hz, 1H), 2.96 (m, 1H) 2.59 (dd, J=14.0 Hz, 6.5 Hz, 1H), 2.3-2.0 (m, 8H), 2.0-1.5 (m, 12H), 1.41 (t, J=7.0 Hz, 3H), 1.4-1.15 (m, 7H), 1.07 (m, 2H), 0.9 (m, 1H).

Example 24

(3R,5S,8S,12R,16R)-8-cyclopentyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),20,22,23,25,27-hexaene-5-carboxamide

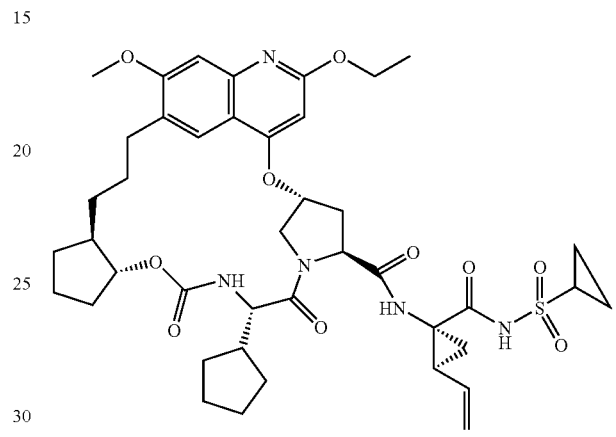

Step 1: Methyl (6R,8S,11S,14aR,17aR)-11-cyclopentyl-3-ethoxy-23-methoxy-10,13-dioxo-7,8,10,11,12,13,14a,15,16,17,17a,18,19,20-tetradecahydro-6H-1,21-etheno-6,9-methanocyclopenta[r]pyrido[4,3-k][1,10,3,6]dioxadiazacyclononadecine-8-carboxylate

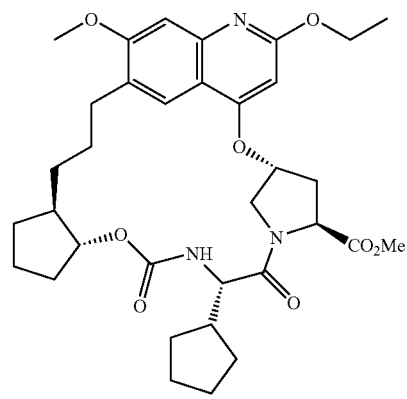

Pd/C (15 mg, 0.028 mmol) under nitrogen was added to a solution of a portion of the product from Example 23 Step 4 (150 mg, 0.252 mmol) in EtOH (5 mL). The reaction was then placed under H$_2$ overnight. The reaction was incomplete the following morning. The solution was filtered to remove palladium and re-submitted to same reaction conditions. After 3 hours, the reaction was filtered, and the solvent was removed in vacuo to give 100 mg of the title compound as a white solid. LRMS ESI+ (M+H)+ 624.2, calcd for $C_{34}H_{46}N_3O_8$: 624.3.

Step 2: (3R,5S,8S,12R,16R)-8-cyclopentyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),20,22,23,25,27-hexaene-5-carboxamide Using the product from Step 1, the title compound was prepared according to Example 23 Steps 5 and 6. $^1$H NMR (500 MHz, CD$_3$OD) δ 9.26 (s, 1H), 7.94 (s, 1H), 7.07 (s, 1H), 6.73 (s, 1H), 5.77-5.68 (m, 2H), 5.26 (d, J=17.5 Hz, 1H), 5.11 (d, J=12 Hz, 1H), 4.97 (bs, 1H), 4.58 (q, J=7 Hz, 1H), 4.41-4.37 (m, 1H), 4.15-4.09 (m, 2H), 4.00 (s, 2H), 2.97 (m, 1H), 2.72 (m, 1H), 2.65-2.57 (m, 2H), 2.34 (m, 2H), 2.18-1.88 (m, 5H), 1.87-1.72 (m, 8H), 1.54 (t, J=7 Hz, 1H), 1.40-1.21 (m, 7H), 1.90 (m, 1H), 1.09-0.88 (m, 2H). LRMS ESI$^+$ (M+H)$^+$ 822.1, calcd for C$_{42}$H$_{56}$N$_5$O$_{10}$S: 822.3.

The following compounds were prepared according to procedure in the referenced Example using the appropriate Intermediate B and C. Compounds that utilized Intermediates B4, B7, B11, B12, B13, B14, and B15 produced diastereomers, which were separated in the final step by reverse-phase HPLC.

| Ex. | Structure | Name | Int. B/C | Example | LRMS (M + H)$^+$ |
|---|---|---|---|---|---|
| 26 | 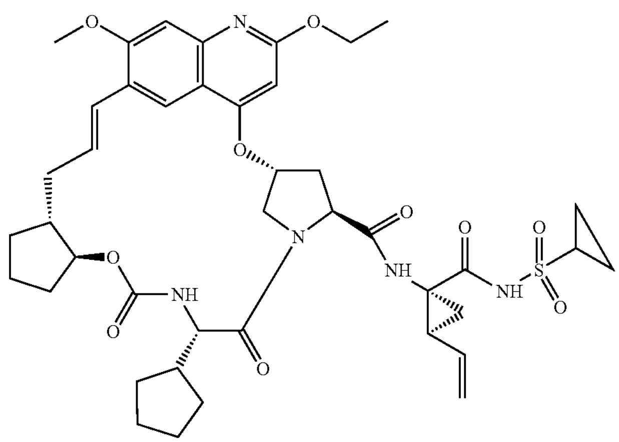 | (3R,5S,8S,12S,16R,18E)-8-cyclopentyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),18,20,22,23,25,27-heptaene-5-carboxamide | B3/C5 | 23 | 820.0 |
| 27 | 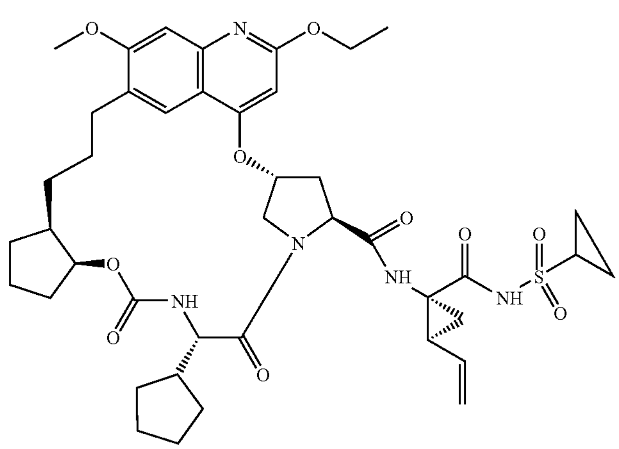 | (3R,5S,8S,12S,16R)-8-cyclopentyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),20,22,23,25,27-hexaene-5-carboxamide | B4/C5 | 24 | 822.3 |

-continued

| Ex. | Structure | Name | Int. B/C | Example | LRMS (M + H)+ |
|---|---|---|---|---|---|
| 28 | 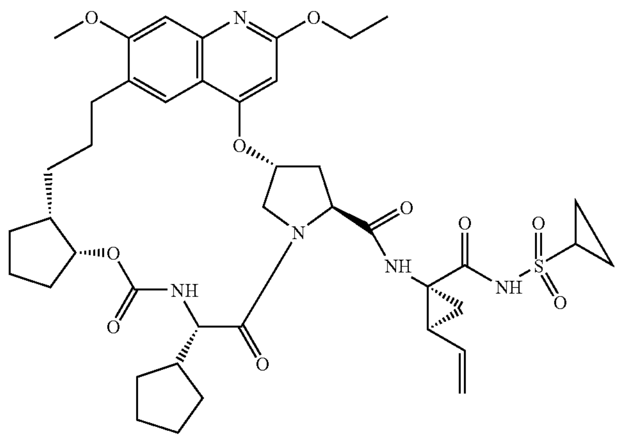 | (3R,5S,8S,12S,16S)-8-cyclopentyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),20,22,23,25,27-hexaene-5-carboxamide | B4/C5 | 24 | 822.3 |
| 29 | 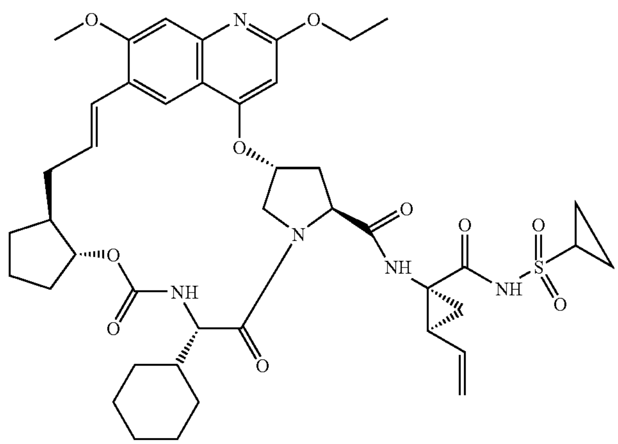 | (3R,5S,8S,12S,16S,18E)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),18,20,22,23,25,27-heptaene-5-carboxamide | B7/C5 | 23 | 834.4 |
| 30 | 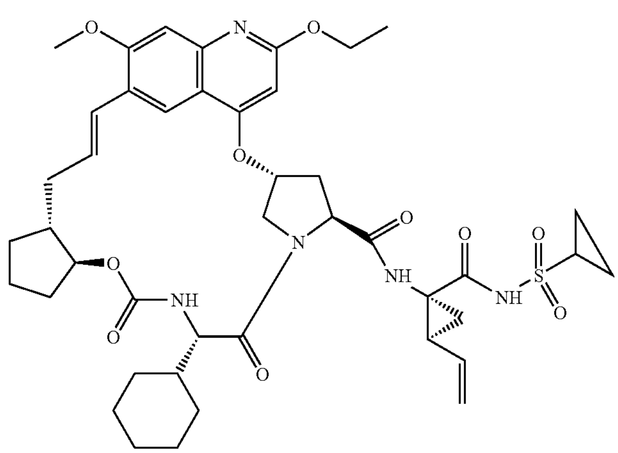 | (3R,5S,8S,12S,16R,18E)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),18,20,22,23,25,27-heptaene-5-carboxamide | B7/C5 | 23 | 834.5 |

| Ex. | Structure | Name | Int. B/C | Example | LRMS (M + H)+ |
|---|---|---|---|---|---|
| 31 | 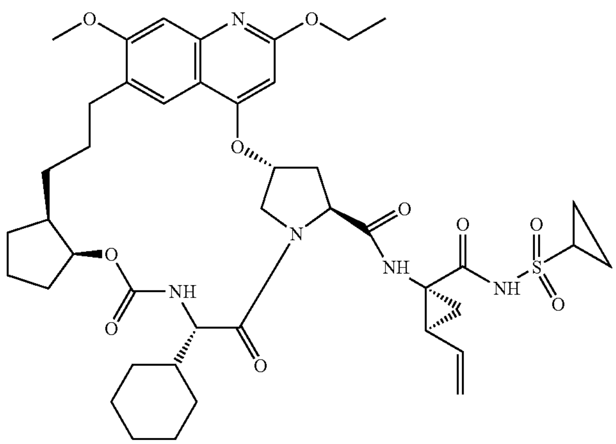 | (3R,5S,8S,12S,16R)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),20,22,23,25,27-hexaene-5-carboxamide | B7/C5 | 24 | 836.5 |
| 32 | 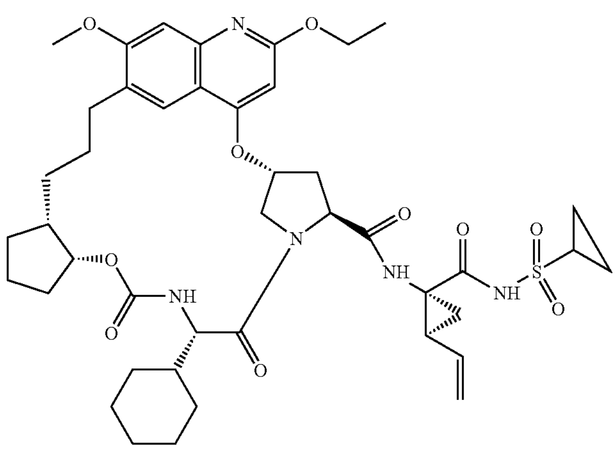 | (3R,5S,8S,12R,16S)-8-cyclohexyl-N-((1R,2S)-1-{[(cyclopropylsulfonyl)amino]carbonyl}-2-vinylcyclopropyl)-25-ethoxy-21-methoxy-7,10-dioxo-2,11-dioxa-6,9,24-triazapentacyclo[18.6.2.1$^{3,6}$.0$^{12,16}$.0$^{23,27}$]nonacosa-1(27),20,22,23,25,27-hexaene-5-carboxamide | B7/C5 | 24 | 836.5 |
| 33 | 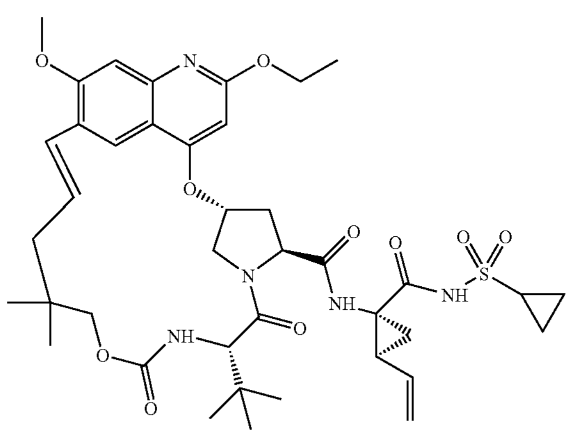 | (3R,5S,8S,15E)-8-t-butyl-N-((1R,2S)-1-{[(cyclopropylsulfonyl)amino]carbonyl}-2-vinylcyclopropyl)-22-ethoxy-18-methoxy-13,13-dimethyl-7,10-dioxo-2,11-dioxa-6,9,21-triazatetracyclo[15.6.2.1$^{3,6}$.0$^{20,24}$]hexacosa-1(23),15,17,19,21,24-hexaene-5-carboxamide | B8/C5 | 23 | 796.5 |

| Ex. | Structure | Name | Int. B/C | Example | LRMS (M + H)+ |
|---|---|---|---|---|---|
| 34 | 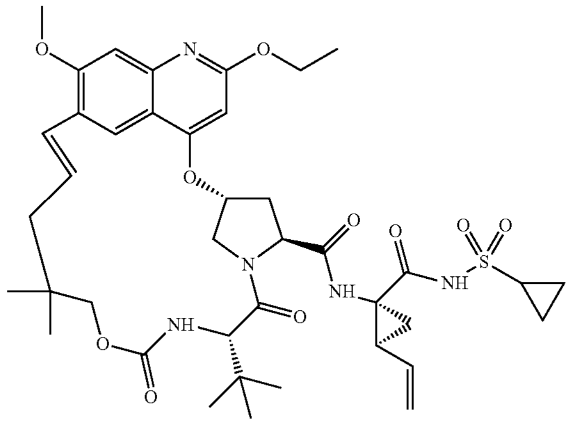 | (3R,5S,8S)-8-t-butyl-N-((1R,2S)-1-{[(cyclopropylsulfonyl)amino]carbonyl}-2-vinyl-cyclopropyl)-22-ethoxy-18-methoxy-13,13-dimethyl-7,10-dioxo-2,11-dioxa-6,9,21-triaza-tetracyclo[15.6.2.1$^{3,6}$•0$^{20,24}$]hexacosa-1(23),17,19,21,24-pentaene-5-carboxamide | B8/C5 | 24 | 798.5 |
| 35 | 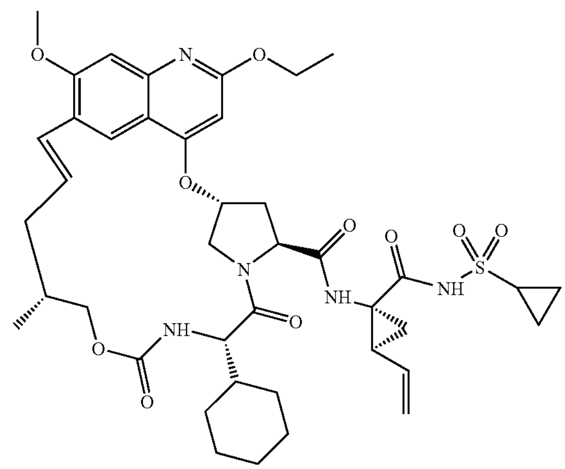 | (3R,5S,8S,13R,15E)-8-cyclohexyl-N-((1R,2S)-1-{[(cyclopropylsulfonyl)amino]carbonyl}-2-vinylcyclopropyl)-22-ethoxy-18-methoxy-13-methyl-7,10-dioxo-2,11-dioxa-6,9,21-triazatetracyclo[15.6.2.1$^{3,6}$•0$^{20,24}$]hexacosa-1(23),15,17,19,21,24-hexaene-5-carboxamide | B9/C5 | 23 | 808.4 |
| 36 | 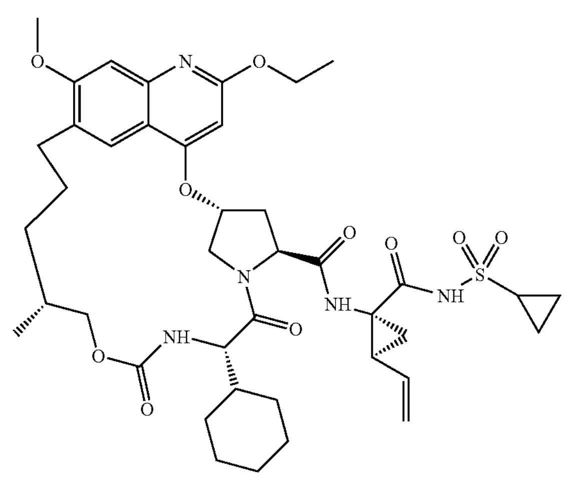 | (3R,5S,8S,13R)-8-cyclohexyl-N-((1R,2S)-1-{[(cyclopropyl-sulfonyl)amino]carbonyl}-2-vinylcyclopropyl)-22-ethoxy-18-methoxy-13-methyl-7,10-dioxo-2,11-dioxa-6,9,21-triazatetracyclo[15.6.2.1$^{3,6}$•0$^{20,24}$]hexacosa-1(23),17,19,21,24-pentaene-5-carboxamide | B9/C5 | 24 | 810.5 |

| Ex. | Structure | Name | Int. B/C | Example | LRMS (M + H)+ |
|---|---|---|---|---|---|
| 37 | 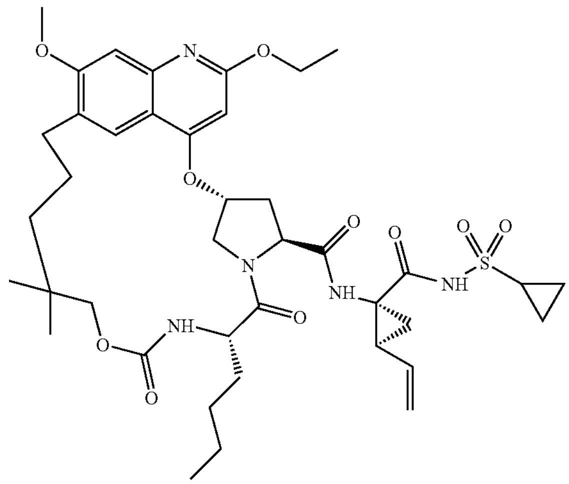 | (3R,5S,8S,)-8-butyl-N-((1R,2S)-1-{[(cyclopropylsulfonyl)amino]carbonyl}-2-vinylcyclopropyl)-22-ethoxy-18-methoxy-13,13-dimethyl-7,10-dioxo-2,11-dioxa-6,9,21-triazatetracyclo[15.6.2.1$^{3,6}$•O$^{20,24}$]hexacosa-1(23),17,19,21,24-pentaene-5-carboxamide | B10/C5 | 24 | 798.4 |
| 38 | 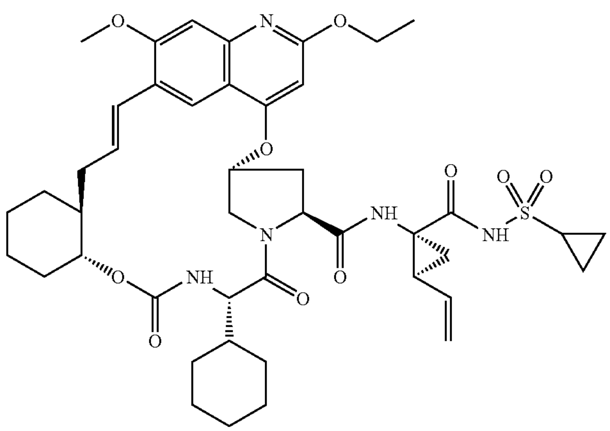 | (3R,5S,8S,12R,17S,19E)-8-cyclohexyl-N-((1R,2S)-1-{[(cyclopropylsulfonyl)amino]carbonyl}-2-vinylcyclopropyl)-26-ethoxy-22-methoxy-7,10-dioxo-2,11-dioxa-6,9,25-triazapentacyclo[19.6.2.1$^{3,6}$•O$^{12,17}$•O$^{24,28}$]triaconta-1(28),19,21,23,24,26,28-heptaene-5-carboxamide | B11/C5 | 23 | 848.4 |
| 39 | 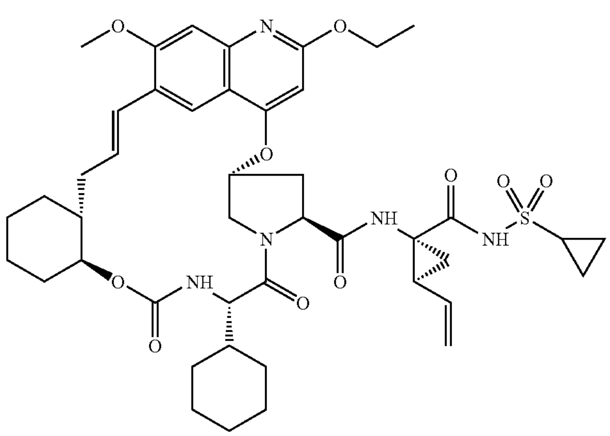 | (3R,5S,8S,12S,17R,19E)-8-cyclohexyl-N-((1R,2S)-1-{[(cyclopropylsulfonyl)amino]carbonyl}-2-vinylcyclopropyl)-26-ethoxy-22-methoxy-7,10-dioxo-2,11-dioxa-6,9,25-triazapentacyclo[19.6.2.1$^{3,6}$•O$^{12,17}$•O$^{24,28}$]triaconta-1(28),19,21,23,24,26,28-heptaene-5-carboxamide | B11/C5 | 23 | 848.5 |

-continued

| Ex. | Structure | Name | Int. B/C | Example | LRMS (M + H)+ |
|---|---|---|---|---|---|
| 40 | 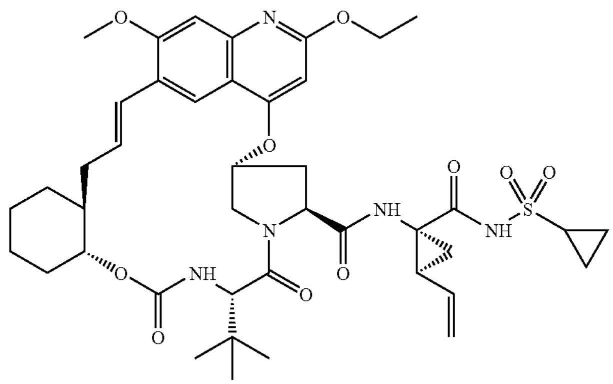 | (3R,5S,8S,12R,17S,19E)-8-t-butyl-N-((1R,2S)-1-{[(cyclo-propylsulfonyl)amino]carbonyl}-2-vinylcyclopropyl)-26-ethoxy-22-methoxy-7,10-dioxo-2,11-dioxa-6,9,25-triazapentacyclo[19.6.2.1$^{3,6}$•0$^{12,17}$•0$^{24,28}$]triaconta-1(28),19,21,23,24,26,28-heptaene-5-carboxamide | B13/C5 | 23 | 822.4 |
| 41 | 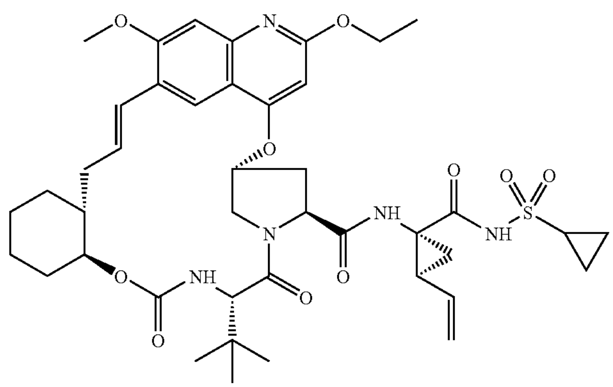 | (3R,5S,8S,12S,17R,19E)-8-t-butyl-N-((1R,2S)-1-{[(cyclo-propylsulfonyl)amino]carbonyl}-2-vinylcyclopropyl)-26-ethoxy-22-methoxy-7,10-dioxo-2,11-dioxa-6,9,25-triazapentacyclo[19.6.2.1$^{3,6}$•0$^{12,17}$•0$^{24,28}$]triaconta-1(28),19,21,23,24,26,28-heptaene-5-carboxamide | B13/C5 | 23 | 822.4 |
| 42 | 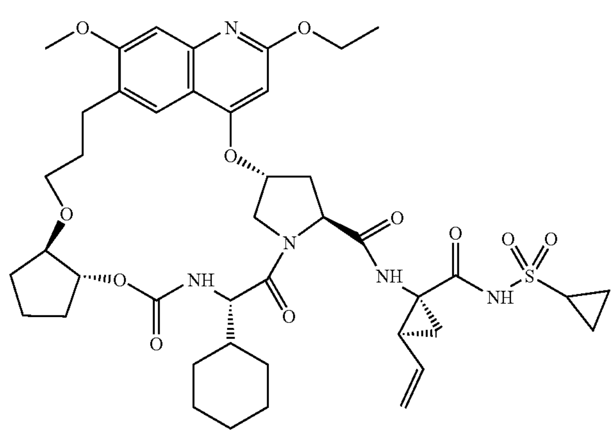 | (3R,5S,8S,12R,16R)-8-cyclohexyl-N-((1R,2S)-1-{[(cyclopropylsulfonyl)amino]carbonyl}-2-vinylcyclopropyl)-26-ethoxy-22-methoxy-7,10-dioxo-2,11-dioxa-6,9,25-triazapentacyclo[19.6.2.1$^{3,6}$•0$^{12,17}$•0$^{24,28}$]triaconta-1(28),19,21,23,24,26,28-hexaene-5-carboxamide | B12/C5 | 24 | 852.1 |

| Ex. | Structure | Name | Int. B/C | Example | LRMS (M + H)+ |
|---|---|---|---|---|---|
| 43 | 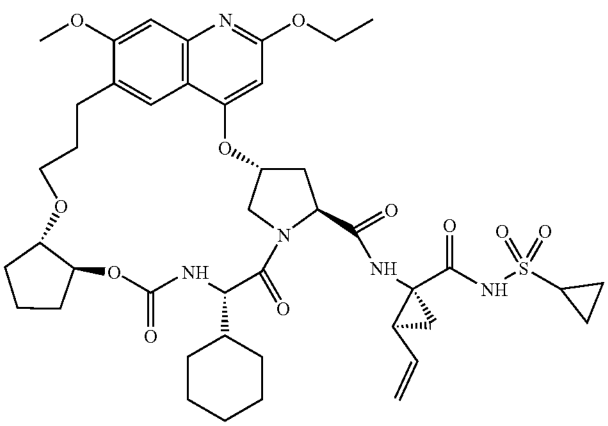 | (3R,5S,8S,12S,16S)-8-cyclohexyl-N-((1R,2S)-1-{[(cyclopropylsulfonyl)amino]carbonyl}-2-vinylcyclopropyl)-26-ethoxy-22-methoxy-7,10-dioxo-2,11,17-trioxa-6,9,25-triazapentacyclo[19.6.2.1$^{3,6}$.0$^{12,16}$.0$^{24,28}$]triaconta-1(28),21,23,24,26,28-hexaene-5-carboxamide | B12/C5 | 24 | 852.1 |
| 44 | 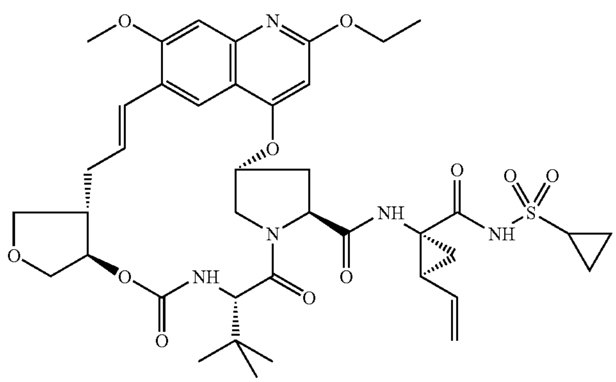 | (3R,5S,8S,12R,16S,18E)-8-t-butyl-N-((1R,2S)-1-{[(cyclo-propylsulfonyl)amino]carbonyl}-2-vinylcyclopropyl)-25-ethoxy-21-methoxy-7,10-dioxo-2,11,14-trioxa-6,9,24-triazapentacyclo[18.6.2.1$^{3,6}$.0$^{12,16}$.0$^{24,28}$]noncosa-1(27),18,20,22,23,25,27-heptaene-5-carboxamide | B14/C5 | 23 | 810.5 |
| 45 | 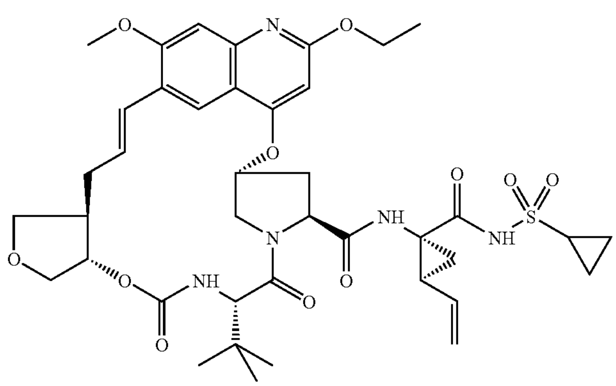 | (3R,5S,8S,12S,16R,18E)-8-t-butyl-N-((1R,2S)-1-{[(cyclo-propylsulfonyl)amino]carbonyl}-2-vinylcyclopropyl)-25-ethoxy-21-methoxy-7,10-dioxo-2,11,14-trioxa-6,9,24-triazapentacyclo[18.6.2.1$^{3,6}$.0$^{12,16}$.0$^{23,27}$]nonacosa-1(27),18,20,22,23,25,27-heptaene-5-carboxamide | B14/C5 | 23 | 810.5 |
| 46 | 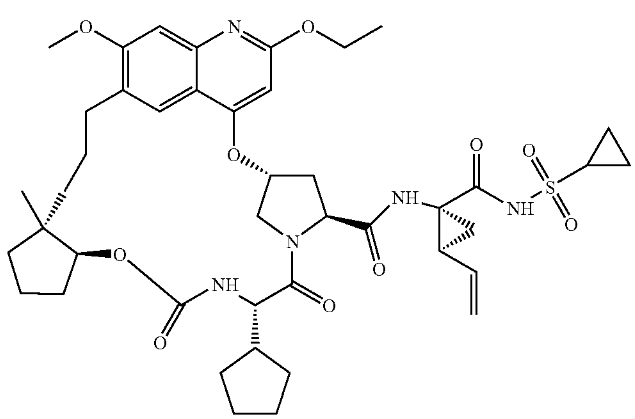 | (3R,5S,8S,12S,16S)-8-cyclopentyl-N-((1R,2S)-1-{[(cyclopropylsulfonyl)amino]carbonyl}-2-vinylcyclopropyl)-25-ethoxy-21-methoxy-16-methyl-7,10-dioxo-2,11-dioxa-6,9,24-triazapentacyclo[18.6.2.1$^{3,6}$.0$^{12,16}$.0$^{23,27}$]nonacosa-1(26),20,22,24,27-pentaene-5-carboxamide | B15/C5 | 24 | 836.7 |

-continued

| Ex. | Structure | Name | Int. B/C | Example | LRMS (M + H)+ |
|---|---|---|---|---|---|
| 47 | 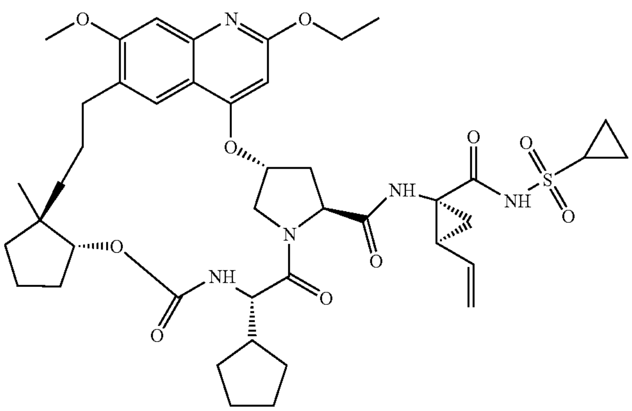 | (3R,5S,8S,12R,16R)-8-cyclopentyl-N-((1R,2S)-1-{[(cyclopropylsulfonyl)amino]carbonyl}-2-vinylcyclopropyl)-25-ethoxy-21-methoxy-16-methyl-7,10-dioxo-2,11-dioxa-6,9,24-triazapentacyclo[18.6.2.1$^{3,6}$.0$^{12,16}$.0$^{23,27}$]nonacosa-1(26),20,22,24,27-pentaene-5-carboxamide | B15/C5 | 24 | 836.7 |
| 48 | 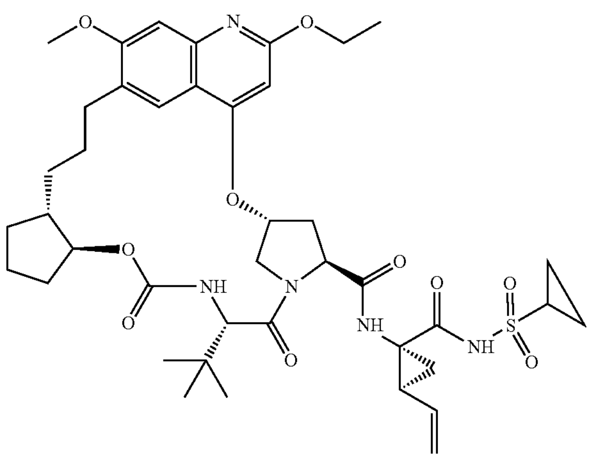 | (3R,5S,8S,12S,16S)-8-t-butyl-N-((1R,2S)-1-{[(cyclopropylsulfonyl)amino]carbonyl}-2-vinylcyclopropyl)-25-ethoxy-21-methoxy-16-methyl-7,10-dioxo-2,11-dioxa-6,9,24-triazapentacyclo[18.6.2.1$^{3,6}$.0$^{12,16}$.0$^{23,27}$]nonacosa-1(27),20,22,23,25,27-hexaene-5-carboxamide | B17/C5 | 24 | 810.5 |
| 49 | 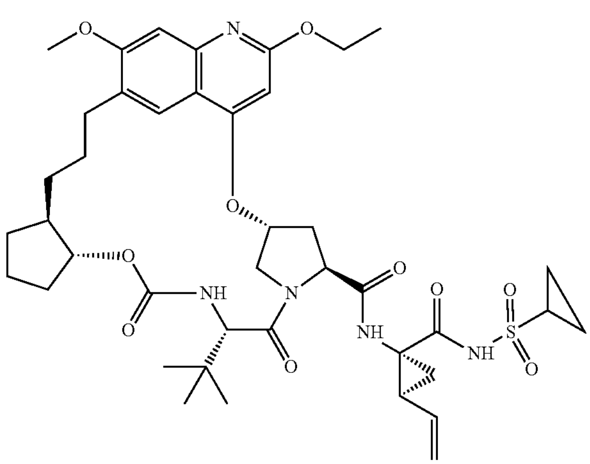 | (3R,5S,8S,12R,16R)-8-t-butyl-N-((1R,2S)-1-{[(cyclopropylsulfonyl)amino]carbonyl}-2-vinylcyclopropyl)-25-ethoxy-21-methoxy-16-methyl-7,10-dioxo-2,11-dioxa-6,9,24-triazapentacyclo[18.6.2.1$^{3,6}$.0$^{12,16}$.0$^{23,27}$]nonacosa-1(27),20,22,23,25,27-hexaene-5-carboxamide | B16/C5 | 24 | 810.6 |

US 8,309,540 B2

| Ex. | Structure | Name | Int. B/C | Example | LRMS (M + H)+ |
|---|---|---|---|---|---|
| 50 | 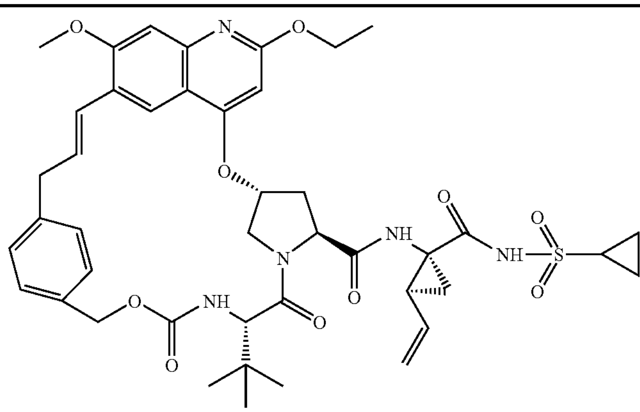 | (3R,5S,8S,18E)-8-t-butyl-N-((1R,2S)-1-{[(cyclopropylsulfonyl)amino]carbonyl}-2-vinylcyclopropyl)-25-ethoxy-21-methoxy-16-methyl-7,10-dioxo-2,11-dioxa-6,9,24-triazapentacyclo[18.6.2.2$^{13,16}$•1$^{3,6}$•0$^{23,27}$]hentriaconta-1(27),13,15,18,20,22,23,25,27,29-decaene-5-carboxamide | B18/C5 | 23 | 830.1 |

Example 51

(6R,8S,11S,17aR,18aS)-11-cyclopentyl-N-((1R,2S)-1-{[(cyclopropylsulfonyl)amino]carbonyl}-2-vinylcyclopropyl)-3-ethoxy-21-methoxy-16,16-dimethyl-10,13-dioxo-7,8,10,11,12,13,15,16,17,17a,18,18a-dodecahydro-6H-1,19-etheno-6,9-methanocyclopropa[o]pyrido[4,3-k][1,10,3,6]dioxadiazacyclononadecine-8-carboxamide

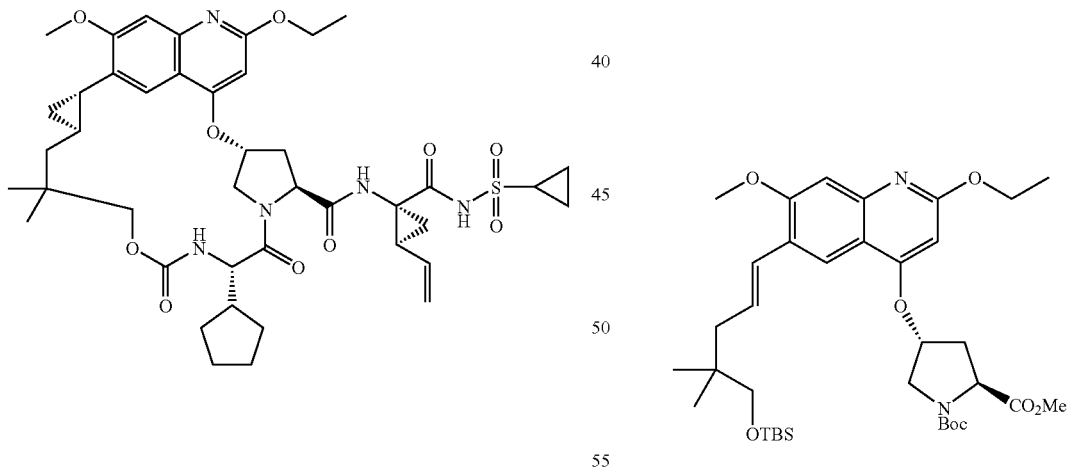

Step 1: ((1E)-5-{[t-Butyl(dimethyl)silyl]oxy}-4,4-dimethylpent-1-en-1-yl)boronic acid

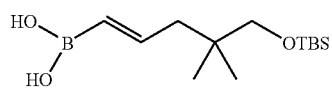

Br$_2$BH-SMe$_2$ (15.38 ml, 93 mmol) was added to a solution of t-butyl[(2,2-dimethylpent-4-yn-1-yl)oxy]dimethylsilane (20 g, 88 mmol) in DCM (126 ml). The mixture was then stirred at RT for 2 hours and then cooled to 0° C. The cooled solution was then added to a 0° C. solution of aqueous NaOH (194 ml, 194 mmol) and Et$_2$O (600 mL). The mixture was stirred 30 minutes at RT in a water bath. The organic layer was then separated; the aqueous layer was washed with Et$_2$O (1×); the combined organic layers were dried over MgSO$_4$; and the solvent was removed in vacuo to yield 21.8 g of crude material, which was used directly in the next reaction.

Step 2: 1-t-Butyl 2-methyl (2S,4R)-4-{[6-((1E)-5-{[t-butyl(dimethyl)silyl]oxy}-4,4-dimethylpent-1-en-1-yl)-2-ethoxy-7-methoxyquinolin-4-yl]oxy}pyrrolidine-1,2-dicarboxylate Cs$_2$CO$_3$ (36.7 g, 112 mmol) and Pd(Ph$_3$P)$_4$ (4.33 g, 3.75 mmol) were added to a solution of Intermediate C5 (18.38 g, 67.5 mmol) and the product from Step 1 (19.7 g, 37.5 mmol) in PhMe (281 mL) and water (94 mL), and the mixture was heated to reflux under reflux condenser. After 21 hours, the reaction was diluted with water and EtOAc. The organic layer was dried over MgSO$_4$, and the solvent was removed in vacuo to give crude material which was purified on silica (gradient elution, 0-30% EtOAc/hexane) to yield the title product. LRMS ESI⁺ (M+H)⁺ 673.2; calcd for $C_{36}H_{57}N_2O_8Si$: 673.3.

Step 3: 1-t-Butyl 2-methyl (2S,4R)-4-({2-ethoxy-6-[(1E)-5-hydroxy-4,4-dimethylpent-1-en-1-yl]-7-methoxyquinolin-4-yl}oxy)pyrrolidine-1,2-dicarboxylate

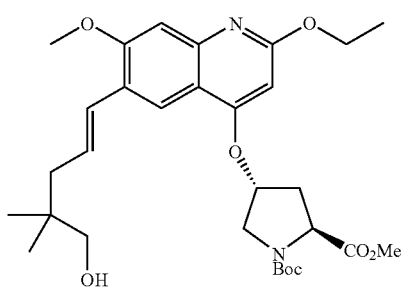

(HF)₃-Et₃N (523 mL, 3210 mmol) was added to a solution of the product from Step 2 (54 g, 80 mmol) in THF (802 mL) at 0° C. The mixture was then warmed to RT. After 15 hours, the solvent was removed in vacuo, and the residue was taken up in EtOAc (500 mL) and water (450 mL). Na₂CO₃ (553 g, 5216 mmol) then was added slowly. The solution then stirred 15 minutes, and the organic layer was then extracted with 10% NaHCO₃ (1×) and brine (1×) and dried over MgSO₄; and the solvent was removed in vacuo. The original aqueous layer was back-extracted with EtOAc and combined with the first extraction. The crude material was then purified on silica (gradient elution, 0-80% EtOAc/hexane) to yield of the title compound. LRMS ESI⁺ (M+H)⁺ 559.3, calcd for $C_{30}H_{43}N_2O_8$: 559.3.

Step 4: 1-t-Butyl 2-methyl (2S,4R)-4-({2-ethoxy-6-[2-(3-hydroxy-2,2-dimethylpropyl)cyclopropyl]-7-methoxyquinolin-4-yl}oxy)pyrrolidine-1,2-dicarboxylate

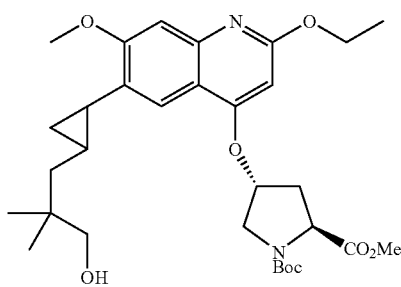

Palladium acetate (0.67 g, 2.97 mol) and freshly prepared diazomethane (300 mL, 0.5 M solution in Et₂O, 150 mmol) were added to a solution of the product from Step 3 (16.6 g, 29.7 mmol) in Et₂O (300 mL) cooled to 0° C. After 15 minutes, N₂ was bubbled through the mixture for 15 minutes, and the black mixture was filtered through CELITE with Et₂O as the eluent. The solvent was removed in vacuo, and the residue was taken up in Et₂O (300 mL) and cooled to 0° C. Palladium acetate (0.67 g, 2.97 mol) and freshly prepared diazomethane (100 mL, 0.5 M solution in Et₂O, 50 mmol) were then added. After 15 minutes, N₂ was bubbled through the mixture for 15 minutes, and the black mixture was filtered through CELITE with Et₂O as the eluent. The solvent was removed in vacuo, and the residue was taken up in Et₂O (300 mL) and cooled to 0° C. Palladium acetate (0.67 g, 2.97 mol) and freshly prepared diazomethane (100 mL, 0.5 M solution in Et₂O, 50 mmol) were then added. After 15 minutes, N₂ was bubbled through the mixture for 15 minutes, and the black mixture was filtered through CELITE with Et₂O as the eluent. The solvent was removed in vacuo, and the crude product was purified on silica (gradient elution, 0-60% EtOAc/hexanes) to yield the title compound. LRMS ESI⁺ (M+H)⁺ 573.2, calcd for $C_{31}H_{45}N_2O_8$: 573.3.

Step 5: Methyl (4R)-4-{[6-(2-{3-[({[(1S)-2-t-butoxy-1-cyclopentyl-2-oxoethyl]amino}carbonyl)oxy]-2,2-dimethylpropyl}cyclopropyl)-2-ethoxy-7-methoxyquinolin-4-yl]oxy}-L-prolinate

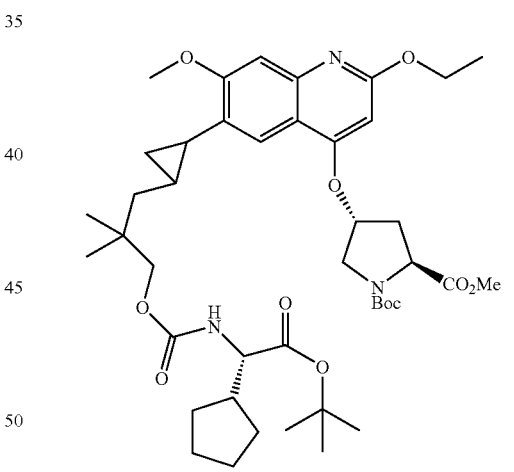

4-Dimethylaminopyridine (4.07 g, 33.4 mmol) and (α5)-α-isocyanato-cyclopentaneacetic acid, 1,1-dimethylethyl ester (10.9 g, 48.4 mmol) were added to a solution of the product from Step 4 (19.1 g, 33.4 mmol) in PhMe (300 mL). After heating at 100° C. for 18 hours, the solvent was removed in vacuo, and the residue was dissolved in EtOAc and washed with aqueous 10% KHSO₄ and brine. The organic layer was dried over Na₂SO₄; the solvent was removed in vacuo, and the resulting oil was purified on silica (gradient elution, 5-40%

EtOAc/hexane) to give the title compound as a colorless solid. LRMS ESI⁺ (M+H)⁺ 798.3, calcd for $C_{43}H_{64}N_3O_{11}$: 798.4.

Step 6: (2S)-Cyclopentyl[({3-[2-(2-ethoxy-7-methoxy-4-{[(3R,5S)-5-(methoxycarbonyl)pyrrolidin-3-yl]oxy}quinolin-6-yl)cyclopropyl]-2,2-dimethylpropoxy}carbonyl)amino]acetic acid dihydrochloride

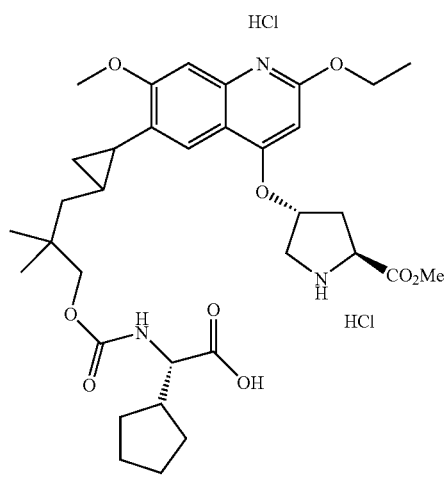

A solution of the product from Step 5 (25.2 g, 31.6 mmol) in 4.0 N HCl in dioxane (400 mL) was stirred for 6 hours. N₂ was bubbled through the solution for 15 minutes, and the solvent was concentrated in vacuo to give 20.3 g of the title compound as a thick oil. LRMS ESI⁺ (M+H−2(HCl))⁺ 642.3, calcd for $C_{34}H_{48}N_3O_9$: 642.3.

Step 7: Methyl (6R,8S,11S,17aR,18aS)-11-cyclopentyl-3-ethoxy-21-methoxy-16,16-dimethyl-10,13-dioxo-7,8,10,11,12,13,15,16,17,17a,18,18a-dodecahydro-6H-1,19-(ethanediylidene)-6,9-methanocyclopropa[o]pyrido[4,3-k][1,10,3,6]dioxadiazacyclononadecine-8-carboxylate

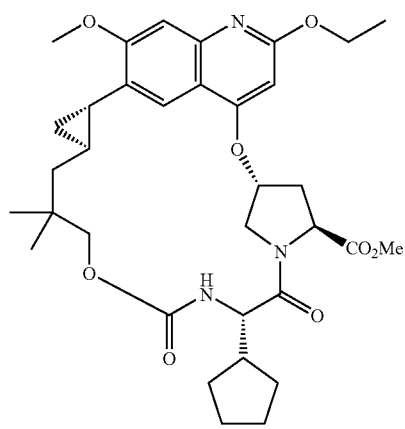

Diisoproylethylamine (18.4 g, 142 mmol) and HATU (16.2 g, 42.6 mmol) were added to a solution of the product of Step 6 (20.3 g, 28.4 mmol) in DCM (4 L). The mixture was stirred 18 hours; the solvent was evaporated in vacuo; and the residue was purified on silica (30% EtOAc/hexane) to give 11.6 g of a 1:1 diastereomeric mixture. This mixture was dissolved in 20% IPA in hexanes and purified in four injections on a 10 cm ID×50 cm L, 20u CHIRALPAK AD column (20% IPA/hexanes). The combined fractions from the first eluting diastereomer were pooled and evaporated in vacuo. The residue was partitioned between EtOAc and aqueous 10% KHSO₄; the organic layer was separated, dried over Na₂SO₄ and evaporated in vacuo to give the title compound as a single diastereomer. LRMS ESI⁺ (M+H)⁺ 624.3, calcd for $C_{34}H_{46}N_3O_8$: 624.3.

Step 8: (6R,8S,11S,17aR,18aS)-11-Cyclopentyl-3-ethoxy-21-methoxy-16,16-dimethyl-10,13-dioxo-7,8,10,11,12,13,15,16,17,17a,18,18a-dodecahydro-6H-1,19-(ethanediylidene)-6,9-methanocyclopropa[o]pyrido[4,3-k][1,10,3,6]dioxadiazacyclononadecine-8-carboxylic acid

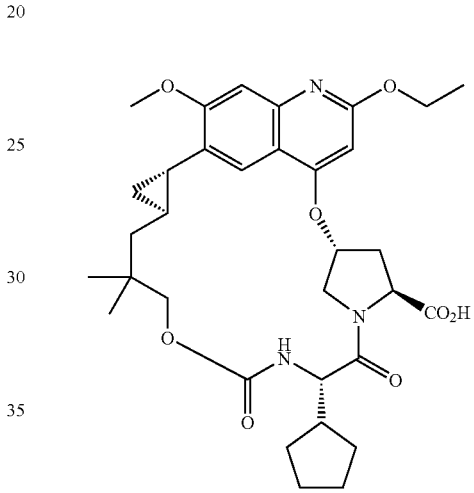

A solution of the product from Step 7 (4.55 g, 7.29 mmol) and LiOH (1.75 g, 72.9 mmol) in THF/water (80 mL each) was heated at 65° C. for 3 hours. The reaction mixture was poured into 10% KHSO₄ and extracted EtOAc (2×). The combined organic layers were washed with brine, dried over Na₂SO₄ and evaporated in vacuo to give the title carboxylic acid. LRMS ESI⁺ (M+H)⁺ 610.3, calcd for $C_{33}H_{44}N_3O_8$: 610.3.

Step 9: (6R,8S,11S,17aR,18aS)-11-Cyclopentyl-N-((1R,2S)-1-{[(cyclopropylsulfonyl)amino]carbonyl}-2-vinylcyclopropyl)-3-ethoxy-21-methoxy-16,16-dimethyl-10,13-dioxo-7,8,10,11,12,13,15,16,17,17a,18,18a-dodecahydro-6H-1,19-etheno-6,9-methanocyclopropa[o]pyrido[4,3-k][1,10,3,6]dioxadiazacyclononadecine-8-carboxamide A solution of the product from Step 8 (0.93 g, 1.54 mmol), Intermediate A1 (0.49 g, 1.85 mmol), HATU (0.76 g, 2.0 mmol) and DIEA (1.075 mL, 6.15 mmol) in DMF (6 mL) was stirred for 2 hours. Water (100 mL) and aqueous 10% KHSO₄ were added to pH~3, and the resulting white solid was filtered off. The solid was then dissolved in EtOAc and washed with aqueous 10% KHSO₄ (2×), and the aqueous layers were back-extracted with EtOAc. The combined organics were washed with brine, dried over Na₂SO₄ and concentrated in vacuo to give a yellow gum. The gum was purified on silica (gradient elution—1 to 8% MeOH in DCM) to give the product as a white powder. $^1$H NMR (500 MHz) (CD$_3$OD) δ 7.62 (d, J=3.5 Hz, 1H), 7.40 (s, 1H), 7.11 (s, 1H), 6.27 (s, 1H), 5.74 (br s, 1H), 5.37 (s, 1H), 5.24 (br d, J=16.5 Hz, 1H), 5.05 (m, 2H), 4.40 (q, J=7 Hz, 2H), 4.34 (d, J=10.5 Hz, 1H), 4.29-4.22 (m, 2H), 4.0 (br, s, 1H), 3.95 (s, 3H), 3.50 (d, J=11 Hz. 1H), 2.95 (br, s, 1H), 2.49 (m, 1H), 2.15 (m, 1H), 1.9-1.6 (m, 7H), 1.40 (t, J=7 Hz, 3H), 1.36-1.22 (m, 6H), 1.0 (br s, 5H), 0.88 (br s, 4H), 0.66 (m, 1H), 0.21 (m, 1H). LRMS ESI$^+$ (M+H)$^+$ 822.2, calcd for C$_{42}$H$_{56}$N$_5$O$_{10}$S: 822.3.

Example 52

(2R,4S,11S,14S,16R)-11-cyclopentyl-N-((1R,2S)-1-{[(cyclopropylsulfonyl)amino]carbonyl}-2-vinylcyclopropyl)-20-ethoxy-24-methoxy-6,6-dimethyl-9,12-dioxo-8,17-dioxa-10,13,21-triazapentacyclo[16.6.2.1$^{13,16}$.0$^{2,4}$.0$^{22,26}$]heptacosa-1(24),18(26),19,21,22,25-hexaene-14-carboxamide

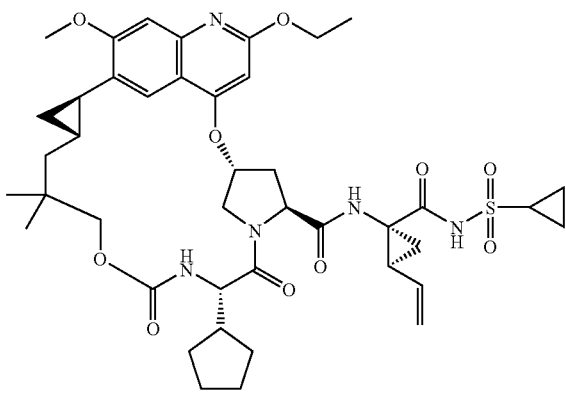

Step 1: Methyl (2R,4S,11S,14S,16R)-11-cyclopentyl-20-ethoxy-24-methoxy-6,6-dimethyl-9,12-dioxo-8,17-dioxa-10,13,21-triazapentacyclo[16.6.2.1$^{13,16}$.0$^{2,4}$.0$^{22,26}$]heptacosa-1(24),18(26),19,21,22,25-hexaene-14-carboxylate

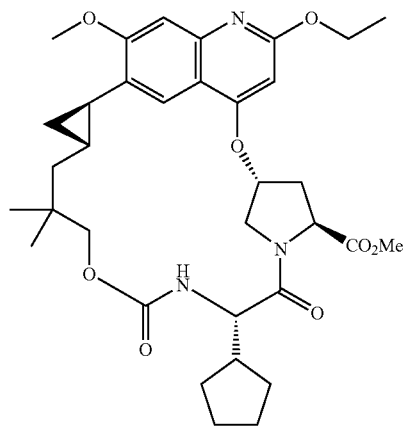

The combined fractions of the second eluting diasteromer from Example 51 Step 7 were pooled and evaporated in vacuo. The residue was partitioned between EtOAc and aqueous 10% KHSO$_4$; the organic layer was separated, dried over Na$_2$SO$_4$ and evaporated in vacuo to give the title compound as a single diastereomer. LRMS ESI$^+$ (M+H)$^+$ 624.3, calcd for C$_{34}$H$_{46}$N$_3$O$_8$: 624.3.

Step 2: (2R,4S,11S,14S,16R)-11-Cyclopentyl-N-((1R,2S)-1-{[(cyclopropylsulfonyl)amino]carbonyl}-2-vinylcyclopropyl)-20-ethoxy-24-methoxy-6,6-dimethyl-9,12-dioxo-8,17-dioxa-10,13,21-triazapentacyclo[16.6.2.1$^{13,16}$.0$^{2,4}$.0$^{22,26}$]heptacosa-1(24),18(26),19,21,22,25-hexaene-14-carboxamide The title compound was prepared according to Steps 8 and 9 from Example 51. $^1$H NMR (500 MHz) (CD$_3$OD) δ 7.63 9d, J=8.5 Hz, 1H), 7.40 (s, 1H), 7.11 (s, 1H), 6.27 (s, 1H), 5.74 (br s, 1H), 5.37 (s, 1H), 5.23 (br d, J=16.5 Hz, 1H), 5.05 (m, 2H), 4.40 (q, =7.0 Hz, 2H), 4.34 (d, J=10.5 Hz, 1H), 4.28 (m, 1H), 4.23 (m, 1H), 4.0 (m, 1H), 3.95 (s, 3H), 3.50 (d, J=11.0 Hz, 1H), 2.95 (br s, 1H), 2.49 (m, 2H), 2.15 (m, 4H), 1.90-1.62 (m, 7H), 1.40 (t, J=7.0 Hz, 3H), 1.38-1.22 (m, 6H), 1.06 (m, 2H), 1.05 (s, 3H), 0.91 (s, 3H), 0.87 9m, 2H), 0.67 (m, 1H), 0.21 (m, 1H). LRMS ESI$^+$ (M+H)$^+$ 822.2, calcd for C$_{42}$H$_{56}$N$_5$O$_{10}$S: 822.3.

Example 53

(2R,4S,7S)-7-cyclohexyl-N-((1R,2S)-1-{[(cyclopropylsulfonyl)amino]carbonyl}-2-vinylcyclopropyl)-20-(dimethylamino)-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclononadecine-4-carboxamide

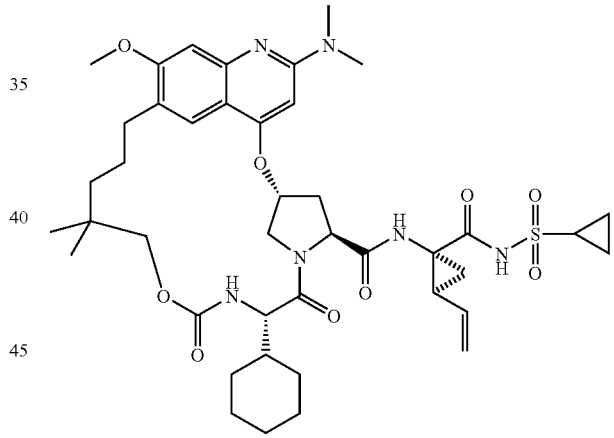

Dimethylamine (0.269 mL, 2M in MeOH, 0.539 mmol) was added to a solution of Intermediate C2 (50 mg, 0.054 mmol) in DMSO (1 mL). The mixture was then heated to 100° C. for 2 hours, cooled to RT and purified directly by reverse-phase chromatography (gradient elution, 30-95% MeCN/0.15% TFA in water) to give the title compound as a white solid (17 mg). $^1$H NMR (500 MHz, CD$_3$OD): δ 9.33 (s, 1H), 7.61 (s, 1H), 7.34 (s, 1H), 6.49 (s, 1H), 5.75 (m, 2H), 5.30 (d, J=17.0 Hz, 1H), 5.13 (d, J=10.0 Hz, 1H), 4.62 (d, J=11.5, 1H), 4.44 (m, 1H), 4.33 (d, J=11.0 Hz, 1H), 4.27 (d, J=10.0 Hz, 1H), 4.07 (m, 1H), 3.99 (s, 3H), 3.41 (s, 6H), 3.28 (d, J=11.0 Hz, 1H), 3.13 (m, 1H), 2.97 (m, 1H), 2.59 (m, 1H), 2.32 (m, 1H), 2.19 (m, 2H), 1.91 (m, 3H), 1.78-1.21 (m, 15H), 1.12 (m, 2H), 1.07 (s, 3H), 1.01 (m, 1H), 0.78 (s, 3H). LRMS ESI$^+$ (M+H)$^+$ 823.7.

The following compounds were prepared according to Example 10 using the appropriate amine in place of dimethylamine.

| Ex. | Structure | Name | Amine | LRMS (M + H)+ |
|---|---|---|---|---|
| 54 | 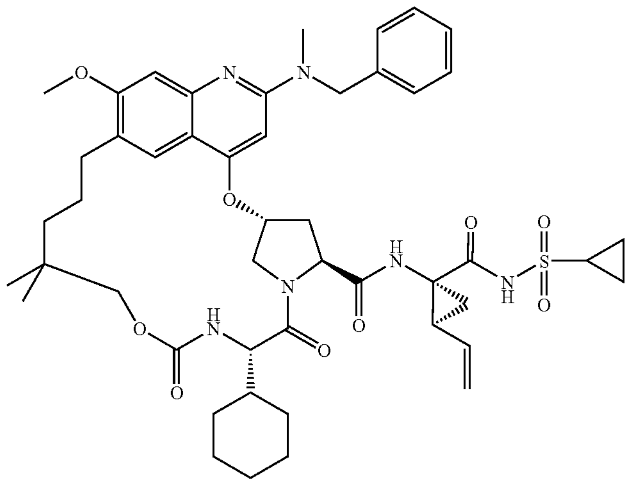 | (2R,4S,7S)-20-[benzyl(methyl) amino]-7-cyclohexyl-N-((1R,2S)-1-{[(cyclopropylsulfonyl)amino] carbonyl}-2-vinylcyclopropyl)-23-methoxy-12,12-dimethyl-6,9-dioxo-3,4,6,7,8,9,12,13,14,15-decahydro-2H,11H-16,18-(ethanediylidene)-2,5-methanopyrido [4,3-k][1,10,3,6]dioxadiaza cyclononadecine-4-carboxamide | N-Methyl benzylamine | 899.5 |
| 55 | 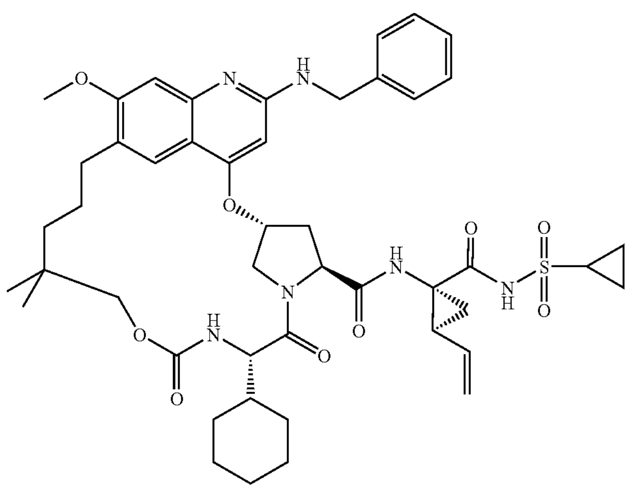 | (2R,4S,7S)-20-(benzylamino)-7-cyclohexyl-N-((1R,2S)-1-{[(cyclopropylsulfonyl)amino] carbonyl}-2-vinylcyclopropyl)-23-methoxy-12,12-dimethyl-6,9-dioxo-3,4,6,7,8,9,12,13,14,15-decahydro-2H,11H-16,18-(ethanediylidene)-2,5-methanopyrido [4,3-k][1,10,3,6]dioxadiazal cyclononadecine-4-carboxamide | Benzylamine | 885.6 |
| 56 | 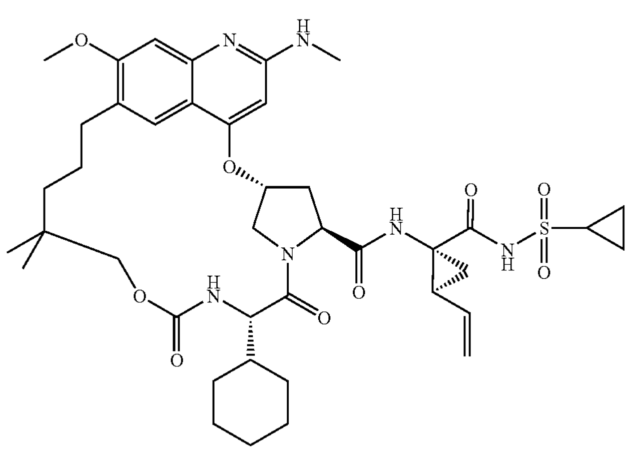 | (2R,4S,7S)-7-cyclohexyl-N-((1R, 2S)-1-{[(cyclopropylsulfonyl)amino] carbonyl}-2-vinylcyclopropyl)-23-methoxy-12,12-dimethyl-20-(methylamino)-6,9-dioxo-3,4,6,7, 8,9,12,13,14,15-decahydro-2H,11H-16,18-(ethanediylidene)-2,5-methanopyrido[4,3-k][1,10,3,6] dioxadiazal cyclononadecine-4-carboxamide | Methylamine | 809.7 |

-continued

| Ex. | Structure | Name | Amine | LRMS (M + H)+ |
|---|---|---|---|---|
| 57 | 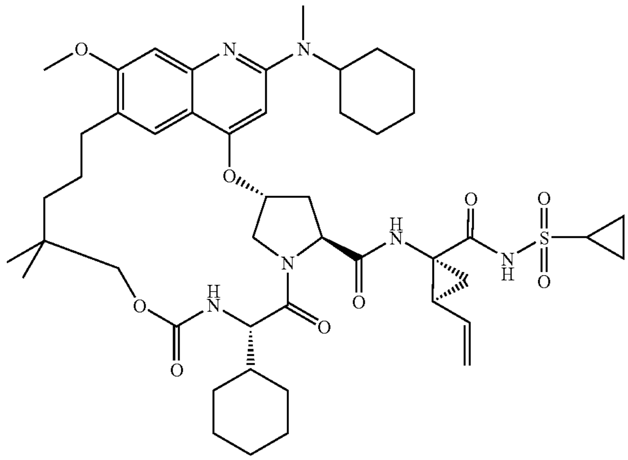 | (2R,4S,7S)-7-cyclohexyl-20-[cyclohexyl(methyl)amino]-N-((1R,2S)-1-{[(cyclopropylsulfonyl)amino]carbonyl}-2-vinylcyclopropyl)-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazacyclo nonadecine-4-carboxamide | N-Methylcyclo hexanamine | 891.3 |
| 58 | 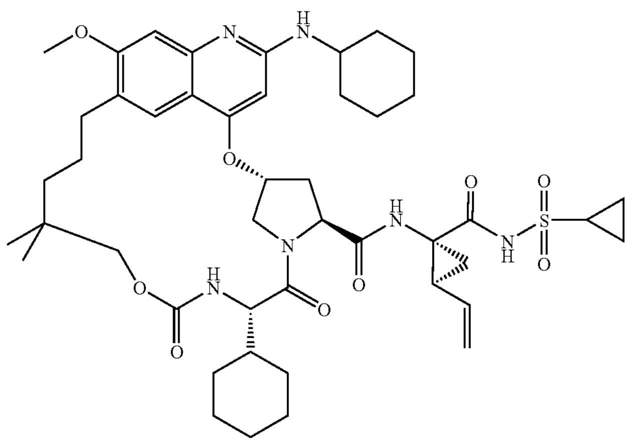 | (2R,4S,7S)-7-cyclohexyl-20-(cyclohexylamino)-N-((1R,2S)-1-{[(cyclopropylsulfonyl)amino]carbonyl}-2-vinylcyclopropyl)-23-methoxy-12,12-dimethyl-6,9-dioxo-3,4,6,7,8,9,12,13,14,15-decahydro-2H,11H-16,18-(ethanediylidene)-2,5-methanopyrido[4,3-k][1,10,3,6]dioxadiazal cyclononadecine-4-carboxamide | Cyclo-hexylamine | 877.2 |
| 59 | 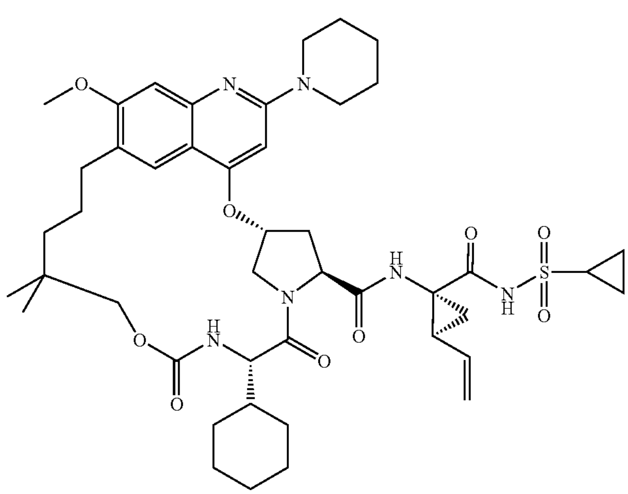 | (2R,4S,7S)-7-cyclohexyl-N-((1R,2S)-1-{[(cyclopropylsulfonyl)amino]carbonyl}-2-vinylcyclopropyl)-23-methoxy-12,12-dimethyl-6,9-dioxo-20-piperidin-1-yl-3,4,6,7,8,9,12,13,14,15-decahydro-2H,11H-16,18-(ethanediylidene)-2,5-methanopyrido[4,3-k][1,10,3,6]dioxadiaza cyclononadecine-4-carboxamide | Piperidine | 863.7 |

| Ex. | Structure | Name | Amine | LRMS (M + H)+ |
|---|---|---|---|---|
| 60 | 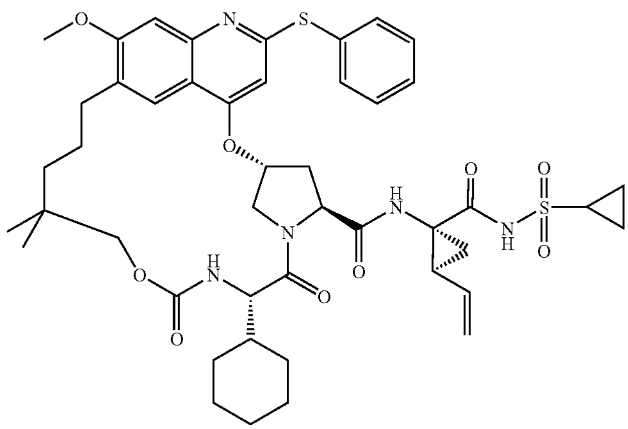 | (3R,5S,8S)-8-cyclohexyl-N-((1R, 2S)-1-{[(cyclopropylsulfonyl) amino]carbonyl}-2-vinylcyclopropyl)-18-methoxy-13, 13-dimethyl-7,10-dioxo-22-(phenyl-thio)-2,11-dioxa-6,9,21-triazatetracyclo [15.6.2.1$^{3,6}$•O$^{20,24}$]hexacosa-1(23), 17,19,21,24-pentaene-5-carboxamide | thiophenol | 888.5 |
| 61 | 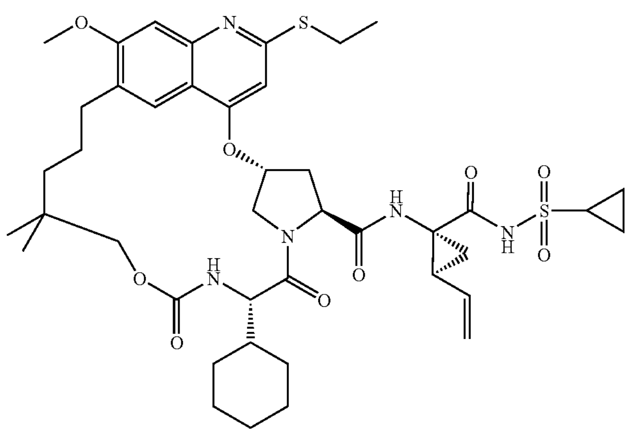 | (3R,5S,8S)-8-cyclohexyl-N-((1R, 2S)-1-{[(cyclopropylsulfonyl) amino]carbonyl}-2-vinyl-cyclopropyl)-22-(ethylthio)-18-methoxy-13,13-dimethyl-7,10-dioxo-2,11-dioxa-6,9,21-triazatetracyclo [15.6.2.1$^{3,6}$•O$^{20,24}$]hexacosa-1(23), 17,19,21,24-pentaene-5-carboxamide | ethanethiol | 840.3 |
| 62 | 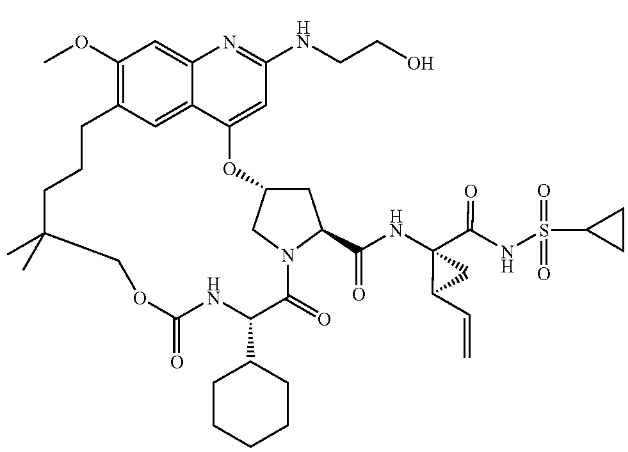 | (3R,5S,8S)-8-cyclohexyl-N-((1R, 2S)-1-{[(cyclopropylsulfonyl)amino] carbonyl}-2-vinylcyclopropyl)-22-[(2-hydroxyethyl)amino]-18-methoxy-13,13-dimethyl-7,10-dioxo-2,11-dioxa-6,9,21-triazatetracyclo[15.6.2.1$^{3,6}$•O$^{20,24}$] hexacosa-1(23),17,19,21,24-pentaene-5-carboxamide | 2-aminoethanol | 839.5 |

Example 63

(3R,5S,8S)-22-[acetyl(methyl)amino]-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide

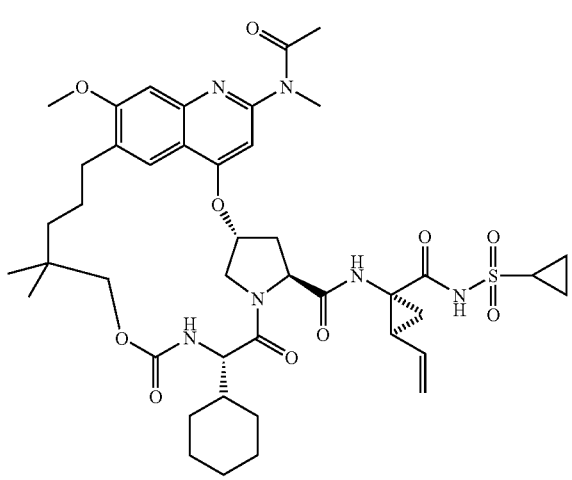

Step 1: Methyl (3R,5S,8S)-8-cyclohexyl-18-methoxy-13,13-dimethyl-22-(methylamino)-7,10-dioxo-2,11-dioxa-6,9,21-triazatetracyclo[15.6.2.1$^{3,6}$.0$^{20,24}$]hexacosa-1(23),17,19,21,24-pentaene-5-carboxylate

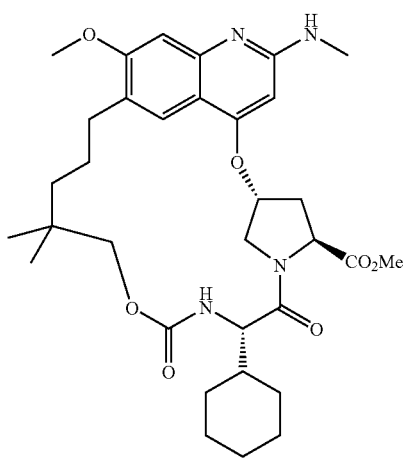

Methylamine (0.685 mL, 10 M, 1.37 mmol) was added to a solution of Intermediate C4 (100 mg, 0.137 mmol) in DMSO (1 mL), and the mixture was heated to 100° C. for 15 hours. The residue was cooled to RT and directly purified by preparative HPLC Reverse phase (C-18) PHENOMENEX LUNA, 100×30 mm column, 5 to 95% MeCN in 0.15% aqueous TFA, eluting with acetonitrile/water+0.1% TFA, to give the title compound after working up with EtOAc and saturated sodium bicarbonate. LRMS ESI$^+$ (M+H)$^+$ 611.4; calcd for $C_{33}H_{47}N_4O_7$: 611.4.

Step 2: Methyl (3R,5S,8S)-22-[acetyl(methyl)amino]-8-cyclohexyl-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxylate

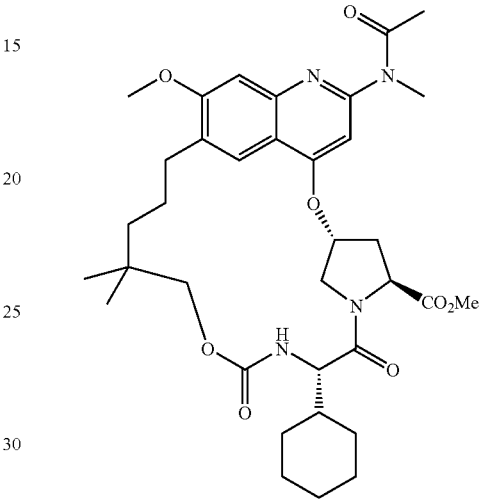

Et$_3$N (0.005 mL, 0.041 mmol) and acetic anhydride (0.012 mL, 0.123 mmol) were added to a solution of the product from Step 1 (25 mg, 0.041 mmol) in DCM (1 mL). After 2 hours, the solvent was removed in vacuo, and the residue was taken up in EtOAc and extracted with 10% KHSO$_4$. The organic layer was dried over MgSO$_4$, and the solvent was removed in vacuo to yield the title compound. LRMS ESI$^+$ (M+H)$^+$ 653.4; calcd for $C_{35}H_{49}N_4O_8$: 653.4.

Step 3: (3R,5S,8S)-22-[acetyl(methyl)amino]-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide The title compound was prepared according to Steps 2 and 3 of Example 1. $^1$H NMR (400 MHz, CDCl$_3$) δ 12.17 (s, 1H), 8.70 (m, 1H), 7.62 (m, 1H), 7.52 (s, 1H), 7.43 (s, 1H), 7.16 (m, 2H), 6.84 (m, 1H), 6.45 (s, 1H), 6.36 (s, 1H), 5.89 (m, 1H), 5.79 (m, 2H), 5.46 (m, 2H), 5.29-5.08 (m, 5H), 4.99 (m, 2H), 4.62 (m, 1H), 4.39 (m, 2H), 4.10 (m, 1H), 3.91-3.82 (m, 2H), 3.73 (s, 3H), 3.49-3.37 (m, 2H), 3.14 (m, 1H), 3.05 (m, 1H), 2.71-2.41 (m, 2H), 2.21-2.10 (m, 3H), 1.90-1.69 (m, 3H), 3.13 (s, 6H), 1.20 (m, 2H), 1.10-1.02 (m, 4H), 0.95-0.79 (m, 3H) ppm. LRMS ESI$^+$ (M+H)$^+$ 851.5; calcd for $C_{43}H_{59}N_6O_{10}S$: 851.4.

The following compounds were prepared according to the procedures of Example 63, using the appropriate amine and acylating reagent in place of methylamine and acetic anhydride.

| Ex. | Structure | Name | Amine/Acylating reagent | LRMS |
|---|---|---|---|---|
| 64 | 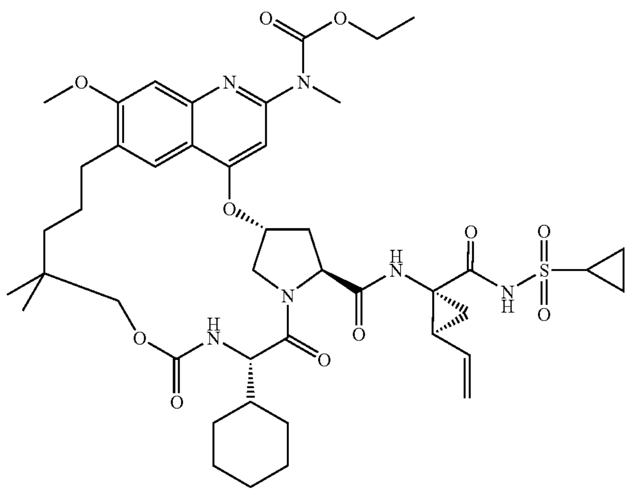 | ethyl[(3R,5S,8S)-8-cyclohexyl-5-{[((1R,2S)-1-{[(cyclopropyl-sulfonyl)amino]carbonyl}-2-vinylcyclopropyl)amino]carbonyl}-18-methoxy-13,13-dimethyl-7,10-dioxo-2,11-dioxa-6,9,21-triazatetracyclo[15.6.2.1$^{3,6}$•0$^{20,24}$]hexacosa-1(23),17,19,21,24-pentaen-22-yl]methylcarbamate | Methylamine/ ethylchloroformate | 881.5 |
| 65 | 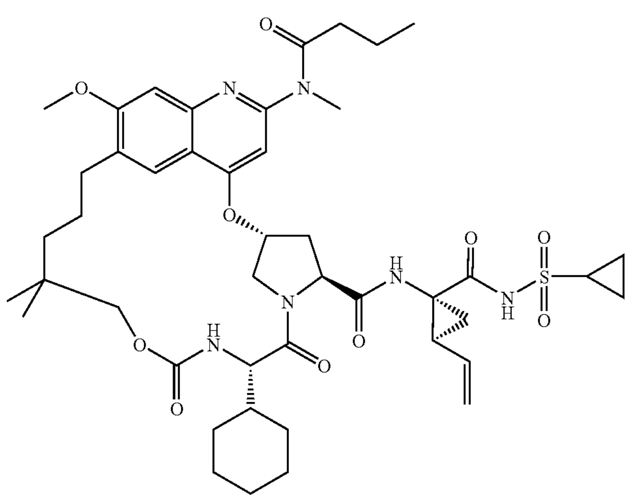 | (3R,5S,8S)-22-[butyryl(methyl)amino]-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,21-triazatetracyclo[15.6.2.1$^{3,6}$•0$^{20,24}$]hexacosa-1(23),17,19,21,24-pentaene-5-carboxamide | Methylamine/ butanoyl chloride | 879.5 |

| Ex. | Structure | Name | Amine/Acylating reagent | LRMS |
|---|---|---|---|---|
| 66 | 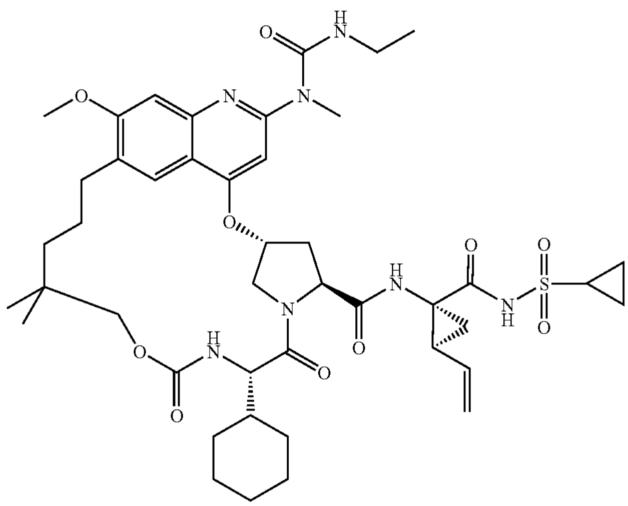 | (3R,5S,8S)-8-cyclohexyl-N-((1R,2S)-1-{[(cyclopropyl-sulfonyl)amino]carbonyl}-2-vinylcyclopropyl)-22-[[(ethyl-amino)carbonyl](methyl)amino]-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide | Methylamine/ ethylisocyanate | 880.3 |
| 67 | 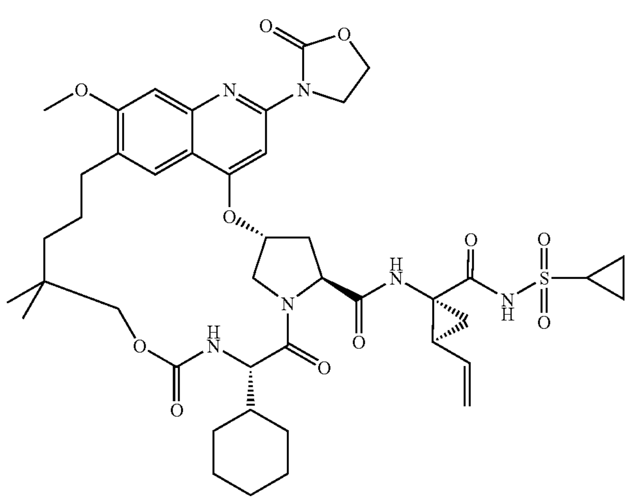 | (3R,5S,8S)-8-cyclohexyl-N-((1R,2S)-1-{[(cyclopropyl-sulfonyl)amino]carbonyl}-2-vinylcyclopropyl)-18-methoxy-13,13-dimethyl-7,10-dioxo-22-(2-oxo-1,3-oxazolidin-3-yl)-2,11-dioxa-6,9,21-triazatetracyclo[15.6.2.1$^{3,6}$.0$^{20,24}$]hexacosa-1(23),17,19,21,24-pentaene-5-carboxamide | 1-aminoethanol/ CDI | 865.4 |

Example 68

(3R,5S,8S)-8-cyclohexyl-N-((1R,2S)-1-{[(cyclopropylsulfonyl)amino]carbonyl}-2-vinylcyclopropyl)-18-methoxy-13,13-dimethyl-7,10-dioxo-22-(2-phenylethyl)-2,11-dioxa-6,9,21-triazatetracyclo[15.6.2.1$^{3,6}$.0$^{20,24}$]hexacosa-1(23),17,19,21,24-pentaene-5-carboxamide

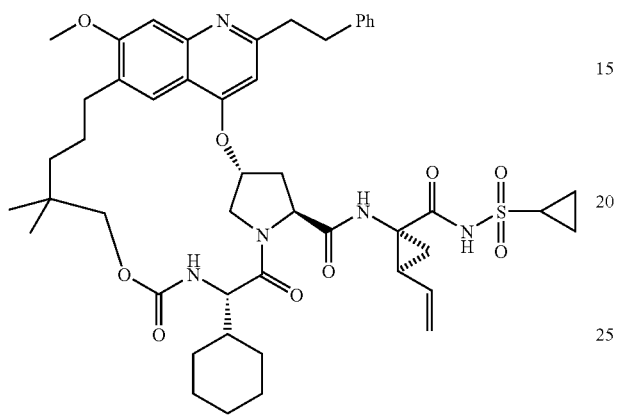

Step 1: (3R,5S,8S)-8-Cyclohexyl-18-methoxy-13,13-dimethyl-7,10-dioxo-22-(2-phenylethyl)-2,11-dioxa-6,9,21-triazatetracyclo[15.6.2.1$^{3,6}$.0$^{20,24}$]hexacosa-1(23),17,19,21,24-pentaene-5-carboxylic acid

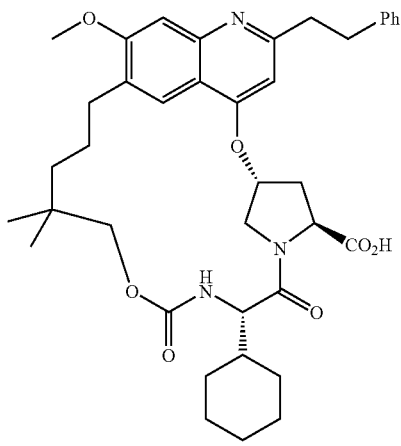

[(E)-2-phenylvinyl]boronic acid (22 mg, 0.144 mmol) and Pd(Ph$_3$P)$_4$ (5.5 mg, 0.005 mmol) were added to a solution of Intermediate C4 (35 mg, 0.048 mmol) and sodium carbonate (25 mg, 0.24 mmol) in THF (1 mL) and water (0.5 mL). The mixture was then heated to 70° C. for 1 hour and then extracted with 1N HCl and Et$_2$O. The organic layer was dried over MgSO$_4$; the solvent was removed in vacuo; and the residue was directly taken up in THF (5 mL). 10% Pd/C (10 mg) was added to this solution, and the solution was placed under H$_2$ for 3 hours. The mixture was then filtered through a pad of glass wool, and the solvent was removed in vacuo to yield the title compound. LRMS ESI$^+$ (M+H)$^+$ 672.4, calcd for C$_{39}$H$_{50}$N$_3$O$_7$: 672.4.

Step 2: (3R,5S,8S)-8-Cyclohexyl-N-((1R,2S)-1-{[(cyclopropylsulfonyl)amino]carbonyl}-2-vinylcyclopropyl)-18-methoxy-13,13-dimethyl-7,10-dioxo-22-(2-phenylethyl)-2,11-dioxa-6,9,21-triazatetracyclo[15.6.2.1$^{3,6}$.0$^{20,24}$]hexacosa-1(23),17,19,21,24-pentaene-5-carboxamide The title compound was prepared according to Step 3, Example 1. LRMS ESI$^+$ (M+H)$^+$ 884.5, calcd for C$_{48}$H$_{62}$N$_5$O$_9$S: 884.4.

Example 69

(3R,5S,8S)-22-allyl-8-cyclohexyl-N-((1R,2S)-1-{[(cyclopropylsulfonyl)amino]carbonyl}-2-vinylcyclopropyl)-18-methoxy-13,13-dimethyl-7,10-dioxo-2,11-dioxa-6,9,21-triazatetracyclo[15.6.2.1$^{3,6}$.0$^{20,24}$]hexacosa-1(23),17,19,21,24-pentaene-5-carboxamide

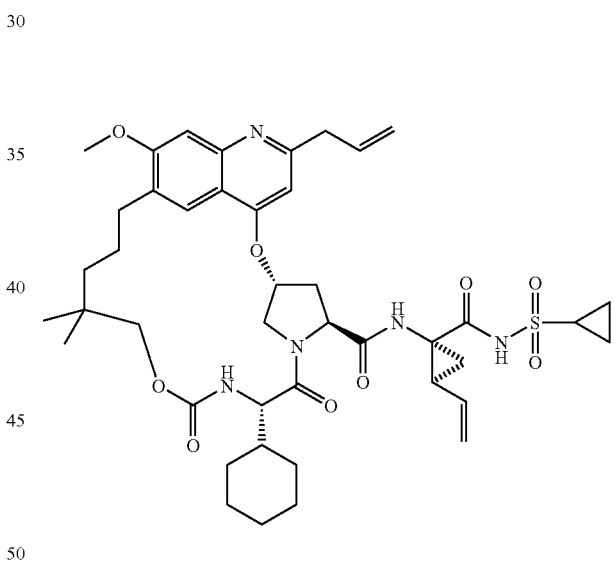

Pd(Ph$_3$P)$_4$ (6.23 mg, 5.39 µmol) was added to a mixture of Intermediate C2 (50 mg, 0.054 mmol), 2-allyl-4,4,5,5-tetramethyl-1,3,2-dioxaborolane (27 mg, 0.162 mmol), and Na$_2$CO$_3$ (28.6 mg, 0.269 mmol) in THF (1 mL) and water (0.5 mL). The mixture was then heated to 70° C. for 1 hour. The mixture was then diluted with EtOAc and extracted with water and then brine. The organic layer was dried over MgSO$_4$, and the solvent was removed in vacuo. The residue was purified by preparative HPLC reverse-phase (C-18), 150×20 mm column, 30 to 95% MeCN in 0.15% aqueous TFA, eluting with acetonitrile/water+0.1% TFA, to give the title compound. LRMS ESI$^+$ (M+H)$^+$ 820.7, calcd for C$_{43}$H$_{58}$N$_5$O$_9$S: 820.5

What is claimed is:
1. A compound of formula (I):

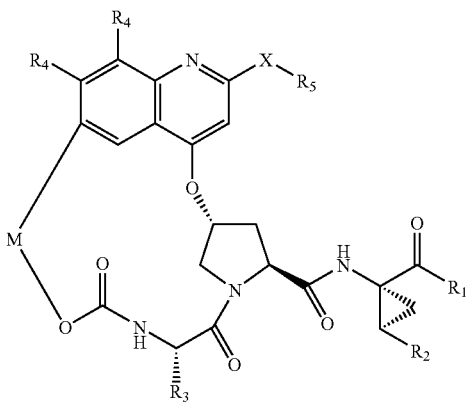

or a pharmaceutically acceptable salt thereof, wherein:
$R_1$ is OH, $NHSO_2R_6$, $NHSO_2NR_8R_9$, or $NHP(O)R_{11}R_{12}$;
$R_2$ is $C_1$-$C_4$ alkyl or $C_2$-$C_4$ alkenyl, wherein said alkyl or alkenyl is substituted with 0 to 3 halo;
$R_3$ is $C_1$-$C_8$ alkyl, $C_3$-$C_8$ cycloalkyl($C_1$-$C_8$)alkyl, aryl($C_1$-$C_8$)alkyl, Het, or $C_3$-$C_8$ cycloalkyl, wherein aryl is phenyl or naphthyl, and each alkyl, cycloalkyl, or aryl is substituted with 0 to 3 substituents selected from the group consisting of halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;
Het is a 5- to 6-membered saturated cyclic ring having 1 or 2 heteroatoms selected from N, O and S, wherein said ring is substituted with 0 to 3 substituents selected from halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;
each $R_4$ is independently H, $C_1$-$C_6$ alkyl, halogen or $OR_{10}$;
$R_5$ is $C_1$-$C_8$ alkyl, aryl, heteroaryl, heterocyclyl, $C_3$-$C_8$ cycloalkyl, $C_1$-$C_6$ haloalkyl or $C_1$-$C_6$ thioalkyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl or alkyl is substituted with 0 to 4 substituents selected from the group consisting of halo, $OR_{10}$, $SR_{10}$, $N(R_7)_2$, $C_1$-$C_6$ alkyl, aryl, heteroaryl, heterocyclyl, $C_1$-$C_6$ haloalkyl, $C_3$-$C_6$ cycloalkyl, cycloalkoxy, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$, and wherein said heteroaryl or heterocyclyl substituent is unsubstituted or substituted with $C_1$-$C_6$ alkyl or aryl;
each $R_6$ is independently $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is substituted with 0 to 2 W substituents or $P(O)R_{11}R_{12}$, and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;
W is H, halo, $OR_{10}$, $C_1$-$C_6$ alkyl, CN, $CF_3$, $SR_{10}$, $SO_2(C_1$-$C_6$ alkyl), $C_3$-$C_8$ cycloalkyl, $C_3$-$C_8$ cycloalkoxy, $C_1$-$C_6$ haloalkyl, or $N(R_7)_2$;
each $R_7$ is independently H, $C_1$-$C_6$ alkyl or $C_3$-$C_6$ cycloalkyl;
X is O, NH, $N(CH_3)$, $N(C(O)CH_3)$, $N(C(O)OCH_2CH_3)$, $CH_2$ or S;
or X—$R_5$ is a heterocyclyl ring wherein the point of attachment is the heteroatom;
M is $C_1$-$C_8$ alkylene, $C_2$-$C_8$ alkenylene or ($C_1$-$C_8$ alkylene)-O—($C_1$-$C_8$ alkylene), wherein said $C_1$-$C_8$ alkylene, $C_2$-$C_8$ alkenylene or ($C_1$-$C_8$ alkylene)-O—($C_1$-$C_8$ alkylene) is substituted with 0 to 4 substituents selected from the group consisting of $C_1$-$C_8$ alkyl, $C_3$-$C_8$ cycloalkyl($C_1$-$C_8$ alkyl), aryl($C_1$-$C_8$ alkyl), and $N(R_4)_2$; where 2 adjacent substituents of M are optionally taken together to form a 3- to 6-membered cyclic ring;
$R_8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, aryl, heteroaryl or heterocyclyl is substituted with 0 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR_{10}$, $SR_{10}$, $N(R_{10})_2$, $N(C_1$-$C_6$ alkyl)O($C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$;
wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;
$R_9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, alkoxy, cycloalkoxy, aryl, heteroaryl or heterocyclyl is substituted with 0 to 4 substituents selected from the group consisting of aryl, $C_3$-$C_8$ cycloalkyl, heteroaryl, heterocyclyl, $C_1$-$C_6$ alkyl, halo($C_1$-$C_6$ alkoxy), halo, $OR_{10}$, $SR_{10}$, $N(R_{10})_2$, $N(C_1$-$C_6$ alkyl)O($C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$;
wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R_8$ and $R_9$ are optionally taken together, with the nitrogen atom to which they are attached, to form a 4- to 8-membered monocyclic ring containing 0 to 2 additional heteroatoms selected from N, O and S;

each $R_{10}$ is independently H or $C_1$-$C_6$ alkyl;

each $R_{11}$ is independently $OR_{13}$, $N(R_{10})$—V—$CO_2R_{10}$, O—V—$CO_2R_{10}$, S—V—$CO_2R_{10}$, $N(R_{10})(R_{13})$, $R_{14}$, or $N(R_{10})SO_2R_6$;

each $R_{12}$ is independently $OR_{13}$, $N(R_{10})$—V—$CO_2R_{10}$, O—V—$CO_2R_{10}$, S—V—$CO_2R_{10}$, or $N(R_{10})(R_{13})$;

or $R_{11}$ and $R_{12}$ are optionally taken together, with the phosphorus atom to which they are attached, to form a 5- to 7-membered monocyclic ring;

each V is independently $CH(R_{15})$ or $C_1$-$C_4$ alkylene-CH$(R_{15})$;

each $R_{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is substituted with 0 to 2 substituents selected from the group consisting of aryl, aryl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R_{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is substituted with 0 to 2 substituents selected from the group consisting of $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; and each $R_{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is substituted with 0 to 2 substituents selected from the group consisting of $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

2. A compound of claim 1, wherein $R_1$ is $NHSO_2R_6$.

3. A compound of claim 2, wherein $R_6$ is $C_3$-$C_6$ cycloalkyl.

4. A compound of claim 3, wherein $R_6$ is cyclopropyl.

5. A compound of claim 1, wherein $R_2$ is $C_2$-$C_4$ alkenyl.

6. A compound of claim 5, wherein $R_2$ is —CH=$CH_2$.

7. A compound of claim 1, wherein $R_3$ is $C_3$-$C_8$ cycloalkyl.

8. A compound of claim 7, wherein $R_3$ is cyclohexyl or cyclopropyl.

9. A compound of claim 1, wherein each $R_4$ is independently H, chloro, iodo or —O—$C_1$-$C_6$ alkyl.

10. A compound of claim 9, wherein each $R_4$ is independently H, chloro, iodo or —$OCH_3$.

11. A compound of claim 1, wherein X is O, NH or $N(CH_3)$.

12. A compound of claim 1, wherein M is $C_1$-$C_8$ alkylene or $C_2$-$C_8$ alkenylene, having 0 to 4 substituents selected from the group consisting of $C_1$-$C_8$ alkyl, $C_3$-$C_8$ cycloalkyl($C_1$-$C_8$ alkyl), aryl($C_1$-$C_8$ alkyl), and $N(R_4)_2$, where 2 adjacent substituents of M are optionally taken together to form a 3- to 6-membered cyclic ring.

13. A compound of claim 12, wherein M is $C_5$-$C_8$ alkylene, having 0 to 4 substituents selected from the group consisting of $C_1$-$C_8$ alkyl, $C_3$-$C_8$ cycloalkyl($C_1$-$C_8$ alkyl), aryl($C_1$-$C_8$ alkyl), and $N(R_4)_2$, where 2 adjacent substituents of M are optionally taken together to form a 3- to 6-membered cyclic ring.

14. The compound of claim 12, wherein M is selected from the group consisting of —$(CH_2)_3C(CH_3)_2CH_2$—, —CH=$CH(CH_2)_5$—, —$(CH_2)_7$—, —$CH_2CH$=CH$(CH_2)_4$—, —$(CH_2)_6$—, —CH=$CH(CH_2)_4$—, —CH=CH$(CH_2)_3C(CH_3)_2CH_2$—, —CH=$CH(CH_2)_3$—, —$(CH_2)_5$—, —CH=$CH(CH_2)_3$—, —$(CH_2)_4$—, —$(CH_2)_3$—, —CH=$CH(CH_2)_2C(CH_3)_2CH_2$—, —$(CH_2)_4C(CH_3)_2CH_2$—, —C(=$CH_2$)$(CH_2)_5$—, —C(=$CH_2$)$(CH_2)_3$—, —$CH_2CH$=CH$(CH_2)_3$—.

15. The compound of claim 1, wherein M is selected from the group consisting of

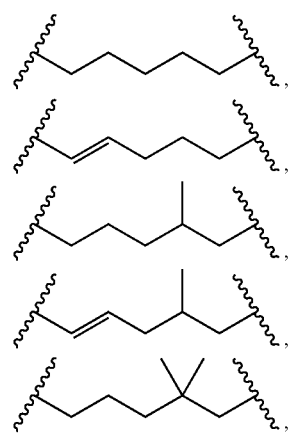

123
-continued
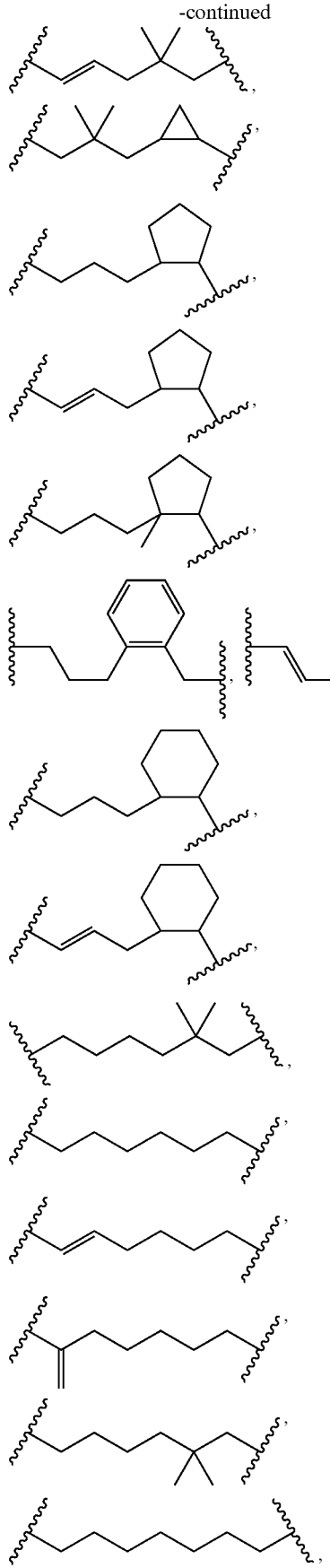
124
-continued
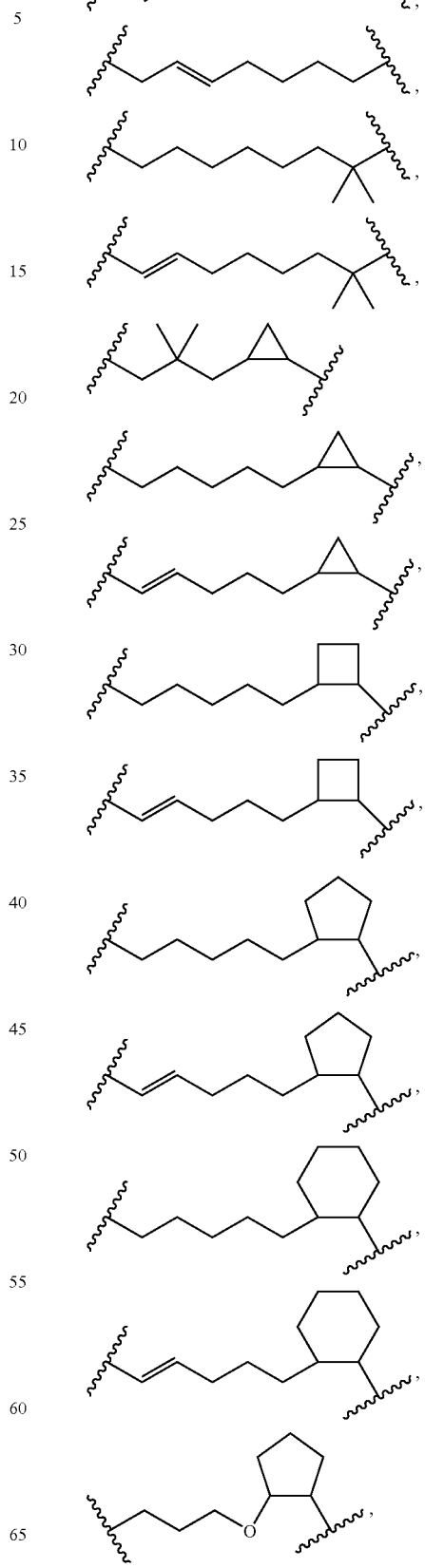

-continued

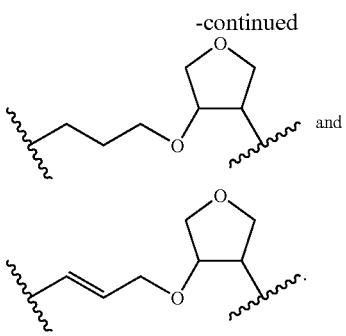

16. A compound of claim 1, wherein $R_5$ is $C_1$-$C_8$ alkyl or $C_3$-$C_8$ cycloalkyl, wherein said alkyl or cycloalkyl is substituted with 0 to 4 substituents selected from the group consisting of aryl, heterocyclyl, or $CF_3$, and wherein said heterocyclyl substituent is unsubstituted or substituted with $CH_3$.

17. A compound of claim 16, wherein $R_5$ is $C_1$-$C_5$ alkyl or $C_5$-$C_6$ cycloalkyl, wherein said alkyl or cycloalkyl is substituted with 0 or 1 substituent selected from the group consisting of phenyl, thiolyl, or $CF_3$, and wherein said thiolyl substituent is unsubstituted or substituted with $CH_3$.

18. A compound of claim 1, wherein X—$R_5$ is a piperidine ring, wherein the point of attachment is a nitrogen atom.

19. A compound of claim 1, wherein:

$R_1$ is $NHSO_2R_6$;

$R_6$ is cyclopropyl;

$R_2$ is —CH=$CH_2$;

$R_3$ is selected from the group consisting of t-butyl, cyclohexyl and cyclopropyl;

each $R_4$ is independently H, chloro, iodo or —$OCH_3$;

X is O, NH, N($CH_3$), N(C(O)$CH_3$), N(C(O)O$CH_2CH_3$), $CH_2$ or S;

$R_5$ is $CH_3$, $CH_2CH_3$, phenyl, cyclopentyl or cyclohexyl, wherein said $CH_3$ or said $CH_2CH_3$ is substituted with 0 to 4 substituents selected from the group consisting of halo, OH, phenyl, heteroaryl or heterocyclyl, and said heteroaryl or heterocyclyl substituent is unsubstituted or substituted with $CH_3$, $CH_2CH_3$ or phenyl;

or X—$R_5$ is a piperidine ring, wherein the point of attachment is a nitrogen atom; and M is

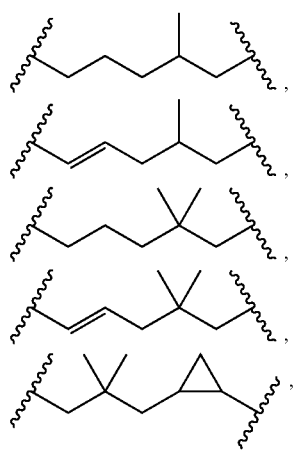

-continued

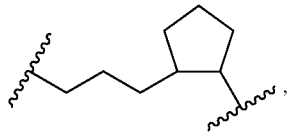

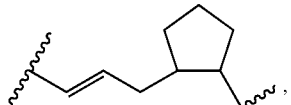

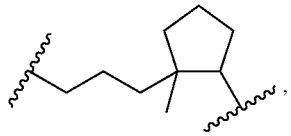

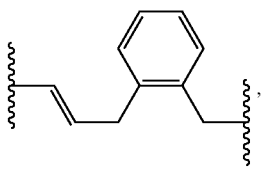

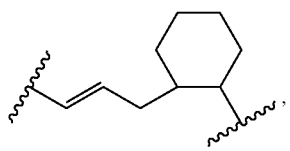

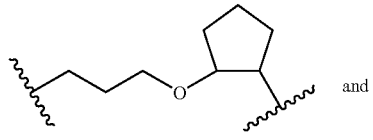 and

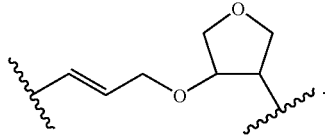

20. A compound of claim 1, or a pharmaceutically acceptable salt thereof, selected from the group consisting of:

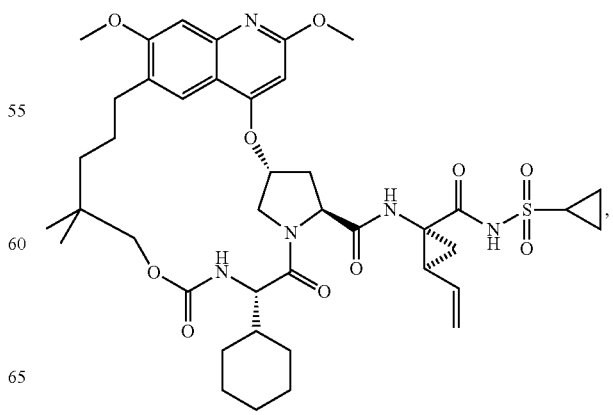

127
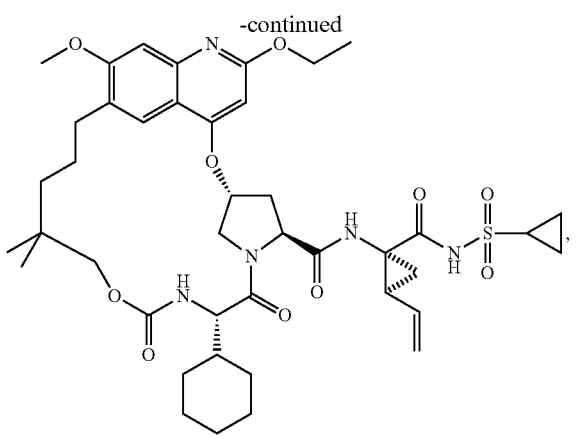
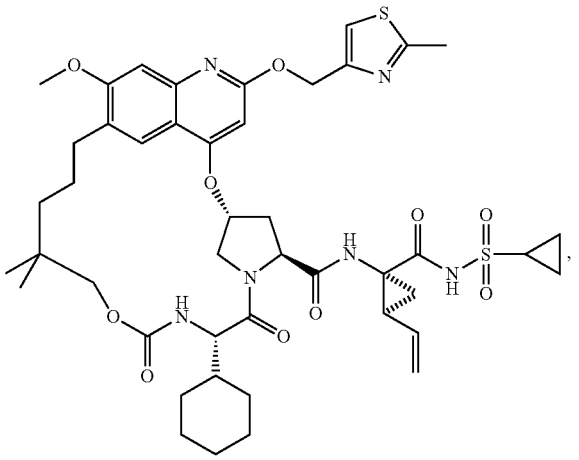
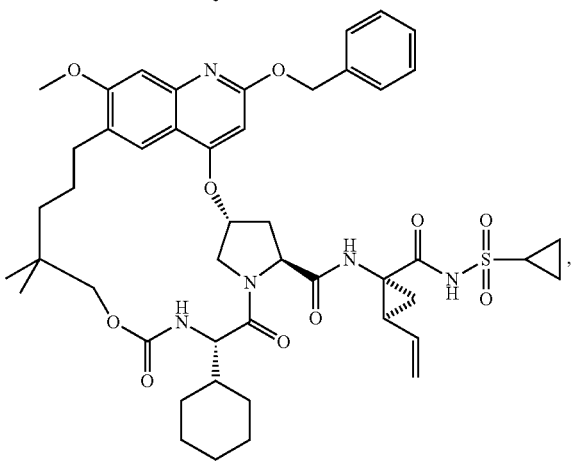
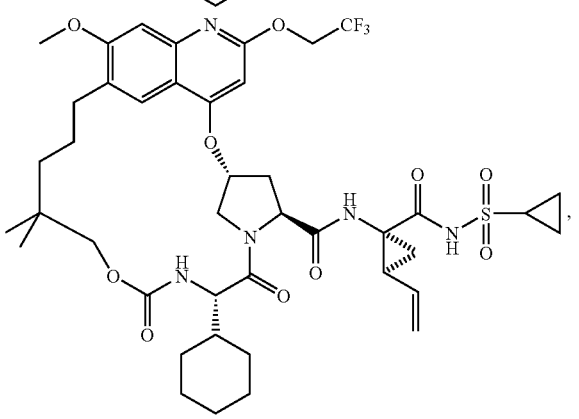
128
-continued
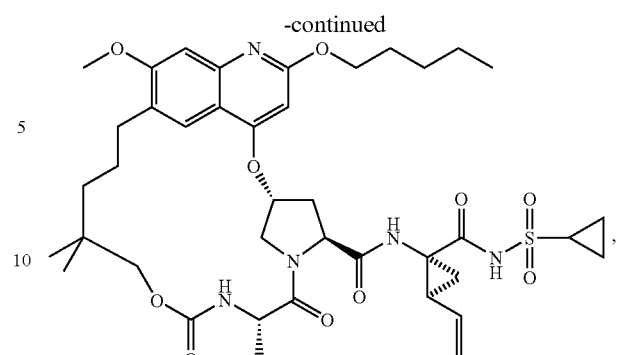
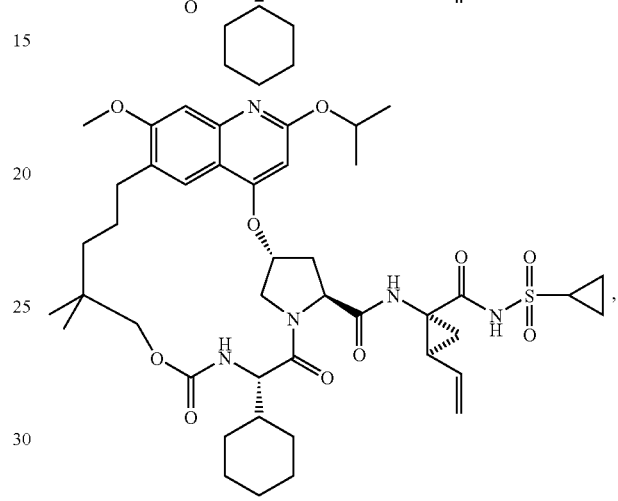
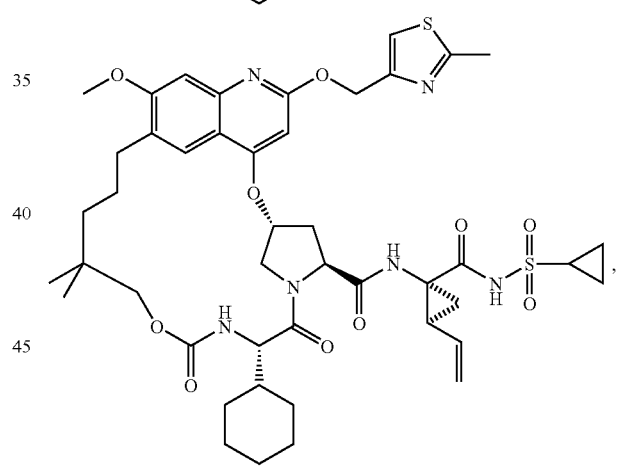
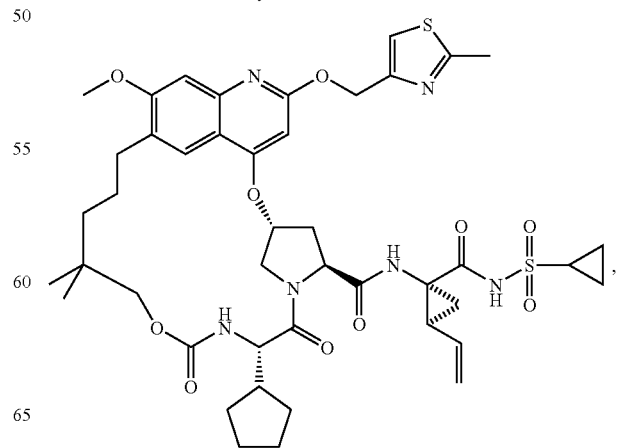

129
-continued
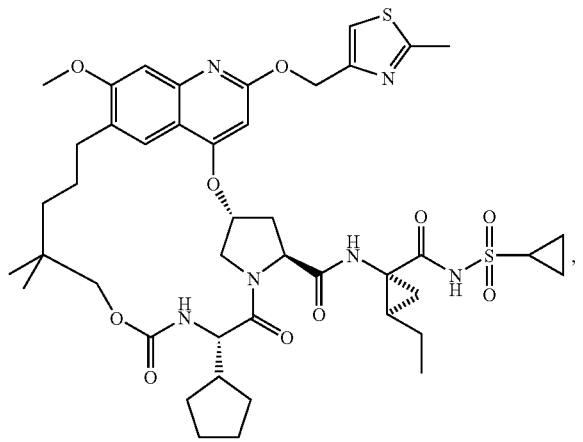
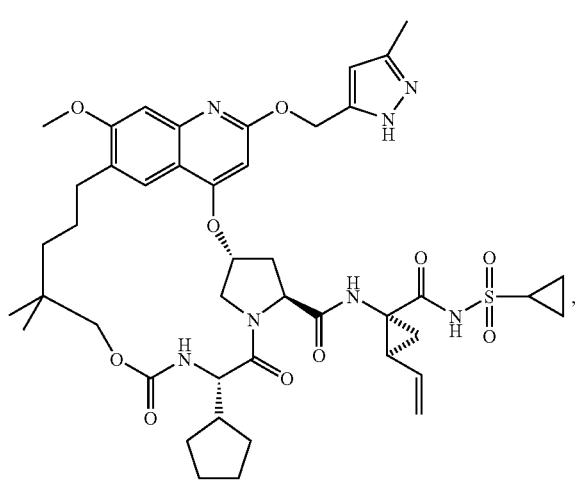
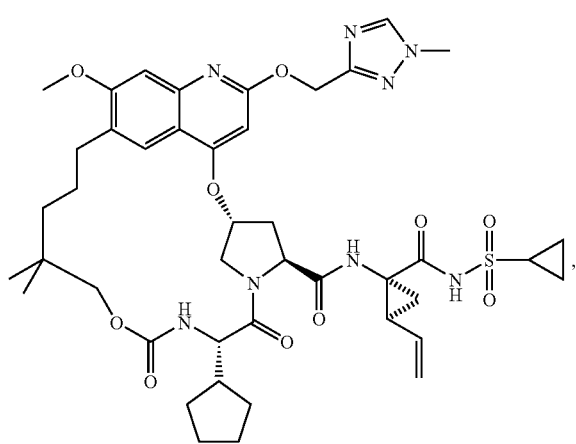
130
-continued
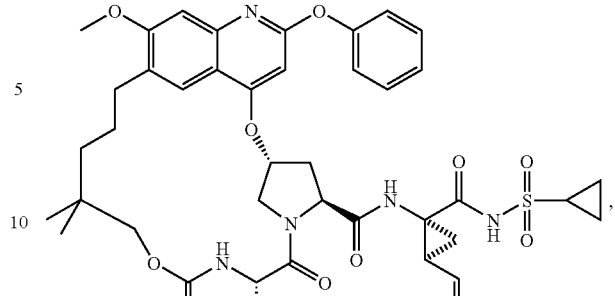
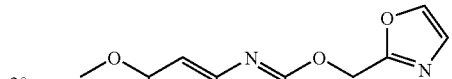
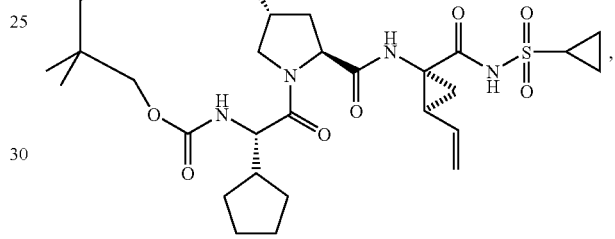
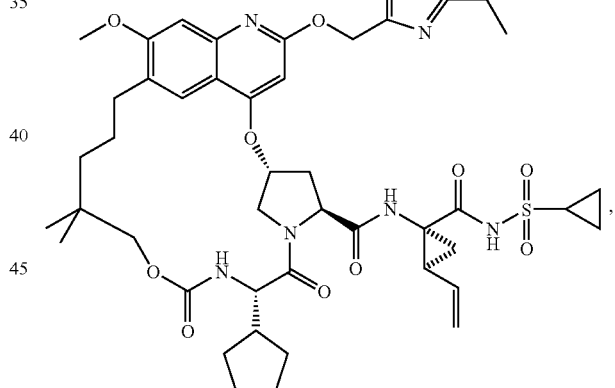
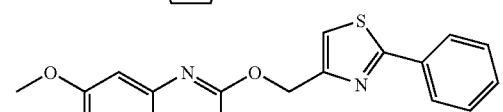
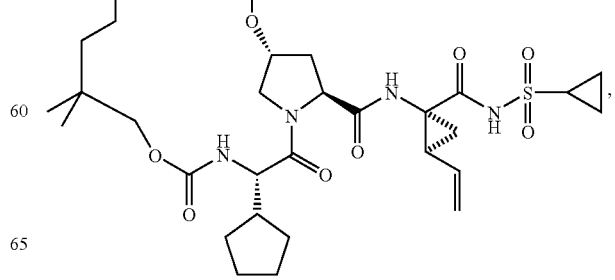

131
-continued
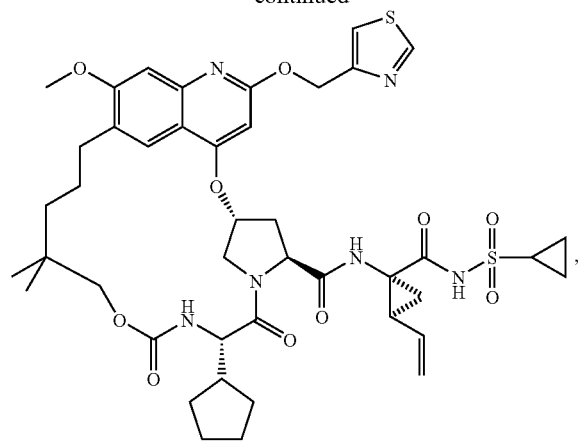
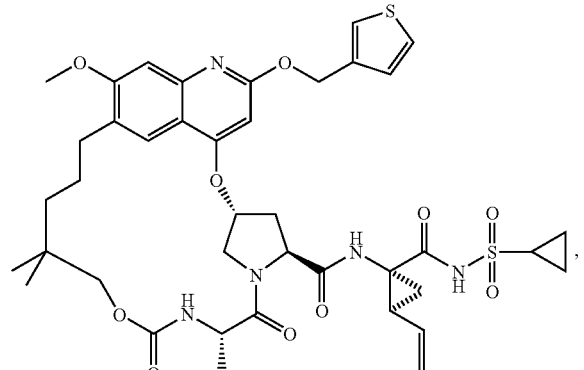
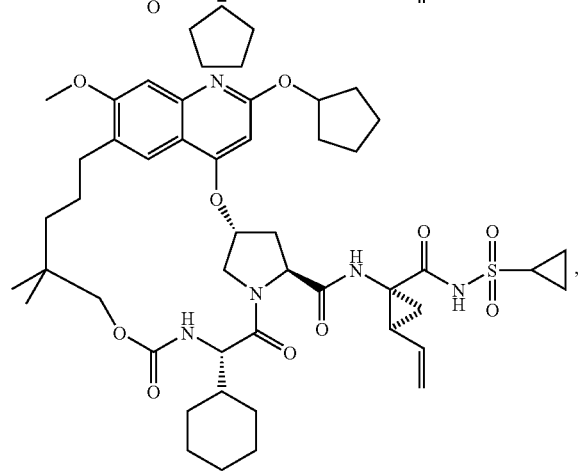
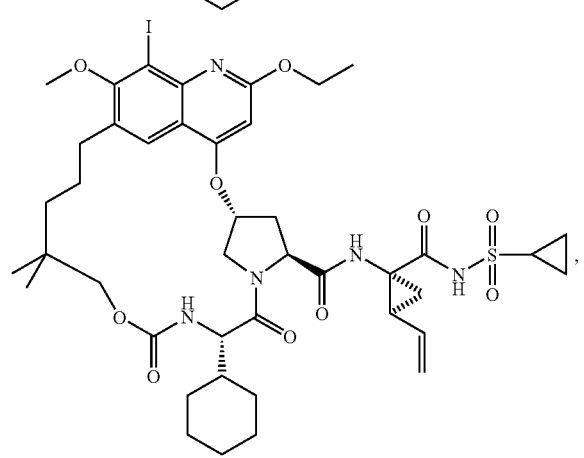
132
-continued
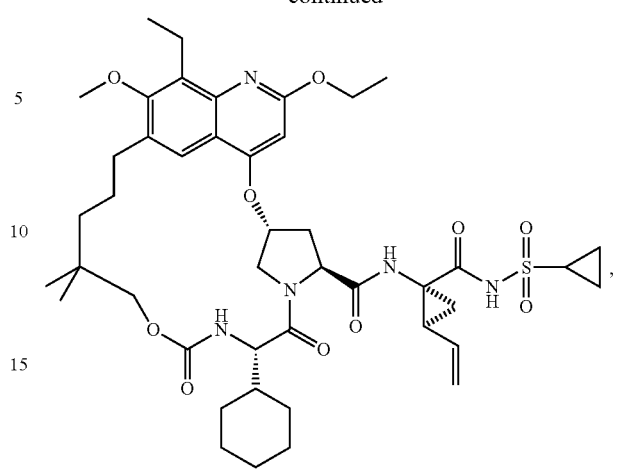
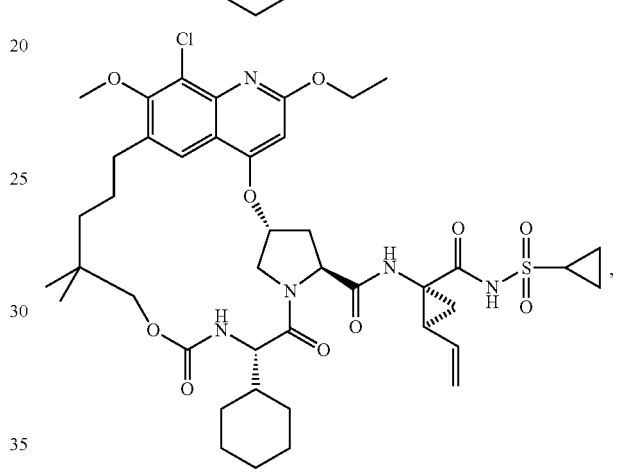
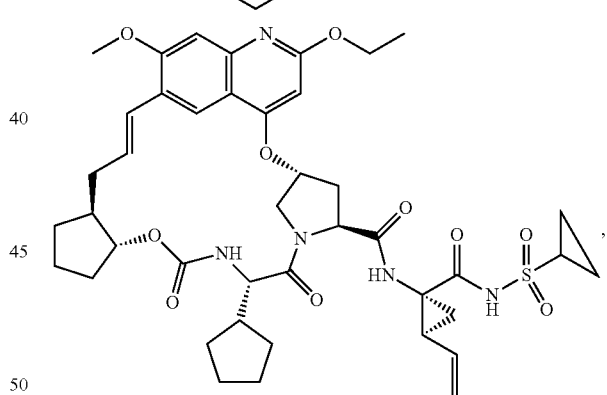
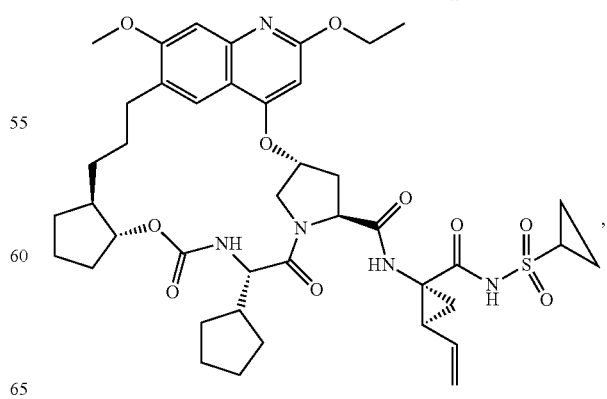

133                                   134
-continued                          -continued
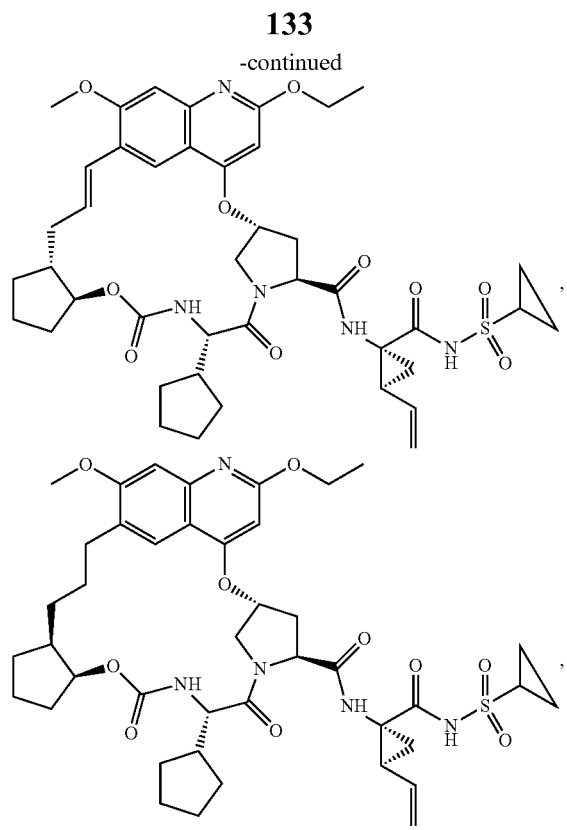
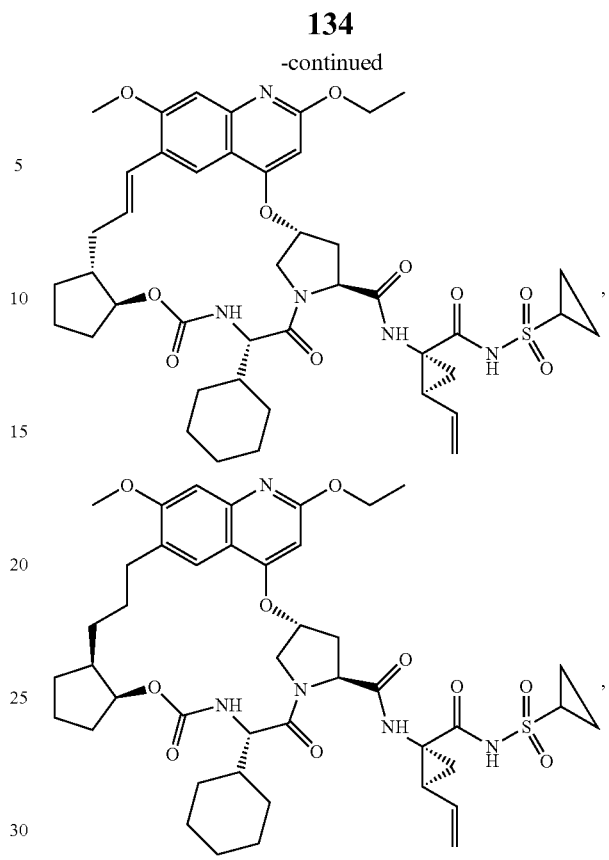
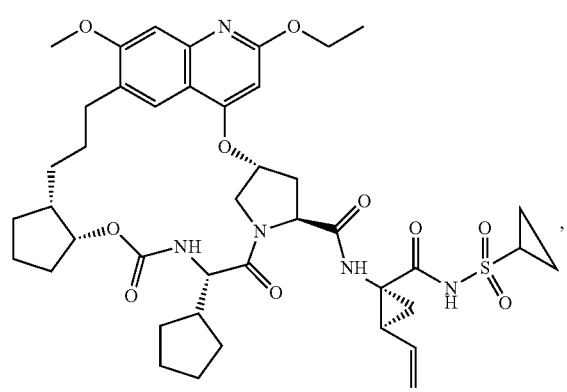
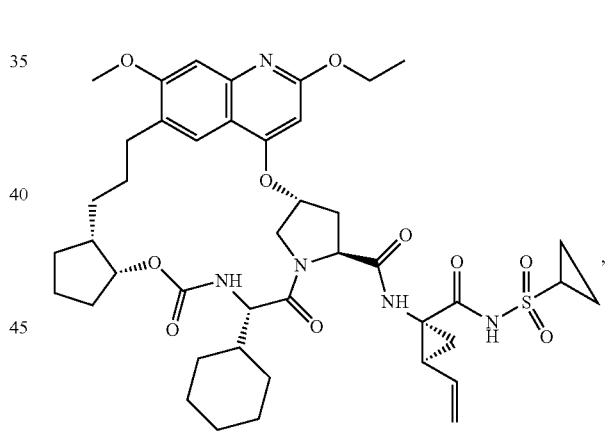
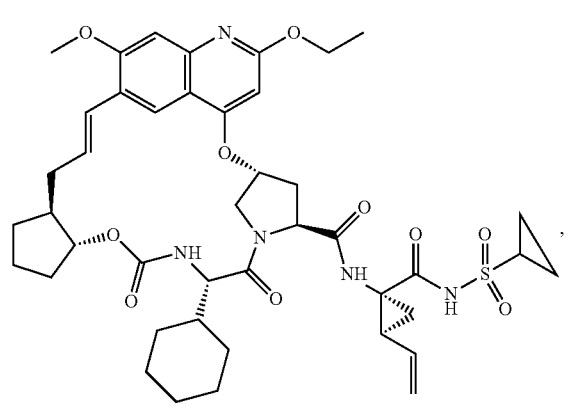
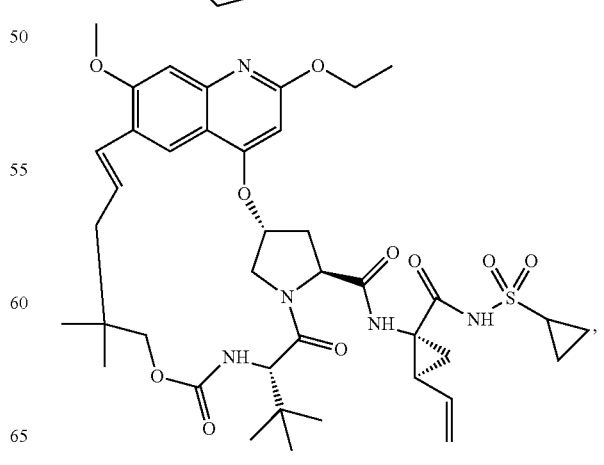

135
-continued
136
-continued
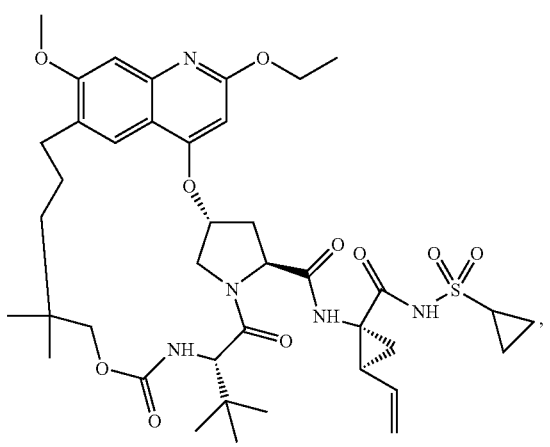
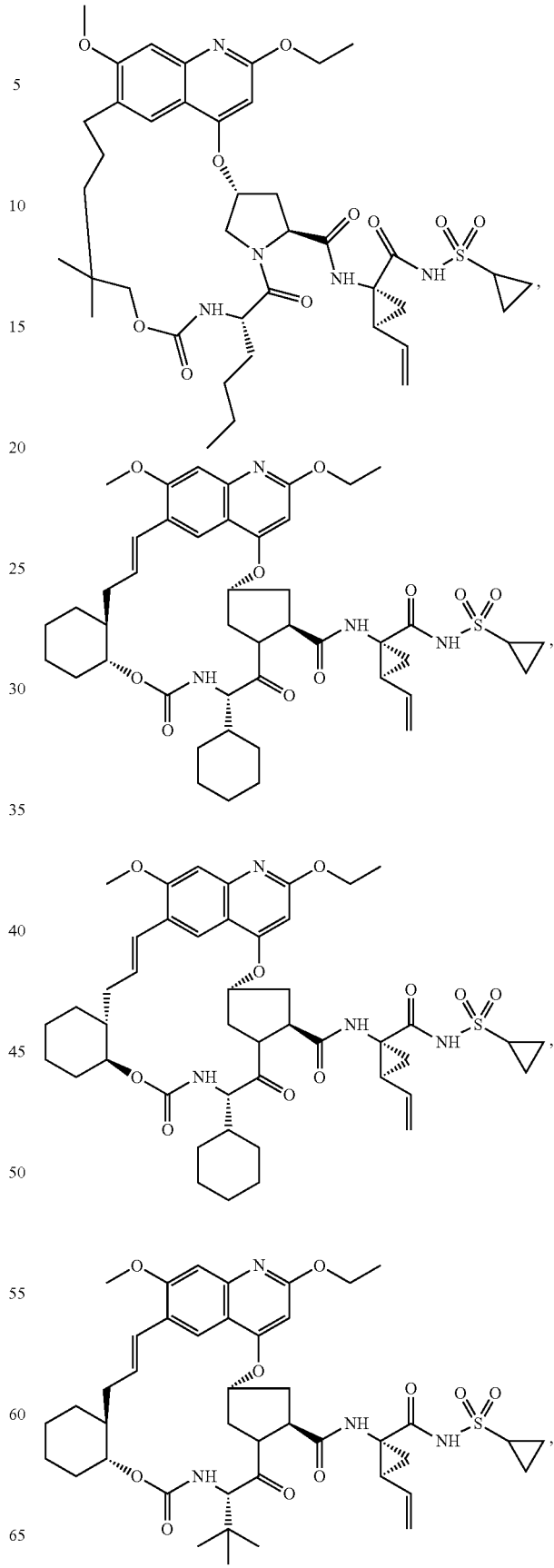

137
-continued
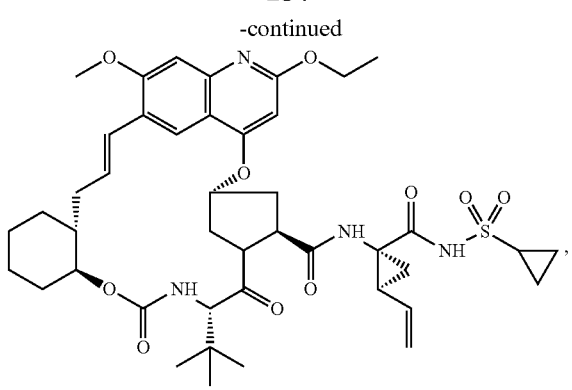
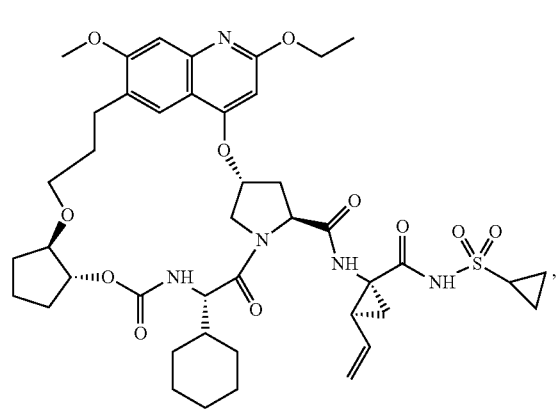
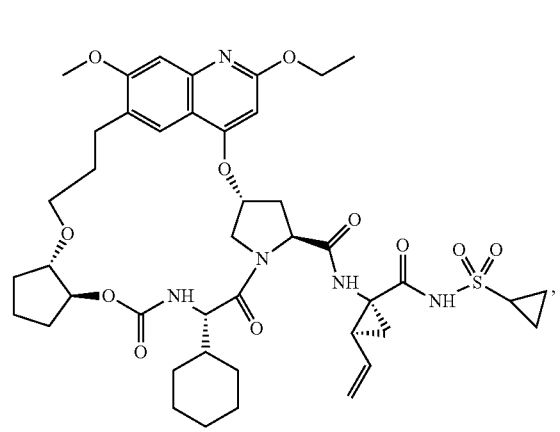
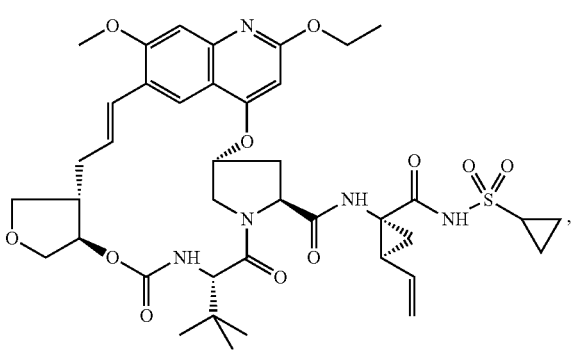
138
-continued
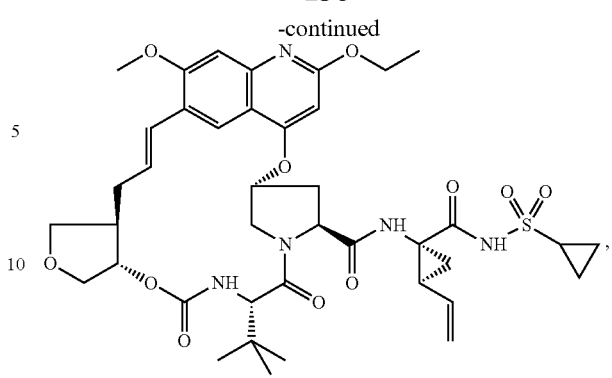
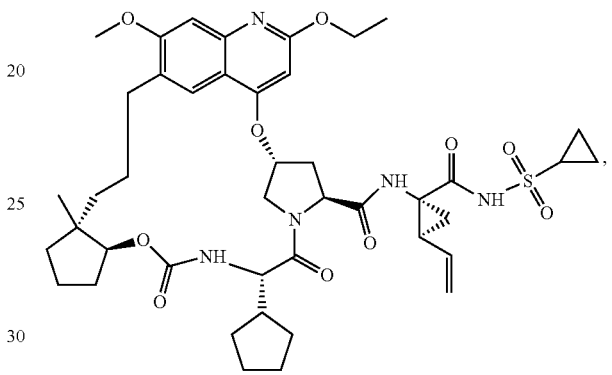
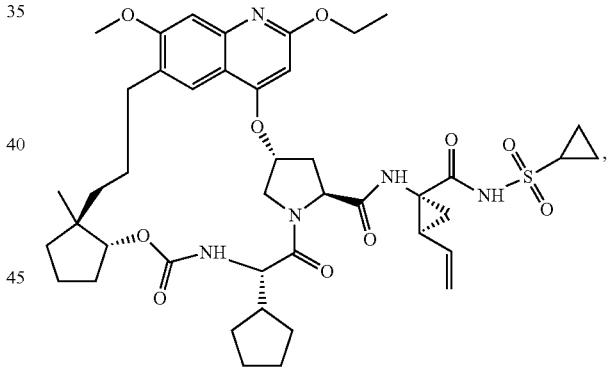
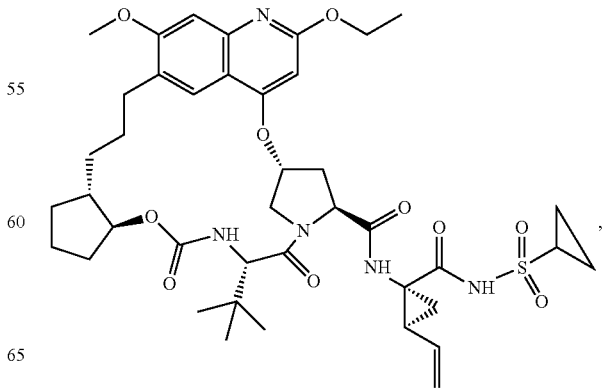

139
-continued
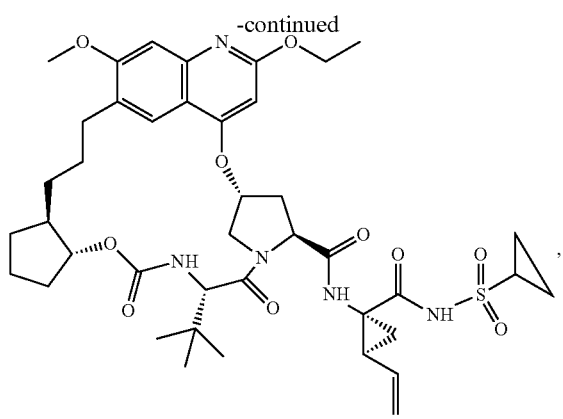
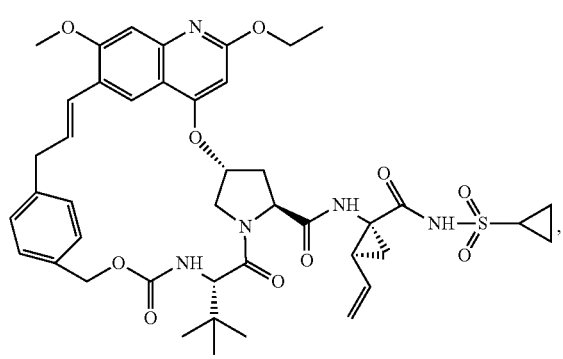
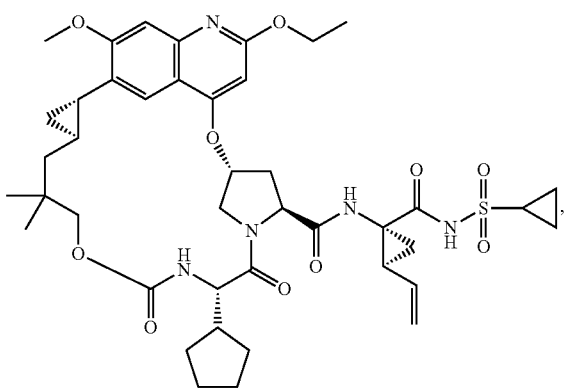
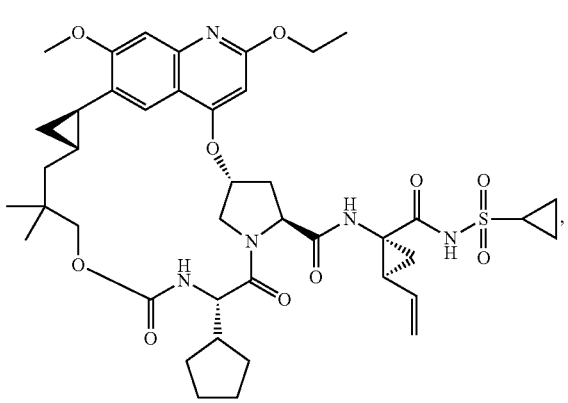
140
-continued
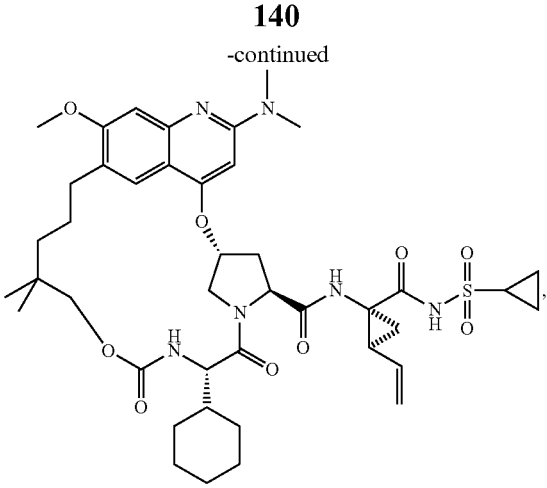
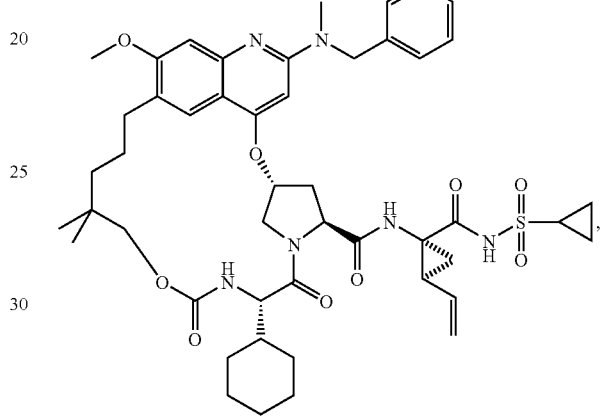
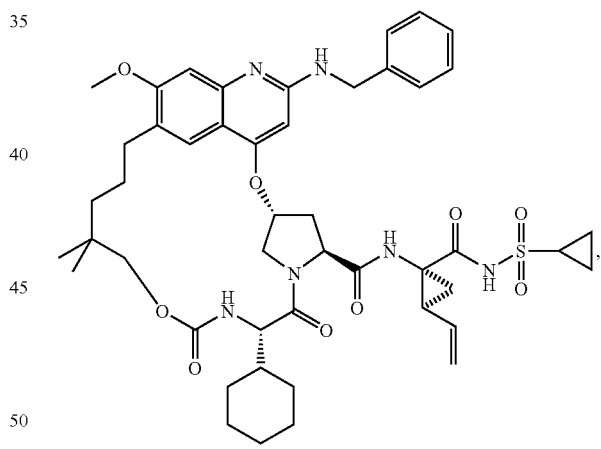
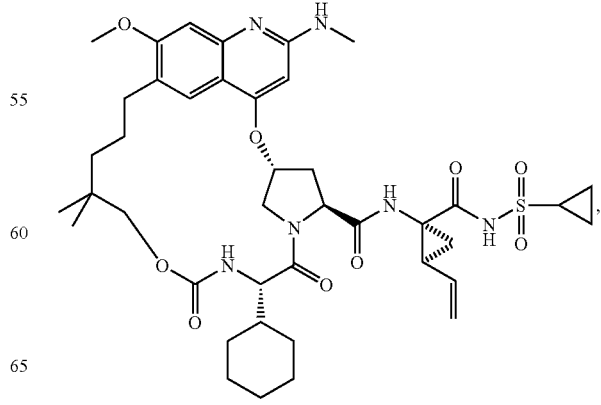

141
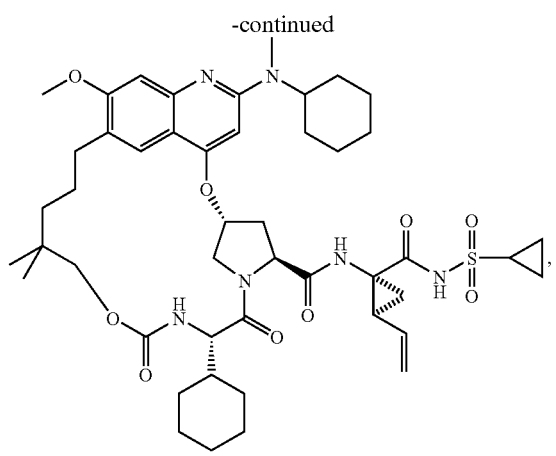
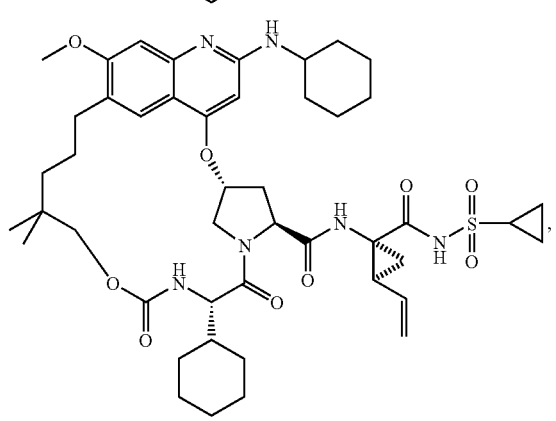
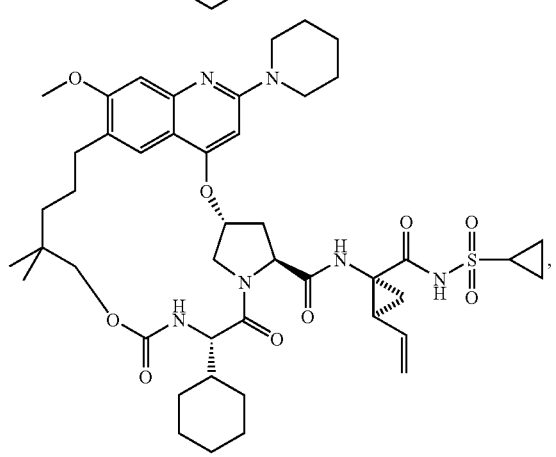
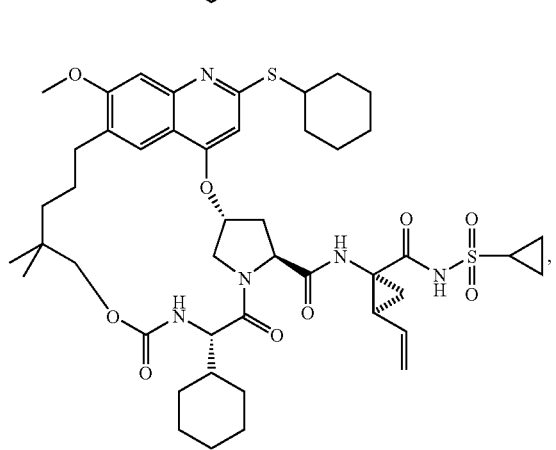
142
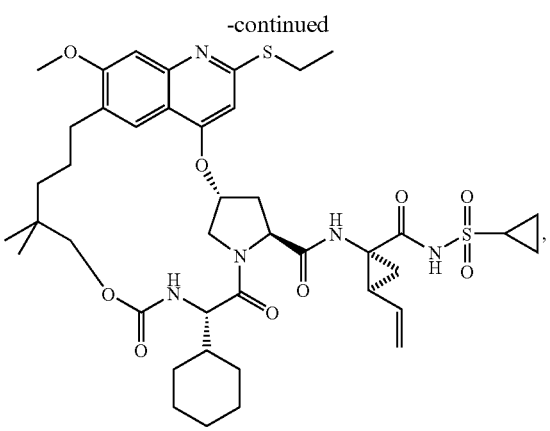
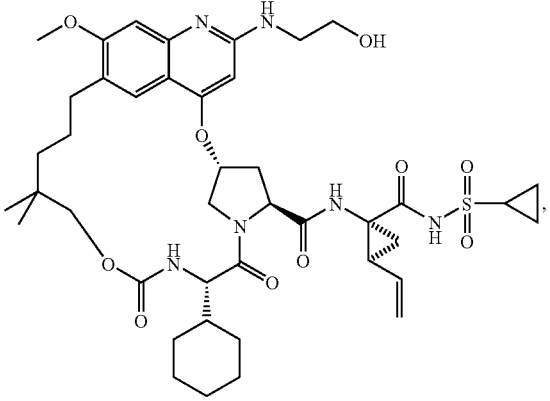
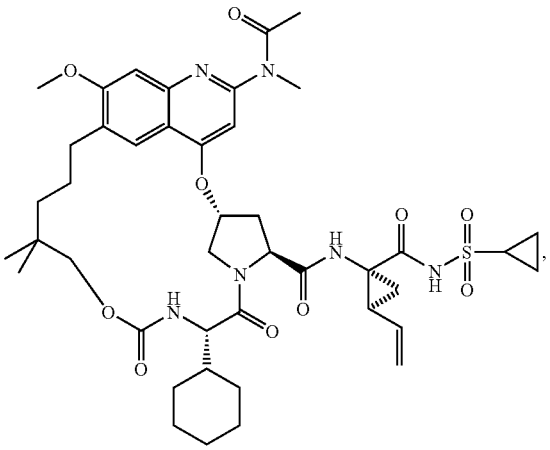
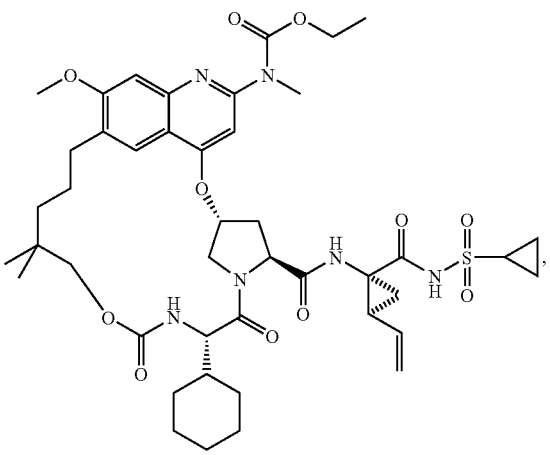

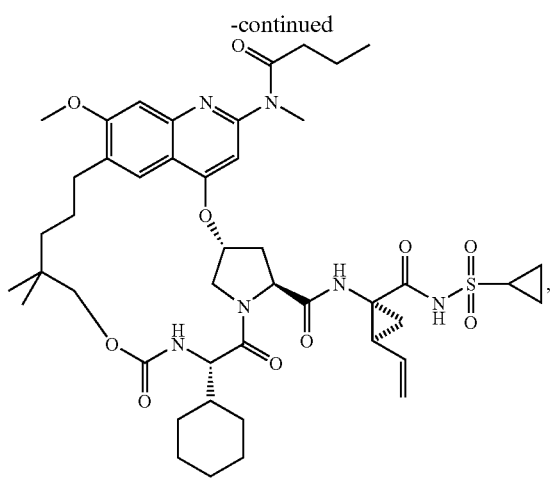

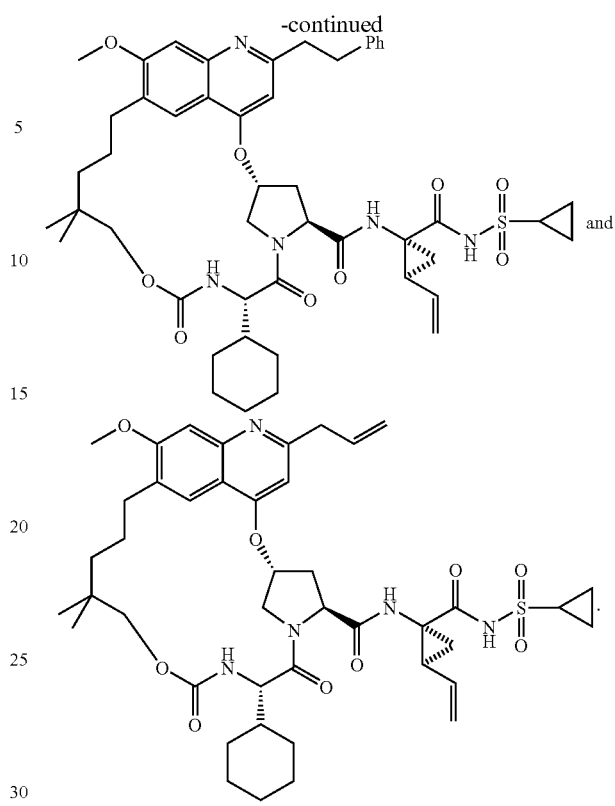

21. A pharmaceutical composition comprising an effective amount of a compound of claim 1, and a pharmaceutically acceptable carrier.

22. A pharmaceutical composition of claim 21, further comprising a second therapeutic agent selected from the group consisting of a HCV antiviral agent, an immunomodulator, and an anti-infective agent.

23. A method of manufacturing a medicament for treating infection by HCV in a subject in need thereof, said method comprising providing a compound of formula (I):

(I)

or a pharmaceutically acceptable salt thereof, wherein:
$R_1$ is OH, $NHSO_2R_6$, $NHSO_2NR_8R_9$, or $NHP(O)R_{11}R_{12}$;
$R_2$ is $C_1$-$C_4$ alkyl or $C_2$-$C_4$ alkenyl, wherein said alkyl or alkenyl is substituted with 0 to 3 halo;
$R_3$ is $C_1$-$C_8$ alkyl, $C_3$-$C_8$ cycloalkyl($C_1$-$C_8$)alkyl, aryl($C_1$-$C_8$)alkyl, Het, or $C_3$-$C_8$ cycloalkyl, wherein aryl is phenyl or naphthyl, and each alkyl, cycloalkyl, or aryl is substituted with 0 to 3 substituents selected from the group consisting of halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

Het is a 5- to 6-membered saturated cyclic ring having 1 or 2 heteroatoms selected from N, O and S, wherein said ring is substituted with 0 to 3 substituents selected from halo, $OR_{10}$, $SR_{10}$, $N(R_{10})_2$, $C_1$-$C_6$ alkyl, $C_1$-$C_6$ haloalkyl, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$;

each $R_4$ is independently H, $C_1$-$C_6$ alkyl, halogen or $OR_{10}$;

$R_5$ is $C_1$-$C_8$ alkyl, aryl, heteroaryl, heterocyclyl, $C_3$-$C_8$ cycloalkyl, $C_1$-$C_6$ haloalkyl or $C_1$-$C_6$ thioalkyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl or alkyl is substituted with 0 to 4 substituents selected from the group consisting of halo, $OR_{10}$, $SR_{10}$, $N(R_7)_2$, $C_1$-$C_6$ alkyl, aryl, heteroaryl, heterocyclyl, $C_1$-$C_6$ haloalkyl, $C_3$-$C_6$ cycloalkyl, cycloalkoxy, $NO_2$, CN, $CF_3$, $SO_2(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $CON(R_{10})_2$, and wherein said heteroaryl or heterocyclyl substituent is unsubstituted or substituted with $C_1$-$C_6$ alkyl or aryl;

each $R_6$ is independently $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is substituted with 0 to 2 W substituents or $P(O)R_{11}R_{12}$, and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

W is H, halo, $OR_{10}$, $C_1$-$C_6$ alkyl, CN, $CF_3$, $SR_{10}$, $SO_2(C_1$-$C_6$ alkyl), $C_3$-$C_8$ cycloalkyl, $C_3$-$C_8$ cycloalkoxy, $C_1$-$C_6$ haloalkyl, or $N(R_7)_2$;

each $R_7$ is independently H, $C_1$-$C_6$ alkyl or $C_3$-$C_6$ cycloalkyl;

X is O, NH, $N(CH_3)$, $N(C(O)CH_3)$, $N(C(O)OCH_2CH_3)$, $CH_2$ or S;

or X—$R_5$ is a heterocyclyl ring wherein the point of attachment is the heteroatom;

M is $C_1$-$C_8$ alkylene, $C_2$-$C_8$ alkenylene or ($C_1$-$C_8$ alkylene)-O—($C_1$-$C_8$ alkylene), wherein said $C_1$-$C_8$ alkylene, $C_2$-$C_8$ alkenylene or ($C_1$-$C_8$ alkylene)-O—($C_1$-$C_8$ alkylene) is substituted with 0 to 4 substituents selected from the group consisting of $C_1$-$C_8$ alkyl, $C_3$-$C_8$ cycloalkyl($C_1$-$C_8$ alkyl), aryl($C_1$-$C_8$ alkyl), and $N(R_4)_2$; where 2 adjacent substituents of M are optionally taken together to form a 3- to 6-membered cyclic ring;

$R_8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, aryl, heteroaryl or heterocyclyl is substituted with 0 to 4 substituents selected from the group consisting of aryl, $C_3$-$C_8$ cycloalkyl, heteroaryl, heterocyclyl, $C_1$-$C_6$ alkyl, halo ($C_1$-$C_6$ alkoxy), halo, $OR_{10}$, $SR_{10}$, $N(R_{10})_2$, $N(C_1$-$C_6$ alkyl)O($C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R_9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl ($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, alkoxy, cycloalkoxy, aryl, heteroaryl or heterocyclyl is substituted with 0 to 4 substituents selected from the group consisting of aryl, $C_3$-$C_8$ cycloalkyl, heteroaryl, heterocyclyl, $C_1$-$C_6$ alkyl, halo ($C_1$-$C_6$ alkoxy), halo, $OR_{10}$, $SR_{10}$, $N(R_{10})_2$, $N(C_1$-$C_6$ alkyl)O($C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R_8$ and $R_9$ are optionally taken together, with the nitrogen atom to which they are attached, to form a 4- to 8-membered monocyclic ring containing 0 to 2 additional heteroatoms selected from N, O and S;

each $R_{10}$ is independently H or $C_1$-$C_6$ alkyl;

each $R_{11}$ is independently $OR_{13}$, $N(R_{10})$—V—$CO_2R_{10}$, O—V—$CO_2R_{10}$, S—V—$CO_2R_{10}$, $N(R_{10})(R_{13})$, $R_{14}$, or $N(R_{10})SO_2R_6$;

each $R_{12}$ is independently $OR_{13}$, $N(R_{10})$—V—$CO_2R_{10}$, O—V—$CO_2R_{10}$, S—V—$CO_2R_{10}$, or $N(R_{10})(R_{13})$;

or $R_{11}$ and $R_{12}$ are optionally taken together, with the phosphorus atom to which they are attached, to form a 5- to 7-membered monocyclic ring;

each V is independently $CH(R_{15})$ or $C_1$-$C_4$ alkylene-CH ($R_{15}$);

each $R_{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is substituted with 0 to 2 substituents selected from the group consisting of aryl, aryl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R_{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is substituted with 0 to 2 substituents selected from the group consisting of $C_1$-$C_6$ alkyl, halo, OC(O)OR$_6$, OC(O)R$_6$, OR$_{10}$, SR$_{10}$, N(R$_{10}$)$_2$, C(O)R$_{10}$, NO$_2$, CN, CF$_3$, SO$_2$(C$_1$-C$_6$ alkyl), S(O)(C$_1$-C$_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and C(O)N(R$_{10}$)$_2$; and each $R_{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is substituted with 0 to 2 substituents selected from the group consisting of $C_1$-$C_6$ alkyl, halo, OC(O)OR$_6$, OC(O)R$_6$, OR$_{10}$, SR$_{10}$, N(R$_{10}$)$_2$, C(O)R$_{10}$, NO$_2$, CN, CF$_3$, SO$_2$(C$_1$-C$_6$ alkyl), S(O)(C$_1$-C$_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and C(O)N(R$_{10}$)$_2$; wherein each aryl is independently phenyl or naphthyl; each heteroaryl is independently a 5- or 6-membered aromatic ring having 1, 2 or 3 heteroatoms selected from N and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

24. A method of inhibiting HCV NS3 protease in a subject in need thereof, said method comprising administering to the subject an effective amount of a compound of formula (I):

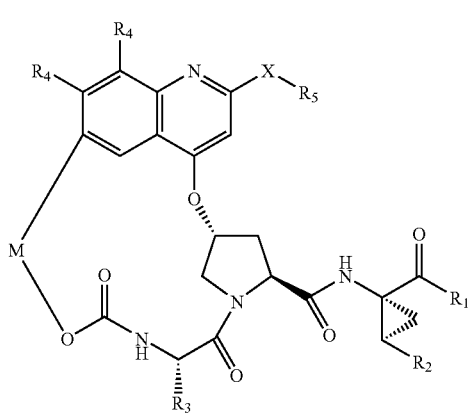

(I)

or a pharmaceutically acceptable salt thereof, wherein:

$R_1$ is OH, NHSO$_2$R$_6$, NHSO$_2$NR$_8$R$_9$, or NHP(O)R$_{11}$R$_{12}$;

$R_2$ is $C_1$-$C_4$ alkyl or $C_2$-$C_4$ alkenyl, wherein said alkyl or alkenyl is substituted with 0 to 3 halo;

$R_3$ is $C_1$-$C_8$ alkyl, $C_3$-$C_8$ cycloalkyl($C_1$-$C_8$)alkyl, aryl($C_1$-$C_8$)alkyl, Het, or $C_3$-$C_8$ cycloalkyl, wherein aryl is phenyl or naphthyl, and each alkyl, cycloalkyl, or aryl is substituted with 0 to 3 substituents selected from the group consisting of halo, OR$_{10}$, SR$_{10}$, N(R$_{10}$)$_2$, $C_1$-$C_6$ alkyl, $C_1$-$C_6$ haloalkyl, NO$_2$, CN, CF$_3$, SO$_2$(C$_1$-C$_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and CON(R$_{10}$)$_2$;

Het is a 5- to 6-membered saturated cyclic ring having 1 or 2 heteroatoms selected from N, O and S, wherein said ring is substituted with 0 to 3 substituents selected from halo, OR$_{10}$, SR$_{10}$, N(R$_{10}$)$_2$, $C_1$-$C_6$ alkyl, $C_1$-$C_6$ haloalkyl, NO$_2$, CN, CF$_3$, SO$_2$(C$_1$-C$_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and CON(R$_{10}$)$_2$;

each $R_4$ is independently H, $C_1$-$C_6$ alkyl, halogen or OR$_{10}$;

$R_5$ is $C_1$-$C_8$ alkyl, aryl, heteroaryl, heterocyclyl, $C_3$-$C_8$ cycloalkyl, $C_1$-$C_6$ haloalkyl or $C_1$-$C_6$ thioalkyl; wherein aryl is phenyl or naphthyl, heteroaryl is a 5- or 6-membered aromatic ring having 1, 2 or 3 heteroatoms selected from N, O and S, attached through a ring carbon or nitrogen, and heterocyclyl is a 5- to 7-membered saturated or unsaturated non-aromatic ring having 1, 2, 3 or 4 heteroatoms selected from N, O and S, attached through a ring carbon or nitrogen; and wherein said aryl, heteroaryl, heterocyclyl, cycloalkyl or alkyl is substituted with 0 to 4 substituents selected from the group consisting of halo, OR$_{10}$, SR$_{10}$, N(R$_7$)$_2$, $C_1$-$C_6$ alkyl, aryl, heteroaryl, heterocyclyl, $C_1$-$C_6$ haloalkyl, $C_3$-$C_6$ cycloalkyl, cycloalkoxy, NO$_2$, CN, CF$_3$, SO$_2$(C$_1$-C$_6$ alkyl), NR$_{10}$SO$_2$R$_6$, SO$_2$N(R$_6$)$_2$, NHCOOR$_6$, NHCOR$_6$, NHCONHR$_6$, CO$_2$R$_{10}$, and CON(R$_{10}$)$_2$, and wherein said heteroaryl or heterocyclyl substituent is unsubstituted or substituted with $C_1$-$C_6$ alkyl or aryl;

each $R_6$ is independently $C_1$-$C_6$ alkyl, $C_3$-$C_6$ cycloalkyl, $C_3$-$C_6$ cycloalkyl($C_1$-$C_5$)alkyl, aryl, aryl($C_1$-$C_4$)alkyl, heteroaryl, heteroaryl($C_1$-$C_4$ alkyl), heterocyclyl, or heterocyclyl($C_1$-$C_8$ alkyl), wherein said alkyl, cycloalkyl, aryl, heteroaryl, or heterocyclyl is substituted with 0 to 2 W substituents or P(O)R$_{11}$R$_{12}$, and wherein each aryl is independently phenyl or naphthyl, each heteroaryl is independently a 5- or 6-membered aromatic ring having 1, 2 or 3 heteroatoms selected from N, O and S, attached through a ring carbon or nitrogen, and each heterocyclyl is independently a 5- to 7-membered saturated or unsaturated non-aromatic ring having 1, 2, 3 or 4 heteroatoms selected from N, O and S, attached through a ring carbon or nitrogen;

W is H, halo, OR$_{10}$, $C_1$-$C_6$ alkyl, CN, CF$_3$, SR$_{10}$, SO$_2$(C$_1$-C$_6$ alkyl), $C_3$-$C_8$ cycloalkyl, $C_3$-$C_8$ cycloalkoxy, $C_1$-$C_6$ haloalkyl, or N(R$_7$)$_2$;

each $R_7$ is independently H, $C_1$-$C_6$ alkyl or $C_3$-$C_6$ cycloalkyl;

X is O, NH, N(CH$_3$), N(C(O)CH$_3$), N(C(O)OCH$_2$CH$_3$), CH$_2$ or S;

or X—$R_5$ is a heterocyclyl ring wherein the point of attachment is the heteroatom;

M is $C_1$-$C_8$ alkylene, $C_2$-$C_8$ alkenylene or ($C_1$-$C_8$ alkylene)-O—($C_1$-$C_8$ alkylene), wherein said $C_1$-$C_8$ alkylene, $C_2$-$C_8$ alkenylene or ($C_1$-$C_8$ alkylene)-O—($C_1$-$C_8$ alkylene) is substituted with 0 to 4 substituents selected from the group consisting of $C_1$-$C_8$ alkyl, $C_3$-$C_8$ cycloalkyl($C_1$-$C_8$ alkyl), aryl($C_1$-$C_8$ alkyl), and N(R$_4$)$_2$; where 2 adjacent substituents of M are optionally taken together to form a 3- to 6-membered cyclic ring;

$R_8$ is $C_1$-$C_8$ alkyl, $C_3$-$C_8$ cycloalkyl, $C_3$-$C_8$ cycloalkyl($C_1$-$C_8$ alkyl), aryl, aryl($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, aryl, heteroaryl or heterocyclyl is substituted with 0 to 4 substituents selected from the group consisting of aryl, $C_3$-$C_8$ cycloalkyl, heteroaryl, heterocyclyl, $C_1$-$C_6$ alkyl, halo ($C_1$-$C_6$ alkoxy), halo, $OR_{10}$, $SR_{10}$, $N(R_{10})_2$, $N(C_1$-$C_6$ alkyl)$O(C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R_9$ is $C_1$-$C_8$ alkyl, $C_3$-$C_8$ cycloalkyl, $C_3$-$C_8$ cycloalkyl($C_1$-$C_8$ alkyl), $C_1$-$C_8$ alkoxy, $C_3$-$C_8$ cycloalkoxy, aryl, aryl ($C_1$-$C_4$ alkyl), heteroaryl, heterocyclyl, heteroaryl($C_1$-$C_4$ alkyl), or heterocyclyl($C_1$-$C_8$ alkyl), wherein said alkyl, cycloalkyl, alkoxy, cycloalkoxy, aryl, heteroaryl or heterocyclyl is substituted with 0 to 4 substituents selected from the group consisting of aryl, $C_3$-$C_8$ cycloalkyl, heteroaryl, heterocyclyl, $C_1$-$C_6$ alkyl, halo ($C_1$-$C_6$ alkoxy), halo, $OR_{10}$, $SR_{10}$, $N(R_{10})_2$, $N(C_1$-$C_6$ alkyl)$O(C_1$-$C_6$ alkyl), $C_1$-$C_6$ alkyl, $C(O)R_{10}$, $C_1$-$C_6$ haloalkyl, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

or $R_8$ and $R_9$ are optionally taken together, with the nitrogen atom to which they are attached, to form a 4- to 8-membered monocyclic ring containing 0 to 2 additional heteroatoms selected from N, O and S;

each $R_{10}$ is independently H or $C_1$-$C_6$ alkyl;

each $R_{11}$ is independently $OR_{13}$, $N(R_{10})$—V—$CO_2R_{10}$, O—V—$CO_2R_{10}$, S—V—$CO_2R_{10}$, $N(R_{10})(R_{13})$, $R_{14}$, or $N(R_{10})SO_2R_6$;

each $R_{12}$ is independently $OR_{13}$, $N(R_{10})$—V—$CO_2R_{10}$, O—V—$CO_2R_{10}$, S—V—$CO_2R_{10}$, or $N(R_{10})(R_{13})$;

or $R_{11}$ and $R_{12}$ are optionally taken together, with the phosphorus atom to which they are attached, to form a 5- to 7-membered monocyclic ring;

each V is independently $CH(R_{15})$ or $C_1$-$C_4$ alkylene-CH($R_{15}$);

each $R_{13}$ is independently H, $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is substituted with 0 to 2 substituents selected from the group consisting of aryl, aryl($C_1$-$C_4$ alkyl), $C_3$-$C_8$ cycloalkyl, $C_3$-$C_8$ cycloalkyl($C_1$-$C_4$ alkyl), heteroaryl, heteroaryl($C_1$-$C_4$ alkyl), heterocyclyl, heterocyclyl($C_1$-$C_4$ alkyl), $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S;

$R_{14}$ is $C_1$-$C_6$ alkyl, $C_2$-$C_6$ alkenyl, aryl or heteroaryl, wherein aryl is phenyl or naphthyl, and heteroaryl is independently a 5- or 6-membered aromatic ring having 1, 2 or 3 heteroatoms selected from N, O and S, attached through a ring carbon or nitrogen, and wherein said aryl or heteroaryl is substituted with 0 to 2 substituents selected from the group consisting of $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; and each $R_{15}$ is independently $C_1$-$C_6$ alkyl, $C_2$-$C_6$ alkenyl, $C_3$-$C_8$ cycloalkyl, aryl, heteroaryl, or heterocyclyl, wherein said alkyl, alkenyl, cycloalkyl, aryl, heteroaryl or heterocyclyl is substituted with 0 to 2 substituents selected from the group consisting of $C_1$-$C_6$ alkyl, halo, $OC(O)OR_6$, $OC(O)R_6$, $OR_{10}$, $SR_{10}$, $N(R_{10})_2$, $C(O)R_{10}$, $NO_2$, CN, $CF_3$, $SO_2(C_1$-$C_6$ alkyl), $S(O)(C_1$-$C_6$ alkyl), $NR_{10}SO_2R_6$, $SO_2N(R_6)_2$, $NHCOOR_6$, $NHCOR_6$, $NHCONHR_6$, $CO_2R_{10}$, and $C(O)N(R_{10})_2$; wherein each aryl is independently phenyl or naphthyl; each heteroaryl is independently a 5- or 6-membered aromatic ring having 1, 2 or 3 heteroatoms selected from N, O and S, attached through a ring carbon or nitrogen; and each heterocyclyl is independently a 5- to 7-membered saturated or unsaturated non-aromatic ring having 1, 2, 3 or 4 heteroatoms selected from N, O and S, attached through a ring carbon or nitrogen; and wherein 2 adjacent substituents of said cycloalkyl, cycloalkoxy, aryl, heteroaryl or heterocyclyl are optionally taken together to form a 3- to 6-membered cyclic ring containing 0 to 3 heteroatoms selected from N, O and S.

\* \* \* \* \*